(12) United States Patent
Bonazzi et al.

(10) Patent No.: US 12,091,424 B2
(45) Date of Patent: *Sep. 17, 2024

(54) RAPAMYCIN DERIVATIVES

(71) Applicant: NOVARTIS AG, Basel (CH)

(72) Inventors: Simone Bonazzi, Cambridge, MA (US); Michael Connolly, Salem, MA (US); David Jonathan Glass, Cortland Manor, NY (US); Manuel Mihalic, Grenzach-Wyhlen (DE); Andrew William Patterson, Somerville, MA (US); Silvio Roggo, Muttenz (CH); Tea Shavlakadze, Hawthorne, NY (US)

(73) Assignee: NOVARTIS AG, Basel (CH)

( * ) Notice: Subject to any disclaimer, the term of this patent is extended or adjusted under 35 U.S.C. 154(b) by 80 days.

This patent is subject to a terminal disclaimer.

(21) Appl. No.: 17/499,433

(22) Filed: Oct. 12, 2021

(65) Prior Publication Data

US 2022/0242878 A1 Aug. 4, 2022

Related U.S. Application Data

(63) Continuation of application No. 17/004,434, filed on Aug. 27, 2020, now abandoned, which is a continuation of application No. 16/141,856, filed on Sep. 25, 2018, now Pat. No. 10,800,793.

(60) Provisional application No. 62/563,312, filed on Sep. 26, 2017.

(51) Int. Cl.
| | |
|---|---|
| C07D 498/18 | (2006.01) |
| A61P 1/16 | (2006.01) |
| A61P 3/04 | (2006.01) |
| A61P 3/10 | (2006.01) |
| A61P 9/10 | (2006.01) |
| A61P 9/12 | (2006.01) |
| A61P 11/00 | (2006.01) |
| A61P 13/12 | (2006.01) |
| A61P 19/00 | (2006.01) |
| A61P 19/02 | (2006.01) |
| A61P 19/10 | (2006.01) |
| A61P 25/02 | (2006.01) |
| A61P 25/16 | (2006.01) |
| A61P 25/28 | (2006.01) |
| A61P 29/00 | (2006.01) |
| A61P 31/10 | (2006.01) |
| A61P 35/00 | (2006.01) |

(Continued)

(52) U.S. Cl.
CPC .............. *C07D 498/18* (2013.01); *A61P 1/16* (2018.01); *A61P 3/04* (2018.01); *A61P 3/10* (2018.01); *A61P 9/10* (2018.01); *A61P 9/12* (2018.01); *A61P 11/00* (2018.01); *A61P 13/12* (2018.01); *A61P 19/00* (2018.01); *A61P 19/02* (2018.01); *A61P 19/10* (2018.01); *A61P 25/02* (2018.01); *A61P 25/16* (2018.01); *A61P 25/28* (2018.01); *A61P 29/00* (2018.01); *A61P 31/10* (2018.01); *A61P 35/00* (2018.01); *A61P 37/00* (2018.01); *C07F 9/6561* (2013.01)

(58) Field of Classification Search
None
See application file for complete search history.

(56) References Cited

U.S. PATENT DOCUMENTS

| | | |
|---|---|---|
| 3,929,992 A | 12/1975 | Sehgal et al. |
| 4,316,885 A | 2/1982 | Rakhit |
| 4,650,803 A | 3/1987 | Stella et al. |

(Continued)

FOREIGN PATENT DOCUMENTS

| | | |
|---|---|---|
| CN | 101389337 A | 3/2009 |
| EA | 011488 B1 | 4/2009 |

(Continued)

OTHER PUBLICATIONS

Baker, Darren J. et al.: "Naturally occurring p16Ink4a-positive cells shorten healthy lifespan", Nature, (2016), vol. 530, pp. 184-203.

(Continued)

*Primary Examiner* — Po-Chih Chen
(74) *Attorney, Agent, or Firm* — Morrison & Foerster LLP

(57) ABSTRACT

The disclosure relates to compounds of formula (I)

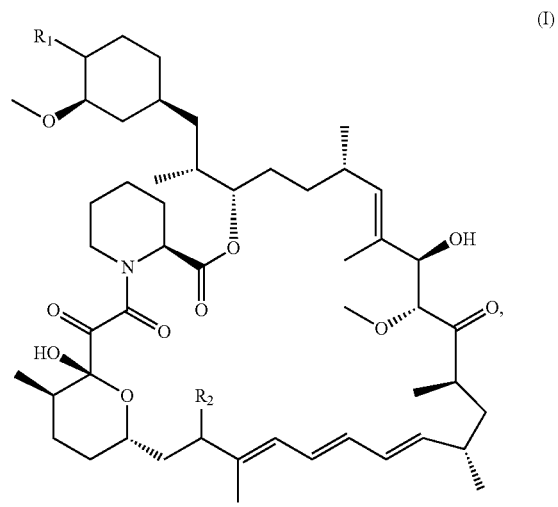

and pharmaceutically acceptable salts, and compositions thereof, wherein the substituents are as defined herein. Also provided are methods of making compounds of formula (I), and methods involving the compounds or compositions for treating disorders and diseases described herein.

23 Claims, 12 Drawing Sheets

Specification includes a Sequence Listing.

(51) Int. Cl.
A61P 37/00 (2006.01)
C07F 9/6561 (2006.01)

(56) References Cited

U.S. PATENT DOCUMENTS

| | | |
|---|---|---|
| 5,120,842 A | 6/1992 | Failli et al. |
| 5,151,413 A | 9/1992 | Caufield et al. |
| 5,258,389 A | 11/1993 | Goulet et al. |
| 5,362,718 A | 11/1994 | Skotnicki et al. |
| 5,527,907 A | 6/1996 | Or et al. |
| 5,665,772 A | 9/1997 | Cottens et al. |
| 5,985,890 A | 11/1999 | Cottens et al. |
| 6,384,046 B1 | 5/2002 | Schuler et al. |
| 8,906,374 B2 | 12/2014 | Kim et al. |
| 9,358,236 B2 | 6/2016 | Murphy et al. |
| 9,427,463 B2 | 8/2016 | Kim et al. |
| 9,669,032 B2 | 6/2017 | Liu et al. |
| 9,683,048 B2 | 6/2017 | Freeman et al. |
| 2020/0392159 A1 | 12/2020 | Bonazzi et al. |
| 2022/0064185 A1 | 3/2022 | Bonazzi et al. |
| 2022/0202787 A1 | 6/2022 | Bonazzi et al. |

FOREIGN PATENT DOCUMENTS

| | | |
|---|---|---|
| EP | 1212331 B1 | 4/2004 |
| JP | H07509246 A | 10/1995 |
| JP | 2000510815 A | 8/2000 |
| JP | 2002508971 A | 3/2002 |
| JP | 2002514165 A | 5/2002 |
| JP | 2002514893 A | 5/2002 |
| JP | 2009527520 A | 7/2009 |
| KR | 19990022780 A | 3/1999 |
| RU | 2126409 C1 | 2/1999 |
| RU | 2325906 C2 | 6/2008 |
| WO | WO-1994002136 A1 | 2/1994 |
| WO | 96/41865 A2 | 12/1996 |
| WO | 97/35575 A1 | 10/1997 |
| WO | 99/36553 A2 | 7/1999 |
| WO | 2007/085400 A1 | 8/2007 |
| WO | 2007/096174 A1 | 8/2007 |
| WO | 2008/022256 A2 | 2/2008 |
| WO | 2012/103959 A1 | 8/2012 |
| WO | WO-2016207205 A1 | 12/2016 |
| WO | 2017/044720 A1 | 3/2017 |
| WO | WO-2018204416 A1 | 11/2018 |

OTHER PUBLICATIONS

Buss, Sebastian J. et al.: "Beneficial Effects of Mammalian Target of Rapamycin Inhibition on Left Ventricular Remodeling After Myocardial Infarction", Journal of American College of Cardiology, (2009), vol. 54, No. 25, pp. 2435-2446.
Buss, Sebastian J. et al.: "Augmentation of autophagy by mTOR-inhibition in myocardial infarction: When size matters", Autophagy, (2010), vol. 6, Issue 2, pp. 304-306.
Chinnery, Patrick F .: "Mitochondrial disease in adults: what's old and what's new", EMBO Molecular Medicine, (2015), vol. 7, No. 2, pp. 1503-1512.
D'Arcy, Allan D. et al.: "An automated microseed matrix-screening method for protein crystallization", Acta Cyst. (2007), D63, pp. 550-554.
Ehninger, D. et al.: "Reversal of learning deficits in a Tsc2+/+ mouse model of tuberous sclerosis", Nature Medicine, Aug. 2008, vol. 14, No. 8, pp. 843-848.
Harrison, David E. et al.: "Rapamycin fed late in life extends lifespan in genetically heterogeneous mice", Nature, (2009), vol. 460, pp. 392-396.
Holmes, Gregory L.: "Tuberous Sclerosis Complex and Epilepsy: Recent Developments and Future Challanges", Epilepsia, (2007) vol. 48, No. 4, pp. 617-630.
Hughes, Philip et al.: "The Isolation, Synthesis and characterization of an Isomeric Form of Rapamycin", Tetrahedron Letters, (1992), vol. 33, No. 33, pp. 4739-4742.

Inoki, Ken et al.: "Dysregulation of the TSC-mTOR pathway in human disease", Nature Genetics, Jan. 2005, vol. 37, No. 7, pp. 19-24.
Kabat et al.: "Focal cortical dysplasia-review", Pol. J. Radiol., 2012; 77(2): 35-43.
Kaeberlein, Matt et al.: "Regulation of Yeast Replicative Life Span by TOR and Sch9 in Response to Nutrients", Science, (2005), vol. 310, pp. 1193-1196.
Kapahi, Pankaj et al.: "Regulation of Lifespan in *Drosophila* by Modulation of Genes in the TOR Signaling Pathway," Current Biology, 2004, vol. 14, pp. 885-890.
Khan, Nahid A. et al.: "mTORC1 Regulates Mitochondrial Integrated Stress Response and Mitochondrial Myopathy Progession", Cell Metabolism, (2017) vol. 26, pp. 419-428.
Koopman, Werner JH et al.: "Mitochondrial disorders in children: toward development of small-molecule treatment strategies", EMBO Molecular Medicine, vol. 8, No. 4, (2016), pp. 311-327.
Laplante, Mathieu et al.: "mTOR Signaling in Growth Control and Disease", Cell (2012), 149, pp. 274-293.
Lee, Chung-Han Lee, "mTOR Pathway as a Target in Tissue Hypertrophy", Ann. Rev. Pharmacol. Toxicol., 2007, vol. 47, pp. 443-467.
Leslie, M.: "A Putative Antiaging Drug Takes a Step From Mice to Men", Science, (2015) vol. 342.
Ljungberg, Cecilia M. et al.: "Rapamycin suppresses seizures and neuronal hypertrophy in a mouse model of cortical dysplasia", Dis Model Mech., Jul.-Aug. 2009, vol. 2, No. 7-8, pp. 389-398.
Mannick, Joan B. et al.: "mTOR inhibition improves immune function in the elderly", Science Translational Medicine, Dec. 24, 2014, vol. 268, pp. 1.
Manning, Brendan et al.: "Identification of the Tuberous Sclerosis Complex-2 Tumor Suppressor Gene Product Tuberin as a Target of the Phosphoinositide 3-Kinase/Akt Pathway", Molecular Cell, (2002), vol. 10, pp. 151-162.
Marz, Andreas et al.: "Large FK506-Binding Proteins Shape the Pharmacology of Rapamycin", Molecular and Cellular Biology, (2013), vol. 33, No. 7, pp. 1357-1367.
McApline, James B et al.: "Revised NMR Assignments for Rapamycin", The Journal of Antibiotics, Jun. 1991, vol. 44, No. 6, pp. 688-690.
Meikle, Lynsey et al.: "Response of a Neuronal Model of Tuberous Sclerosis to Mammalian Target of Rapamycin (mTOR) Inhibitors: Effects on mTORC1 and Akt Signaling Lead to Improved Survival and Function", The Journal of Neuroscience, May 2008, vol. 28, No. 21, pp. 5422-5432.
Mierke, Dale F. et al.: "97. Conformational Analysis of the cis- and trans-Isomers of FK506 by NMR and Molecular Dynamics", Helvetica Chimica Acta, vol. 74 (1991), pp. 1027-1045.
Pleniceanu, Oren et al.: "mTORC1 Inhibition is an Effective Treatment for Sporadic Renal Angiomyolipoma", Kidney International Reports, (2018), vol. 3, pp. 155-159.
Royce et al.: "Everolimus in the Treatment of Metastatic Breast Cancer", Breast Cancer: Basic and Clinical Research 2015, vol. 9, pp. 73-79.
Schreiber et al.: "Atomic Structure of the Rapamycin Human Immunophilin FKBP-12 Complex", J. Am. Chem. Soc., 1991, vol. 113, pp. 7433-7434.
Selman, Colin et al.: "Ribosomal Protein S6 Kinase 1 Signaling Regulates Mammalian Life Span", Science, (2009), vol. 326, pp. 140-144.
Vellai, Tibor et al.: "Influence of TOR kinase on lifespan in C. elegans", Nature, (2003), vol. 426, p. 620.
Villamil, Federico G. et al.: "Fibrosis progression in maintenance liver transplant patients with hepatitis C recurrence: a randomised study of everolimus vs. calcineurin inhibitors", Liver, (2014), pp. 1513-1521.
Wong, Michael: "Mammalian target of rapamycin (mTOR) activation in focal cortical dysplasia and related focal cortical malformations", Experimental Neurology, (2013), vol. 244, pp. 22-26.
Young, Matthew J. et al.: "Human mitochondrial DNA replication machinery and disease", Current Opinion in Genetics & Development, 2016, vol. 38, pp. 52-62.

(56) References Cited

OTHER PUBLICATIONS

Zeng, Ling-Hui et al.: "Rapamycin Prevents Epilepsy in a Mouse Model of Tuberous Sclerosis Complex", Ann. Neuorol., 2008, vol. 63, pp. 444-453.
Zeng, Ling-Hui et al.: "The Mammalian Target of Rapamycin Signaling Pathway Mediates Epileptogenesis in a Model of Temporal Lobe Epilepsy", The Journal of Neuroscience, (2009), vol. 29, No. 21, pp. 6964-6972.
Zhou, Jing et al.: "Pharmacological Inhibition of mTORCC1 Suppresses Anatomical, Cellular, and Behavioral Abnormalities in Neural-Specific Pten Knock-Out Mice", The Journal of Neuroscience, (2009). vol. 29, No. 6, pp. 1773-1783.
Notification of Transmittal of The International Search Report and Written Opinion of the International Searching Authority, or the Declaration, mailed on Jan. 3, 2019, issued in Int'l Appl. No. PCT/IB2018/057422, Int'l Filing Date: Sep. 25, 2018, 14 pages.
Bae-Jump et al., (2010). "Rapamycin inhibits cell proliferation in type I and type II endometrial carcinomas: a search for biomarkers of sensitivity to treatment," Gynecol Oncol, 119(3):579-585, 18 pages.
Baraz et al., (2014). "mTOR inhibition by everolimus in childhood acute lymphoblastic leukemia induces caspase—independent cell death," PLoS One, 9(7):e102494., 10 pages.
Bastin et al., (2000). "Salt Selection and Optimisation Procedures for Pharmaceutical New Chemical Entities," Organic Process Research & Development, 4(5):427-435.
Battelli et al., (2011). "mTOR inhibitors in renal cell carcinoma," Therapy, 8(4):359-367, 14 pages.
Bayle et al., (2006). "Rapamycin Analogs with Differential Binding Specificity Permit Orthogonal Control of Protein Activity," Chemistry And Biology, 13(1):99-107.
Belikov, (2007). "Chapter 2.6: Relationship between the chemical structure, properties of substances and their effect on the body," in Pharmaceutical Chemistry Med Press Inform, pp. 27-29, 9 pages, English translation.
Berge et al., (1977). "Pharmaceutical salts," J. Pharmaceutical Sciences, 66:1-19.
Cai et al., (2013). "mTOR inhibitor RAD001 (everolimus) induces apoptotic, not autophagic cell death, in human nasopharyngeal carcinoma cells," Int J Mol Med, 31(4):904-912.
Cassano et al., (2019). "Early intrathecal infusion of everolimus restores cognitive function and mood in a murine model of Alzheimer's disease," Exp Neurol, 311:88-105.
Chang et al., (2017). "Regression of Neonatal Cardiac Rhabdomyoma in Two Months Through Low-Dose Everolimus Therapy: A Report of Three Cases," Pediatr Cardiol, 38(7):1478-1484.
Ciolczyk-Wierzbicka et al., (2020). "mTOR inhibitor everolimus reduces invasiveness of melanoma cells," Hum Cell, 33(1):88-97.
Cuppens et al., (2017). "Potential Targets Analysis Reveals Dual PI3K/mTOR Pathway Inhibition as a Promising Therapeutic Strategy for Uterine Leiomyosarcomas—an ENITEC Group Initiative," Clin Cancer Res, 23(5):1274-1285.
Dickman et al., (2000). "Antifungal rapamycin analogues with reduced immunosuppressive activity," Bioorganic & Medicinal Chemistry Letters, 10(13):1405-1408.
Doi et al., (2010). "Multicenter phase II study of everolimus in patients with previously treated metastatic gastric cancer," J Clin Oncol, 28(11):1904-1910.
Durnov, L.A., et al., Pediatric Oncology, second edition, Moscow: "Meditsina" publishing house, 2002, p. 139, 5 pages, English translation.
Elnaggar et al., (2016). "Addition of Everolimus Post VEGFR Inhibition Treatment Failure in Advanced Sarcoma Patients Who Previously Benefited from VEGFR Inhibition: A Case Series," PLoS One, 11(6):e0156985, 7 pages.
Emsley et al., (2010). "Features and development of Coot," Acta Crystallographica Section D: Biological Crystallography, D66:486-501.

Fanoudi et al., (2018). "Everolimus, a mammalian target of rapamycin inhibitor, ameliorated streptozotocin—induced learning and memory deficits via neurochemical alterations in male rats," EXCLI J, 17:999-1017.
Ghidini et al., (2017). "Clinical development of mTor inhibitors for renal cancer," Expert Opin. Investig. Drugs, 26:1229-1237.
Guenther et al., (2009). "Phase I/II Study with Single Agent Everolimus (RAD001) in Patients with Relapsed or Refractory Multiple myeloma," Blood, 114(22):3850, 2 pages.
Gulhati et al., (2012). "Sorafenib enhances the therapeutic efficacy of rapamycin in colorectal cancers harboring oncogenic KRAS and PIK3CA," Carcinogenesis, 33(9):1782-1790.
Günther et al., (2015). "Activity of everolimus (RAD001) in relapsed and/or refractory multiple myeloma: a phase I study," Haematologica, 100(4):541-547.
Guo et al., (2016). "Everolimus exhibits anti-tumorigenic activity in obesity-induced ovarian cancer," Oncotarget, 7(15):20338-20356.
Hujber et al., (2017). "Rapamycin (mTORC1 inhibitor) reduces the production of lactate and 2-hydroxyglutarate oncometabolites in IDH1 mutant fibrosarcoma cells," J Exp Clin Cancer Res, 36(1):74, 12 pages.
International Search Report and Written Opinion received for International Patent Application No. PCT/IB2019/060957 mailed on Mar. 19, 2020, 10 pages.
International Search Report and Written Opinion received for International Patent Application No. PCT/IB2020/052825 mailed on May 28, 2020, 11 pages.
Johnston et al., (2018). "Phase 2 study of everolimus for relapsed or refractory classical Hodgkin lymphoma," Exp Hematol Oncol., 7:12, 10 pages.
Kabsch, (2010). "XDS," Acta Cryst. D, 66:125-132.
Kaeberlein et al., (2019). "Rapamycin and Alzheimer's disease: Time for a clinical trial?" Sci Transl Med, 11(476):aar4289, 10 pages.
Kang et al., (2021). "Impact of everolimus on survival after liver transplantation for hepatocellular carcinoma," Clin Mol Hepatol, 27(4):589-602.
Kummerer (2010). "Pharmaceuticals in the environment," Annual Review of Environment and Resources, 35:57-75, 22 pages.
Kwitkowski et al., (2010). "FDA Approval Summary: Temsirolimus as Treatment for Advanced Renal Cell Carcinoma," The Oncologist, 15(4):428-435.
Lin et al., (2017). "Rapamycin rescues vascular, metabolic and learning deficits in apolipoprotein E4 transgenic mice with pre-symptomatic Alzheimer's disease," J Cereb Blood Flow Metab, 37(1):217-226.
Luengo et al., (1995). "Structure-Activity Studies Of Rapamycin Analogs: Evidence That The C-7 Methoxy Group is Part of The Effector Domain and Positioned at The Fkbp12-Frap Interface," Chemistry and Biology, 2(7):471-481.
Mabuchi et al., (2009). "mTOR is a promising therapeutic target both in cisplatin-sensitive and cisplatin-resistant clear cell carcinoma of the ovary," Clin Cancer Res, 15(17):5404-5413, 21 pages.
Martin et al., (2012). "Effectiveness and molecular interactions of the clinically active mTORC1 inhibitor everolimus in combination with tamoxifen or letrozole in vitro and in vivo," Breast Cancer Res, 14(5):R132, 15 pages.
Mashkovsky "Medicines", 14th edition, vol. 1, Moscow, 2001, p. 11, 3 pages, English translation.
Miklja et al., (2020). "Everolimus improves the efficacy of dasatinib in PDGFRα-driven glioma," J Clin Invest, 130(10):5313-5325.
Miller et al., (2014). "Rapamycin-mediated lifespan increase in mice is dose and sex dependent and metabolically distinct from dietary restriction," Aging Cell, 13(3): 468-477.
Milowsky et al., (2013). "Phase II study of everolimus in metastatic urothelial cancer," BJU Int, 112(4):462-470.
Molinolo et al., (2012). "mTOR as a molecular target in HPV-associated oral and cervical squamous carcinomas," Clin Cancer Res, 18(9):2558-2568, 19 pages.
Moriya et al., (2014). "Antitumor effect and antiangiogenic potential of the mTOR inhibitor temsirolimus against malignant pleural mesothelioma," Oncol Rep, 31(3):1109-1115.

(56) References Cited

OTHER PUBLICATIONS

Murshudov et al., (2011). "REFMAC5 for the refinement of macromolecular crystal structures," Acta Crystallographica Section D: Biological Crystallography, 67(Pt 4):355-367.
Ozcelik et al., (2013). "Rapamycin attenuates the progression of tau pathology in P301S tau transgenic mice," PLoS One, 8(5):e62459, 7 pages.
Pinto-Leite et al., (2012). "Everolimus enhances gemcitabine-induced cytotoxicity in bladder-cancer cell lines," J Toxicol Environ Health A, 75(13-15):788-99. Abstract Only.
Poore et al., (2019). "Inhibition of mTORC1 in pediatric low-grade glioma depletes glutathione and therapeutically synergizes with carboplatin," Neuro Oncol, 21(2):252-263.
Ray-Coquard et al., (2013). "Everolimus as second- or third-line treatment of advanced endometrial cancer: ENDORAD, a phase II trial of GINECO," Br J Cancer, 108(9):1771-1777.
Shavlakadze et al., (2018). "Short-term Low-Dose mTORC1 Inhibition in Aged Rats Counter-Regulates Age-Related Gene Changes and Blocks Age-Related Kidney Pathology," J Gerontol A Biol Sci Med Sci., 73(7):845-852.
Silic-Benussi et al., (2022). "mTOR inhibition downregulates glucose-6-phosphate dehydrogenase and induces ROS-dependent death in T-cell acute lymphoblastic leukemia cells," Redox Biol, 51:102268, 14 pages.
Siman et al., (2015). "The mTOR Inhibitor Rapamycin Mitigates Perforant Pathway Neurodegeneration and Synapse Loss in a Mouse Model of Early-Stage Alzheimer-Type Tauopathy," PLoS One, 10(11):e0142340, 21 pages.
Spilman et al., (2011). "Inhibition of mTOR by rapamycin abolishes cognitive deficits and reduces amyloid-beta levels in a mouse model of Alzheimer's disease," PLoS One, 5(4):e9979, 8 pages.
Sun et al., (2012). "Chemopreventive and chemotherapeutic actions of mTOR inhibitor in genetically-defined head and neck squamous cell carcinoma mouse model," Clin Cancer Res, 18(19):5304-5313, 18 pages.
Vera Aguilera et al., (2018). "Phase II Study of Everolimus in Metastatic Malignant Melanoma (NCCTG-N0377, Alliance)," Oncologist, 23(8):887-e94, 6 pages.
Wolpin et al., (2013). "Multicenter phase II study of tivozanib (AV-951) and everolimus (RAD001) for patients with refractory, metastatic colorectal cancer," Oncologist, 18:377-378.
Yao et al., (2011). "Everolimus for advanced pancreatic neuroendocrine tumors," N Engl J Med, 364(6):514-523.
Yao et al., (2016). "Everolimus for the treatment of advanced, nonfunctional neuroendocrine tumours of the lung or gastrointestinal tract (RADIANT-4): a randomised, placebo-controlled, phase 3 study," Lancet, 387(10022):968-977, 20 pages.
Yi et al., (2020). "Safety and efficacy of sirolimus combined with endocrine therapy in patients with advanced hormone receptor—positive breast cancer and the exploration of biomarkers," Breast, 52:17-22.
Yoo et al., (2013). "Multicenter phase II study of everolimus in patients with metastatic or recurrent bone and soft-tissue sarcomas after failure of anthracycline and ifosfamide," Invest New Drugs, 31(6):1602-1608.
Yu et al., (2021). "Efficient Everolimus Treatment for Metastatic Castration Resistant Prostate Cancer with AKT1 Mutation: A Case Report," Onco Targets Ther, 14:5423-5428.
Zhu et al., (2011). "Phase 1/2 study of everolimus in advanced hepatocellular carcinoma," Cancer, 117(22):5094-5102.
Zureick et al., (2019). "Successful treatment of a TSC2-mutant glioblastoma with everolimus," BMJ Case Rep, 12(5):e227734, 4 pages.
Collaborative Computational Project, No. 4 (1994). "The CCP4 suite: programs for protein crystallography," Acta Crystallogr D Biol Crystallogr, 50(Pt 5):760-3.
Jiang et al., (2014). "Temsirolimus promotes autophagic clearance of amyloid-β and provides protective effects in cellular and animal models of Alzheimer's disease," Pharmacol Res, 81:54-63.
Luengo et al., (1994). "Manipulation of The Rapamycin Effector Domain. Selective Nucleophilic Substitution of The C7 Methoxy Group," Journal of Organic Chemistry, 59(22): 6512-6513.
Merli et al., (2015). "Everolimus in diffuse large B-cell lymphomas," Future Oncol, 11(3):373-83.
Nakagawa et al., (2013). "New immunosuppressive drug: mTOR inhibitor and thymoglobulin," Journal of the Japanese Society of Nephrology, 55(2):112-118. English translation.

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
gcttctaaaa ctggaatgac         20

```
<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gccactactc accgtctcct                                              20
```

RAPAMYCIN DERIVATIVES

CLAIM OF PRIORITY

This application is a continuation of U.S. patent application Ser. No. 17/004,434 filed 27 Aug. 2020, which is a continuation of U.S. patent application Ser. No. 16/141,856 filed 25 Sep. 2018, which claims priority to U.S. Patent Application No. 62/563,312 filed 26 Sep. 2017, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Apr. 14, 2022, is named 123841-5124_SL.txt and is 789 bytes in size.

FIELD

The invention provides 32-deoxo-rapamycin derivatives, and relates to their methods of use.

BACKGROUND

In mammalian cells, the target of rapamycin (mTOR) kinase exists in two distinct multiprotein complexes, described as the mTORC1 complex and the mTORC2 complex, both of which sense the availability of nutrients and energy, and integrate inputs from growth factors and stress signaling. The mTORC1 integrates signals from growth factors and nutrients and controls cell growth and metabolism. Laplante M. et al. Cell. (2012) 149(2):274-93. mTORC1 is a key regulator of protein translation and autophagy. The mTORC1 complex is sensitive to allosteric mTOR inhibitors such as rapamycin and rapamycin analogs (so called 'rapalogs'). Rapamycin and previously-produced rapalogs' mode of action involves the formation of an intracellular complex with FK506 binding proteins, either FKBP12, FKBP51 or FKBP52 (these three FKBPs will be referenced here as "FKBP" or "FKBPs"), followed by the binding of the FKBP-rapalog complex to the FRB (FK506-rapamycin binding) domain of mTOR. März A. M. et al. Mol Cell Biol. (2013) 33(7):1357-1367. Large FK506-Binding Proteins Shape the Pharmacology of Rapamycin Such interaction of the FKBP-rapalog complex with mTORC1 results in allosteric inhibition of the complex. Rapamycin and rapalogs, such as RAD001 (everolimus; Afinitor®), have gained clinical relevance by inhibiting the activity of mTORC1, which is associated with both benign and malignant proliferation disorders. Royce M. E. et al. Breast Cancer (Auckl). (2015) 9:73-79; Pleniceanu O. et al. Kidney Int Rep. (2018) 3(1):155-159.

Rapamycin is a known macrolide antibiotic produced by *Streptomyces hygoscopius*, see e.g. McAlpine, J. B., et al., J. Antibiotics (1991) 44:688; Schreiber, S. L.; et al., J. Am. Chem. Soc. (1991) 113:7433; U.S. Pat. No. 3,929,992. The following numbering convention for rapamycin and its derivatives used in this document is shown below:

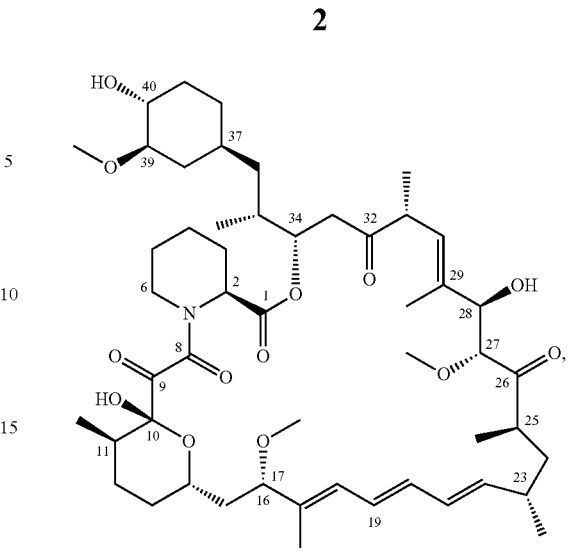

Rapamycin is a potent immunosuppressant and has also been shown to have antitumor and antifungal activity. It has been shown to be useful in preventing or treating systemic lupus erythematosus, pulmonary inflammation, insulin-dependent diabetes mellitus, skin disorders such as psoriasis, smooth muscle cell proliferation and intimal thickening following vascular injury, adult T-cell leukemia/lymphoma, malignant carcinomas, cardiac inflammatory disease, anemia and increased neurite outgrowth. Its utility as a pharmaceutical, however, is restricted by its very low and variable bioavailability. Moreover, Rapamycin is challenging to formulate, making it difficult to obtain stable galenic compositions.

To overcome these problems, numerous rapalogs have been (semi)synthesized. Water soluble prodrugs have been prepared by derivatizing rapamycin at C28 and 40 to form glycinate, propionate and pyrrolidino butyrate prodrugs (U.S. Pat. No. 4,650,803). Other analogs of rapamycin include monoacyl and diacyl analogs (U.S. Pat. No. 4,316,885), acetal analogs (U.S. Pat. No. 5,151,413) silyl ethers (U.S. Pat. No. 5,120,842), hydroxy esters (U.S. Pat. No. 5,362,718) as well as aryl, alkyl, alkenyl, and alkynyl analogs (U.S. Pat. Nos. 5,665,772; 5,258,389; 6,384,046; WO97/35575). Modifications to rapamycin include the demethylation, elimination or replacement of one or more of the methoxy groups; elimination, derivatization or replacement of one or more of the hydroxy moieties; reduction, elimination or derivatization of one or more of the ketone moieties; replacement of the 6-membered pipecolate ring with a 5-membered prolyl ring; alternative substitution on the cyclohexyl ring with a substituted cyclopentyl ring. Illustrative examples of the patent literature in this field are U.S. Pat. No. 5,527,907, WO96/41865 and WO99/36553 describing a wide variety of rapalogs with the aim to avoid the immunosuppressive side effects of rapamycin. U.S. Pat. No. 5,985,890 discloses examples of 32 deoxo-rapamycin analogs including 32-deoxo-rapamycin itself. It is described that these compounds have been reported to have an improved pharmacologic profile over rapamycin and greater stability.

The rapalogs described in the literature above have been disclosed to be useful for the treatment of the same disorders as rapamycin. U.S. Pat. Nos. 8,906,374 and 9,669,032 disclose the use in cancer. U.S. Pat. No. 9,358,236 discloses the use in neurodegenerative disorders.

In animal models, rapalogs extend lifespan and delay the onset of age-related diseases. Aging, like other biological processes, is regulated by signaling pathways such as the TOR pathway (named "TOR" in this case, to include the yeast and C. elegans systems, where the mammalian equivalent [mTOR] is simply called "TOR"]) and, in mammals, the mTORC1 pathway. Modulation of TOR and mTORC1 signaling prolongs lifespan and delays the onset of age-related diseases in a wide array of organisms, from flies to mammals. For instance, inhibition of the TOR pathway by genetic mutation extended lifespan in yeast, C. elegans, and drosophila, and inhibition of the mTORC1 pathway extended lifespan in mice (Kaeberlein et al., Science (2005) 310:1193-1196; Kapahi et al., Curr Biol (2004) 14:885-890; Selman et al., Science (2009) 326:140-144; Vellai et al., Nature (2003) 426:620). In addition, the mTORC1 inhibitor rapamycin extended the lifespan of mice even when given late in life (Harrison et al., Nature (2009) 460(7253):392-395). These data raise the possibility that drugs that target the mammalian TOR (mTOR) pathway will have therapeutic effects in aging and age-related diseases in humans. For instance, WO2008/022256 describes methods and topical formulations comprising an mTOR inhibitor for treating or preventing an age-related disease. A report of a clinical trial using rapamycin in elderly men was described by M. Leslie in Science, 2013, 342. J. Mannick et al. describe in Sci Transl Med. (2014) 6(268): 268ra179 that mTOR inhibition improves the immune function in the elderly. However, investigators have been wary of using currently available mTOR inhibitors in human aging trials due to their side effects (including immunosuppression, cytopenias, stomatitis, GI distress and interstitial pneumonitis).

In animal and human studies of Focal Cortical Dysplasia (FCD) and Tuberous Sclerosis Complex (TSC), the mTOR pathway is implicated in mediating the cellular and molecular changes leading to the formation of the cortical malformations and the expression of epilepsy (Wong et al., Experimental Neurology (2013) 244: 22-26). Focal Cortical Dysplasia (FCD) is a malformation of cortical development, which is the most common cause of refractory epilepsy in the pediatric population and the second/third most common etiology of medically intractable seizures in adults (Kabat J, et al., Pot J. Radiology (2012) 77(2) 35-43). Mutations in the tuberous sclerosis complex (TSC), including tuberous sclerosis complex-1 (TSC1) and tuberous sclerosis complex-2 (TSC2), act upstream of the mTOR pathway, leading to a wide spread development of benign tumors, mental retardation, and a high incidence of epilepsy (Manning et al., Identification of the tuberous sclerosis complex-2 tumor suppressor gene product tuberin as a target of the phosphoinositide 3-kinase/akt pathway, Mol. Cell, (2002) 10: 151-162; Inoki et al., Dysregulation of the TSC-mTOR pathway in human Disease, Nat. Genet, (2005), 37:19-24; and Holmes and Stafstrom, Tuberous sclerosis complex and epilepsy: recent developments and future Challenges, Epilepsia, (2007) 48:617-630).

Aberrant mTOR activation interferes with normal brain development and leads to epilepsy. Rapamycin treatment, which inhibits the mTORC1 pathway, is shown to attenuate structural abnormalities and reduce seizures in TSC and PTEN mouse models (Ehninger et al., Reversal of learning deficits in a Tsc2+/− mouse model of tuberous sclerosis; Nat. Med., (2008), 843-848; Meikle et al., Response of a neuronal model of tuberous sclerosis to mammalian target of rapamycin, mTOR inhibitors: effects on mTORC1 and Akt signaling lead to improved survival and function; J. Neuroscience, (2008) 28:5422-5432; Zeng et al., Rapamycin prevents epilepsy in a mouse model of tuberous sclerosis complex; Ann. Neurol., (2008) 63:444-453; Ljungberg et al., Rapamycin suppresses seizures and neuronal hypertrophy in a mouse model of cortical dysplasia; (2009) pp. 389-398; and Zhou et al., Pharmacological inhibition of mTORC1 suppresses anatomical, cellular, and behavioral abnormalities in neural-specific Pten knock-out mice, J. Neurosci., (2009), 29:1773-1783). Further, pharmacological inhibition of the mTOR pathway, either before or immediately following neurological insults, can prevent pathological changes in animal brains and the development of spontaneous recurrent seizure in an acquired epilepsy model (Zeng et al., The mammalian target of rapamycin signaling pathway mediates epileptogenesis in a model of temporal lobe epilepsy; J. Neurosci., (2009) pp. 6964-6972). Rapamycin and rapalogs are therefore also considered to be of potential value in such indications.

Mitochondrial myopathy (MM) is the most common manifestation of adult-onset mitochondrial disease and shows a multifaceted tissue-specific stress response: (1) transcriptional response, including metabolic cytokines FGF21 and GDF15; (2) remodeling of one-carbon metabolism; and (3) the mitochondrial unfolded protein response. In Cell Metabolism 26, 419-428, Aug. 1, 2017, it is described by Khan et al. that these processes are part of one integrated mitochondrial stress response (ISRmt), which is controlled by mTORC1 in skeletal muscle. A mtDNA replication defect activates mTORC1, which drives an integrated mitochondrial stress response through ATF4 activation, inducing de novo nucleotide and serine synthesis, the 1C-cycle, and FGF21 and GDF15 production. mTORC1 inhibition by rapamycin downregulated all components of ISRmt (the integrated mitochondrial stress response), improved all MM hallmarks, and reversed the progression of even late-stage MM, without inducing mitochondrial biogenesis. Rapamycin and rapalogs are therefore also considered to be of potential value in such indications.

There remains a need to provide new mTOR inhibitors that are good drug candidates. In particular, preferred compounds should have at least mTORC1 inhibitory capacity, and be well absorbed from the gastrointestinal tract, be sufficiently metabolically stable and possess favorable pharmacokinetic properties. Furthermore, the ideal drug candidate will be able to exist in a physical form that is stable, non-hygroscopic and appropriate for formulation.

SUMMARY

The compounds of structural formula (I) are mTORC1 inhibitors and are therefore potentially useful in the treatment of a wide range of disorders, particularly age-related disorders, or diseases and disorders currently approved for treatment using rapalogs. Full reduction of the ketone at C32 and the replacement of the C16 methoxy group by a cyclic N-containing aliphatic ring system, such as a cyclic amine, amide or sultam, provides compounds with the above-mentioned desired advantages, exhibiting a balance of good potency, stability and bioavailability.

In one aspect, the disclosure provides compounds of the structural formula (I):

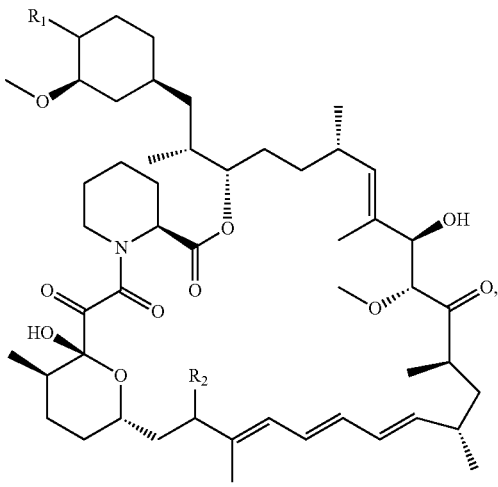 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

or a pharmaceutically acceptable salt thereof, wherein
$R_1$ is selected from the group consisting of hydroxy,

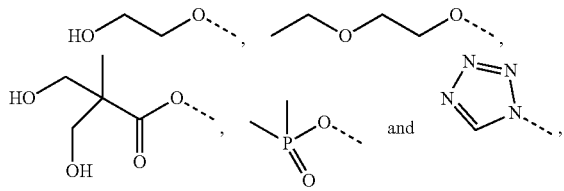

and
$R_2$ is selected from the group consisting of

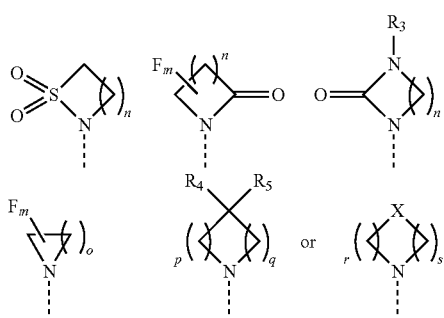

wherein
m is 0, 1, 2 or 3;
n is 1, 2 or 3;
is 1, 2, 3, 4, 5 or 6;
p is 1, 2, 3, 4 or 5
q is 1, 2, 3, 4 or 5 wherein the sum of p and q is 2, 3, 4, 5 or 6;
r is 2, 3 or 4;
s is 2, 3 or 4 wherein the sum of r and s is 4, 5 or 6;
X is O, S, $NR_6$ or $SO_2$;
$R_3$ is hydrogen, $C_{1-6}$alkyl, hydroxy$C_{1-6}$alkyl, $C_{3-8}$cycloalkyl$C_{0-6}$alkyl or phenyl$C_{0-6}$alkyl;
$R_4$ is hydrogen;
$R_5$ is hydrogen, hydroxy or cyano; or $R_4$ and $R_5$ together form =O; and
$R_6$ is hydrogen, $C_{1-6}$alkyl, $C_{3-8}$cycloalkyl$C_{0-6}$alkyl, phenyl$C_{0-6}$alkyl, $C_{1-6}$alkyl-CO—, $C_{3-8}$cycloalkyl$C_{0-6}$alkyl-CO—, $C_{1-6}$alkyl-$SO_2$— or $C_{3-8}$cycloalkyl$C_{0-6}$alkyl-$SO_2$—.

In an embodiment, the disclosure provides a pharmaceutical composition comprising a therapeutically effective amount of a compound of structural formula (I) or a pharmaceutically acceptable salt thereof and one or more pharmaceutically acceptable carriers.

In an embodiment, the disclosure provides a pharmaceutical combination comprising a therapeutically effective amount of a compound of structural formula (I) or a pharmaceutically acceptable salt thereof and one or more therapeutically active agents.

In another aspect, the disclosure provides a method of treating a disorder or a disease mediated by the mTOR pathway in a subject in need thereof, the method comprising administering to the subject a therapeutically effective amount of a compound of structural formula (I), or a pharmaceutical composition, or a pharmaceutical combination thereof. In another aspect, the disclosure provides a method of treating a disease or disorder in a subject, wherein the target tissue or organ associated with the pathology of the disease or disorder has FKBP12 levels sufficient to inhibit mTORC1, the method comprising administering to the subject in need thereof a therapeutically effective amount of a compound of structural formula (I) or a pharmaceutically acceptable salt thereof, or a pharmaceutical composition, or a pharmaceutical combination thereof.

In an embodiment, the target tissue or organ associated with the pathology of the disease or disorder to be treated with a compound of structural formula (I) has FKBP12 levels sufficient to inhibit mTORC1 are determined empirically, e.g., using an FKBP12-specific inhibitor in comparison to rapamycin or RAD001.

In another aspect, the disclosure provides a method of treating a disease or disorder in a subject having, or previously determined as having, FKBP12 levels sufficient to inhibit mTORC1, the method comprising administering to the subject in need thereof a therapeutically effective amount of a compound of structural formula (I) or a pharmaceutically acceptable salt thereof, or a pharmaceutical composition thereof, or a pharmaceutical combination thereof.

In an embodiment, the subject has, or is previously determined to have, FKBP12 levels in the target tissue, organ or cells sufficient to inhibit mTORC1.

In another aspect, the disclosure provides a method of treating an age-related disease or disorder in a subject in need thereof, the method comprising administering to the subject a therapeutically effective amount of a compound of structural formula (I) or a pharmaceutically acceptable salt thereof, or a pharmaceutical composition, or a combination thereof, In an embodiment, the disease or disorder is selected from sarcopenia, skin atrophy, cherry angiomas, seborrheic keratoses, brain atrophy—also referred to as dementia, atherosclerosis, arteriosclerosis, pulmonary emphysema, osteoporosis, osteoarthritis, high blood pressure, erectile dysfunction, cataracts, macular degeneration, glaucoma, stroke, cerebrovascular disease (strokes), chronic kidney disease, diabetes-associated kidney disease, impaired hepatic function, liver fibrosis, autoimmune hepatitis, endometrial hyperplasia, metabolic dysfunction, renovascular disease, hearing loss, mobility disability (e.g., frailty), cognitive decline, tendon stiffness, heart dysfunction such as cardiac hypertrophy and/or systolic and/or diastolic dysfunction and/or hypertension, heart dysfunction which results in a decline in ejection fraction, immune senescence, Parkinson's disease, Alzheimer's disease, cancer, immune-senescence leading to cancer due to a decrease in immune-surveillance, infections due to an decline in immune-function, chronic obstructive pulmonary disease (COPD), obesity, loss of taste, loss of olfaction, arthritis, and type II diabetes including complications stemming from diabetes, such as kidney failure, blindness and neuropathy.

In another aspect, the disclosure provides a method of treating a disease or disorder in a subject in need thereof, the method comprising administering to the subject a therapeutically effective amount of a compound of structural formula (I) or a pharmaceutically acceptable salt thereof, or a pharmaceutical composition, or a pharmaceutical combination thereof, wherein the disorder or disease is selected from:

Acute or chronic organ or tissue transplant rejection;
Transplant vasculopathies;
Smooth muscle cell proliferation and migration leading to vessel intimal thickening, blood vessel obstruction, obstructive coronary atherosclerosis, restenosis;
Autoimmune diseases and inflammatory conditions;
Treatment and prevention of asthma;
Multi-drug resistance (MDR);
Fungal infections;
Inflammation;
Infection;
Age-related diseases;
Neurodegenerative diseases;
Proliferative disorders, in particular cancer;
Seizures and seizure related disorders; and
Mitochondrial myopathy and mitochondrial stress.

In another aspect, the disclosure provides a method of treating cancer in a subject in need thereof, the method comprising administering to the subject a therapeutically effective amount of a compound of structural formula (I) or a pharmaceutically acceptable salt thereof, or a pharmaceutical composition, or a pharmaceutical combination thereof.

In an embodiment, the method further comprises a PD-1/PDL-1 inhibitor.

In an embodiment, the cancer is selected from renal cancer, renal cell carcinoma, colorectal cancer, uterine sarcoma, endometrial uterine cancer, endometrial cancer, breast cancer, ovarian cancer, cervical cancer, gastric cancer, fibrosarcoma, pancreatic cancer, liver cancer, melanoma, leukemia, multiple myeloma, nasopharyngeal cancer, prostate cancer, lung cancer, glioblastoma, bladder cancer, mesothelioma, head cancer, rhabdomyosarcoma, sarcoma, lymphoma, and neck cancer.

In an embodiment, the disorder is a liver disorder that includes the process of fibrosis and/or inflammation, e.g., liver fibrosis that occurs in end-stage liver disease; liver cirrhosis; liver failure due to toxicity; non-alcohol-associated hepatic steatosis or NASH; and alcohol-associated steatosis.

In an embodiment, the disorder is a kidney disorder that includes the process of fibrosis or inflammation in the kidney, e.g., kidney fibrosis, which occurs as a result of acute kidney injury, leading to chronic kidney disease and diabetic nephropathy.

In an embodiment, the disorder is a heart dysfunction, e.g., myocardial infarction or cardiac hypertrophy. In an embodiment, the heart dysfunction is systolic and/or diastolic dysfunction. In an embodiment, the heart dysfunction is hypertension. In an embodiment, the heart dysfunction results in a decline in ejection fraction.

In an embodiment, the disorder is an immune-senescence leading to cancer due to a decrease in immune-surveillance.

In an embodiment, the disorder is cancer, including tumors which are treated by immunotherapy, and those which have been previously treated by either rapamycin, or Everolimus or another rapalog. In an embodiment, the cancer includes tumors where the mTOR pathway is shown to be activated, including settings where there is a mutation in the Tsc1 gene, or where the tumor microenvironment is appropriately treated by a rapalog.

The details of one or more embodiments of the disclosure are set forth herein. Other features, objects, and advantages of the disclosure will be apparent from the Figures, the Detailed Description, the Examples, and the Claims.

DETAILED DESCRIPTION

Figure 1A:
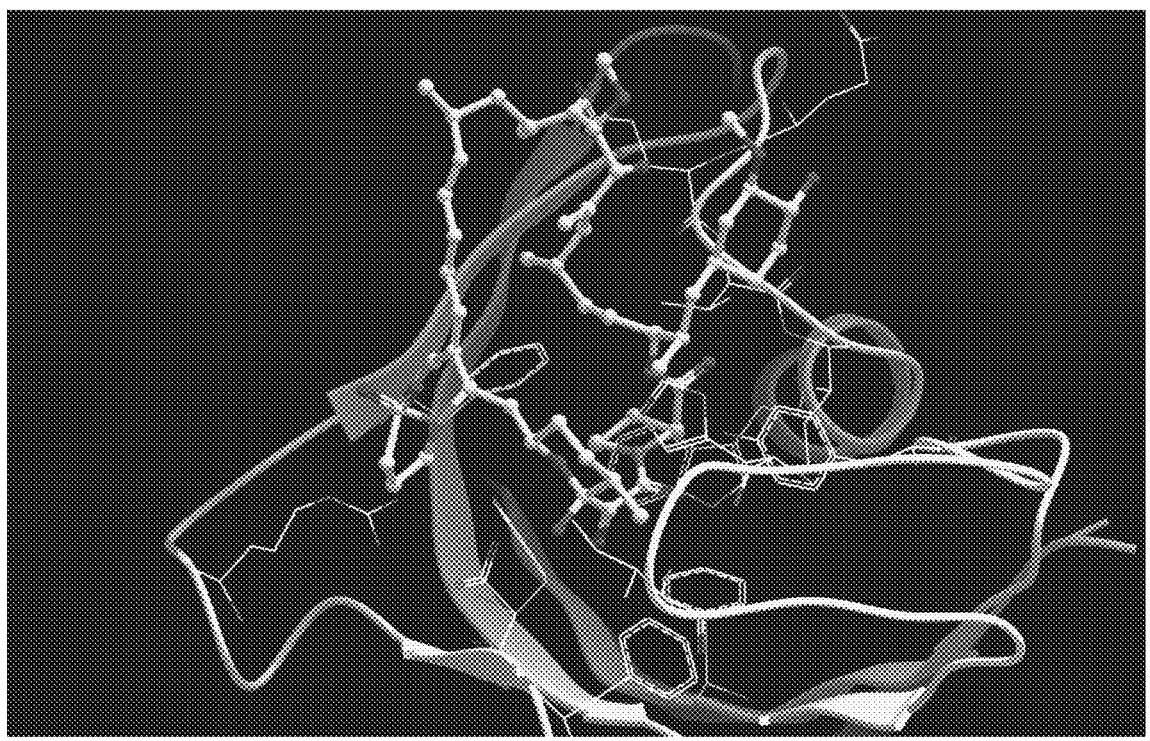
FIG. 1A is an image of a co-crystal structure of Example 1 with FKBP12. The absolute configuration at C16 is (S).
Figure 1B:
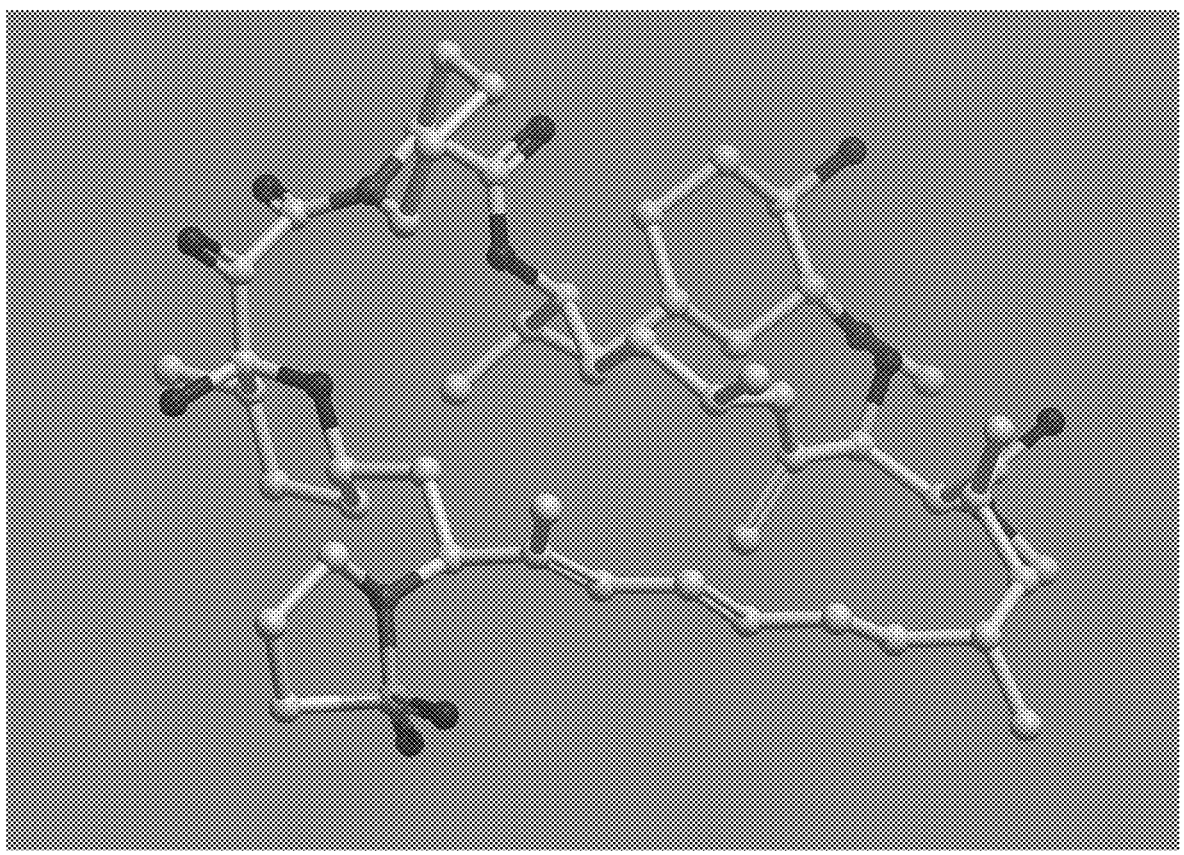
FIG. 1B shows the structure of Example 1 with the FKBP12 protein removed.
Figure 2A:
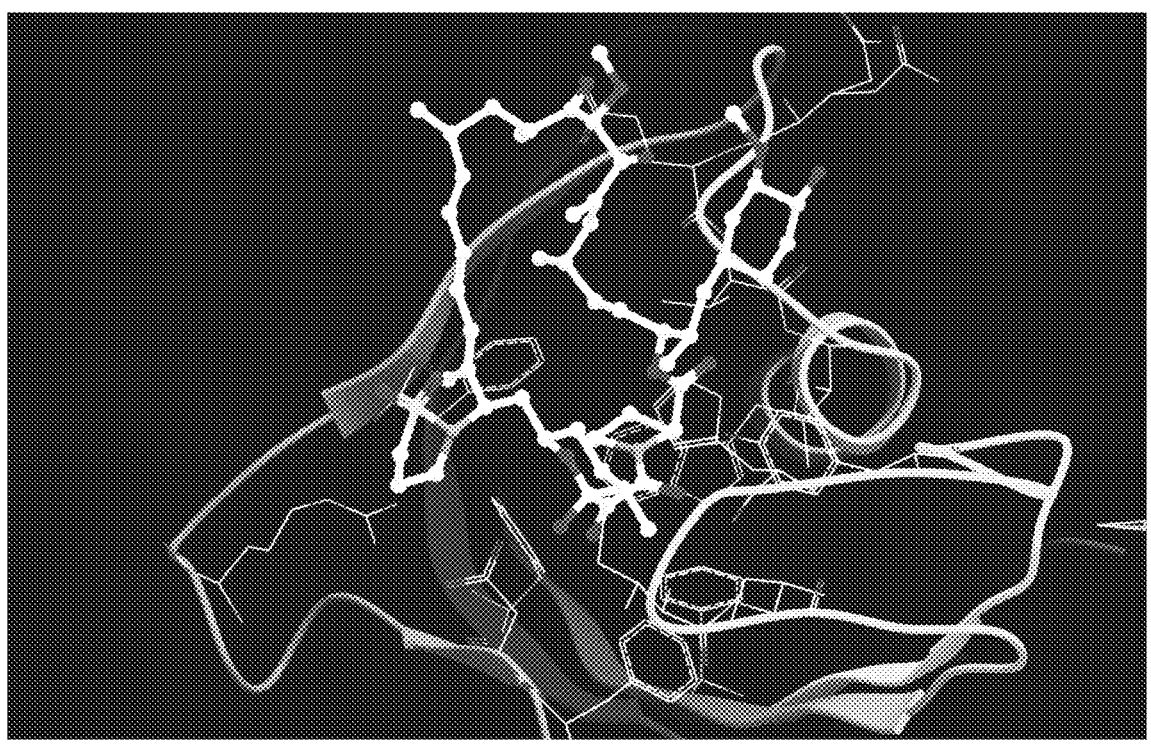
FIG. 2A is an image of a co-crystal structure of Example 2 with FKBP12. The absolute configuration at C16 is (R).
Figure 2B:
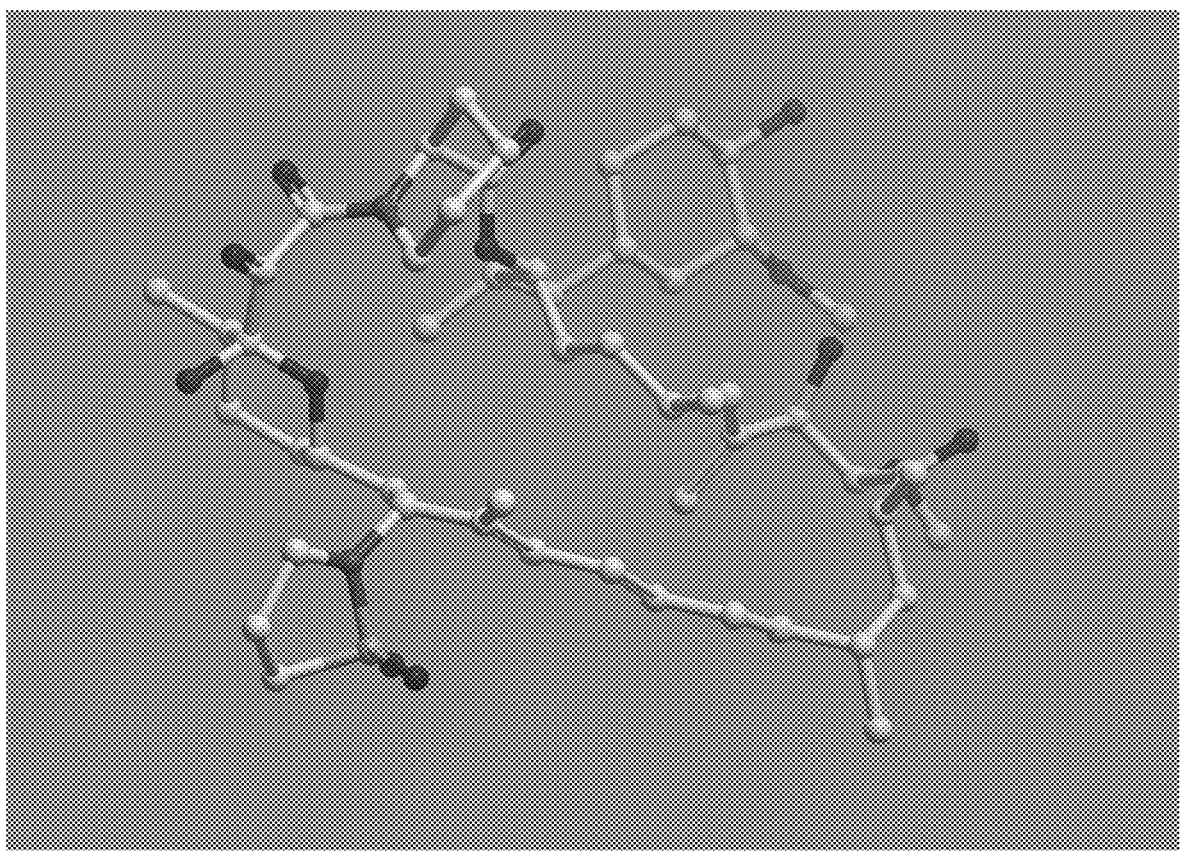
FIG. 2B shows the structure of Example 2 with the FKBP12 protein removed.

In a first aspect, the disclosure provides a compound of the formula (I)

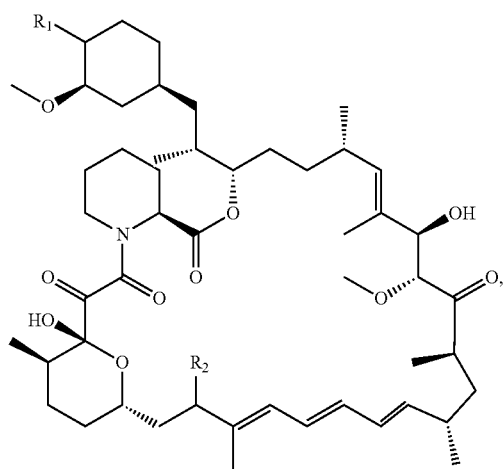

(I)

or a pharmaceutically acceptable salt thereof, wherein
$R_1$ is selected from the group consisting of hydroxy,

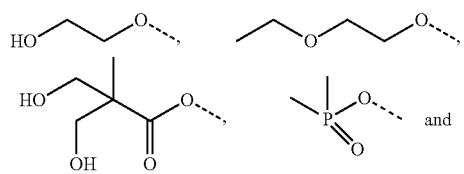

and
$R_2$ is selected from the group consisting of

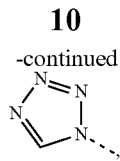

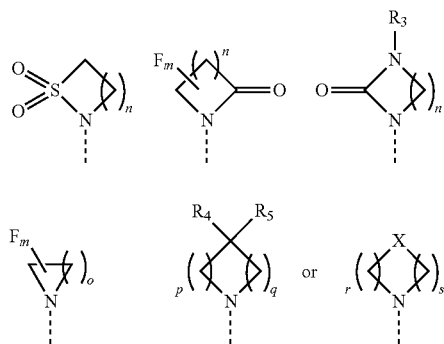

wherein
m is 0, 1, 2 or 3;
n is 1, 2 or 3;
is 1, 2, 3, 4, 5 or 6;
p is 1, 2, 3, 4 or 5
q is 1, 2, 3, 4 or 5 wherein the sum of p and q is 2, 3, 4, 5 or 6;
r is 2, 3 or 4;
s is 2, 3 or 4 wherein the sum of r and s is 4, 5 or 6;
X is O, S, $NR_6$ or $SO_2$;
$R_3$ is hydrogen, $C_{1-6}$alkyl, hydroxy$C_{1-6}$alkyl, $C_{3-8}$cycloalkyl$C_{0-6}$alkyl or phenyl$C_{0-6}$alkyl;
$R_4$ is hydrogen;
$R_5$ is hydrogen, hydroxy or cyano; or $R_4$ and $R_5$ together form =O; and
$R_6$ is hydrogen, $C_{1-6}$alkyl, $C_{3-8}$cycloalkyl$C_{0-6}$alkyl, phenyl$C_{0-6}$alkyl, $C_{1-6}$alkyl-CO—, $C_{3-8}$cycloalkyl$C_{0-6}$alkyl-CO—, $C_{1-6}$alkyl-$SO_2$— or $C_{3-8}$cycloalkyl$C_{0-6}$alkyl-$SO_2$—.

In an embodiment, the disclosure provides a compound of the formula (I)

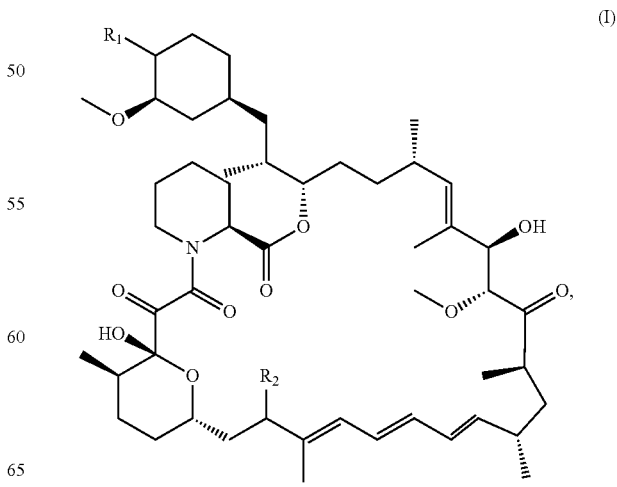

(I)

or a pharmaceutically acceptable salt thereof, wherein
R₁ is selected from the group consisting of hydroxy,

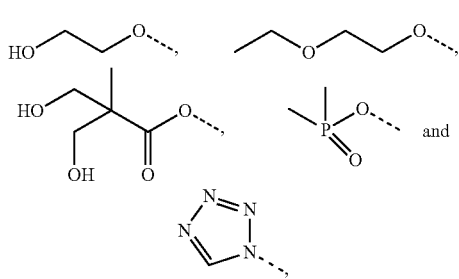

and
R₂ is selected from the group consisting of

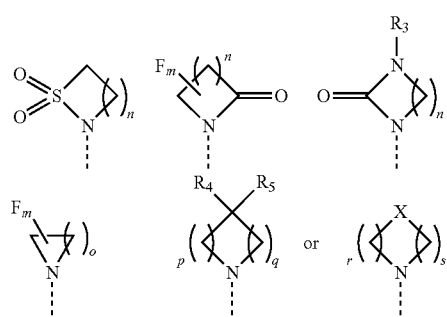

wherein
m is 0, 1, 2 or 3;
n is 1, 2 or 3;
is 1, 2, 3, 4, 5 or 6;
p is 1, 2, 3, 4 or 5
q is 1, 2, 3, 4 or 5 wherein the sum of p and q is 2, 3, 4, 5 or 6;
r is 2, 3 or 4;
s is 2, 3 or 4 wherein the sum of r and s is 4, 5 or 6;
X is O, S, NR₆ or SO₂;
R₃ is hydrogen, C₁₋₆alkyl, C₃₋₈cycloalkylC₀₋₆alkyl or phenylC₀₋₆alkyl;
R₄ is hydrogen;
R₅ is hydrogen, hydroxy or cyano; or R₄ and R₅ together form =O; and
R₆ is hydrogen, C₁₋₆alkyl, C₃₋₈cycloalkylC₀₋₆alkyl, phenylC₀₋₆alkyl, C₁₋₆alkyl-CO—, C₃₋₈cycloalkylC₀₋₆alkyl-CO—, C₁₋₆alkyl-SO₂— or C₃₋₈cycloalkylC₀₋₆alkyl-SO₂—.

Definitions

Unless specified otherwise, the term "compounds of the disclosure" or "compound of the disclosure" refers to compounds of formula (I), and exemplified compounds, and salts thereof, as well as all stereoisomers (including diastereoisomers and enantiomers), rotamers, tautomers and isotopically labeled compounds (including deuterium substitutions), as well as inherently formed moieties.

As used herein, " ------ " represents a portion of a variable bound to the base molecule and includes both (R)- and (S)-stereochemistry. For example, when R² is

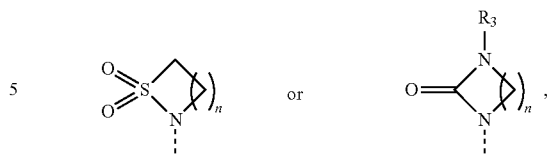

" ------ " represents the portion of R₂ bound to C16 and includes both (R)- and (S)-stereochemistry.

As used herein, the term "C₁₋₆alkyl" refers to a straight or branched hydrocarbon chain radical consisting solely of carbon and hydrogen atoms, containing no unsaturation, having from one to six carbon atoms, and which is attached to the rest of the molecule by a single bond. The term "C₁₋₄alkyl" is to be construed accordingly. Examples of C₁₋₆alkyl include, but are not limited to, methyl, ethyl, n-propyl, 1-methylethyl (iso-propyl), n-butyl, n-pentyl and 1,1-dimethylethyl (t-butyl).

As used herein, the term "hydroxyC₁₋₆alkyl" refers to an alkyl group substituted with one or more —OH groups. Examples of hydroxyC₁₋₆alkyl groups include HO—CH₂—, HO—CH₂CH₂—, and —CH₂—CH(OH)—.

As used herein, the term "C₃₋₈cycloalkylC₀₋₆alkyl" refers to a stable monocyclic saturated hydrocarbon radical consisting solely of carbon and hydrogen atoms, having from three to eight carbon atoms, and which is attached to the rest of the molecule by a single bond or by a C₁₋₆alkyl radical as defined above. Examples of C₃₋₈cycloalkylC₀₋₆alkyl include, but are not limited to, cyclopropyl, cyclopropyl-methyl, cyclobutyl, cyclobutyl-ethyl, cyclopentyl, cyclopentyl-propyl, cyclohexyl, cyclohepty and cyclooctyl.

As used herein, the term "phenylC₀₋₆alkyl" refers to a phenyl ring attached to the rest of the molecule by a single bond or by a C₁₋₆alkyl radical as defined above. Examples of phenylC₀₋₆alkyl include, but are not limited to, phenyl and benzyl.

As used herein, "hydroxy" or "hydroxyl" refers to —OH.

Various (enumerated) embodiments of the disclosure are described herein. It will be recognized that features specified in each embodiment may be combined with other specified features to provide further embodiments of the disclosure.

Embodiment 1. A compound of formula (I) or a pharmaceutically acceptable salt thereof, as described above.

Embodiment 2. A compound according to embodiment 1 or a pharmaceutically acceptable salt thereof, wherein R₁ is hydroxy.

Embodiment 3. A compound according to embodiment 1 or 2 or a pharmaceutically acceptable salt thereof, wherein R₂ is selected from

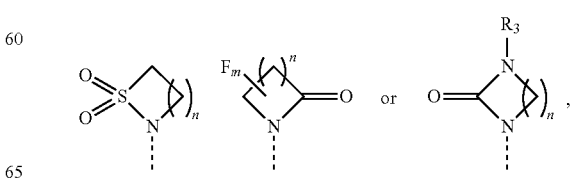

in particular

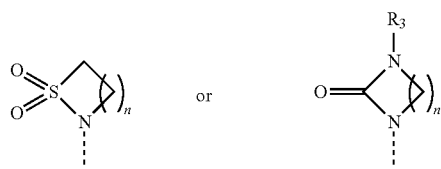

wherein m, n, X and $R_3$ are as defined above.

Embodiment 4. A compound according to any one of embodiments 1 to 3 or a pharmaceutically acceptable salt thereof, wherein $R_2$ is

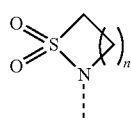

and n is 1, 2 or 3. In an embodiment, $R_2$ is

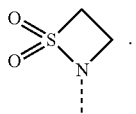

Embodiment 5. A compound according to any one of embodiments 1 to 4, or a pharmaceutically acceptable salt thereof, wherein $R_2$ is

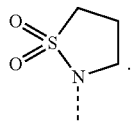

Embodiment 6. A compound according to any one of embodiments 1 to 4 or a pharmaceutically acceptable salt thereof, wherein $R_2$ is

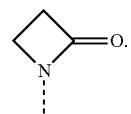

Embodiment 7. A compound according to any one of embodiments 1 to 4 or a pharmaceutically acceptable salt thereof, wherein $R_2$ is

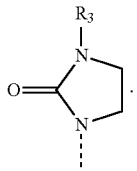

In an embodiment, $R_3$ is hydrogen, $C_{1-6}$alkyl or hydroxy-$C_{1-6}$alkyl.

Embodiment 8. A compound according any one of embodiments 1 to 5 of formula (I)-A:

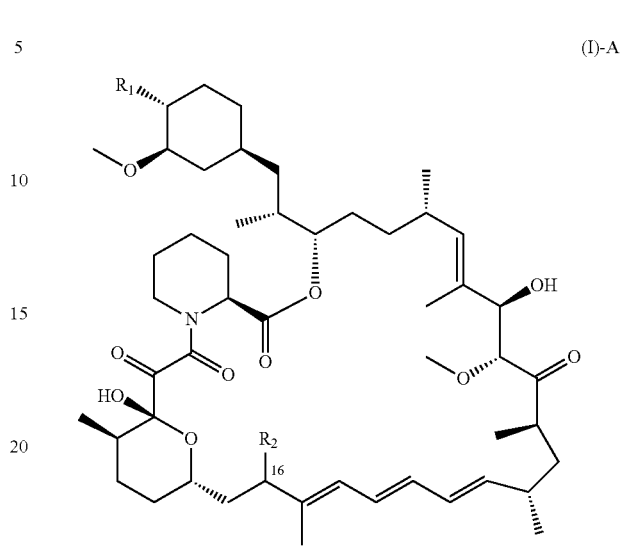

(I)-A or a pharmaceutically acceptable salt thereof, wherein $R_1$ is selected from the group consisting of hydroxy,

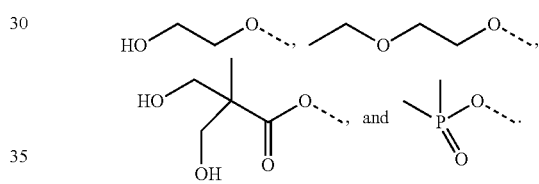

In an embodiment, $R_1$ is hydroxyl. In an embodiment, $R_2$ is as defined in formula (I). In an embodiment, the C16 position has (R) stereochemistry. In an embodiment, the C16 position has (S) stereochemistry.

Embodiment 9. A compound according to any one of embodiments 1 to 8 or a pharmaceutically acceptable salt thereof, wherein said compound is C16-(1,1-dioxidoisothiazolidin-2-yl)-C32-deoxo-rapamycin (Compound 1):

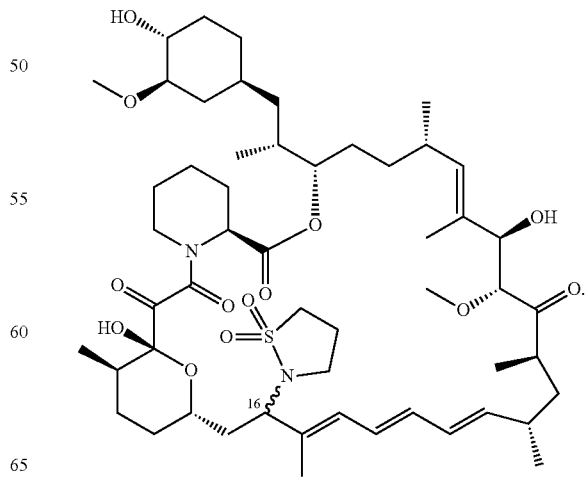

Embodiment 10. A compound according to any one of embodiments 1 to 9 or a pharmaceutically acceptable salt thereof, present as a single diastereoisomer at C16. In an embodiment, the C16 position has (R) stereochemistry. In an embodiment, the C16 position has (S) stereochemistry.

Embodiment 11. A compound according to any one of embodiments 1 to 9 or a pharmaceutically acceptable salt thereof, present as a diastereoisomeric mixture at C16.

Embodiment 12. A compound according to any one of embodiments 1 to 10 of formula (I)-B,

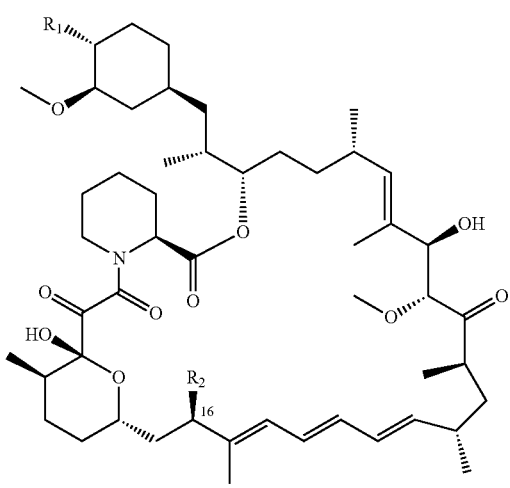

(I)-B or a pharmaceutically acceptable salt thereof, wherein $R_1$ and $R_2$ are as defined for formula (I). In an embodiment, $R_2$ is

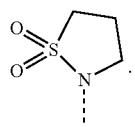

Embodiment 13. A compound of formula (I) or a pharmaceutically acceptable salt thereof, wherein said compound is (S)—C16-(1,1-dioxidoisothiazolidin-2-yl)-C32-deoxo-rapamycin (Example 1):

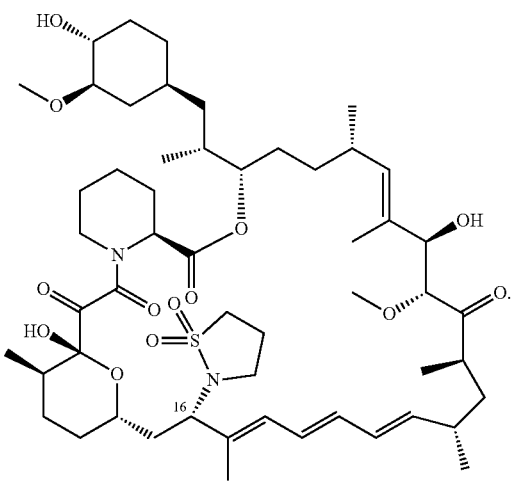 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](N3CCCS3(=O)=O)C[C@@H]3CC[C@@H](C)[C@@](O)(O3)C(=O)C(=O)N3CCCC[C@H]3C(=O)O2)CC[C@H]1O]

Embodiment 14. A compound of formula (I) or a pharmaceutically acceptable salt thereof, wherein said compound is (R)—C16-(1,1-dioxidoisothiazolidin-2-yl)-C32-deoxo-rapamycin (Example 2):

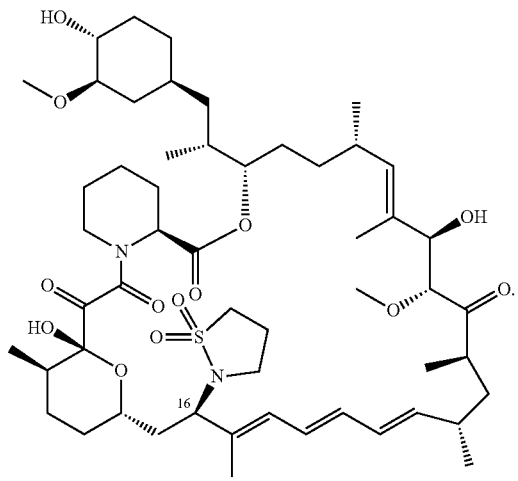 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](N3CCCS3(=O)=O)C[C@@H]3CC[C@@H](C)[C@@](O)(O3)C(=O)C(=O)N3CCCC[C@H]3C(=O)O2)CC[C@H]1O]

Embodiment 15: A compound of formula (I) or a pharmaceutically acceptable salt thereof, wherein said compound is selected from:

| Compound | Structure |
|---|---|
| Example 3 | 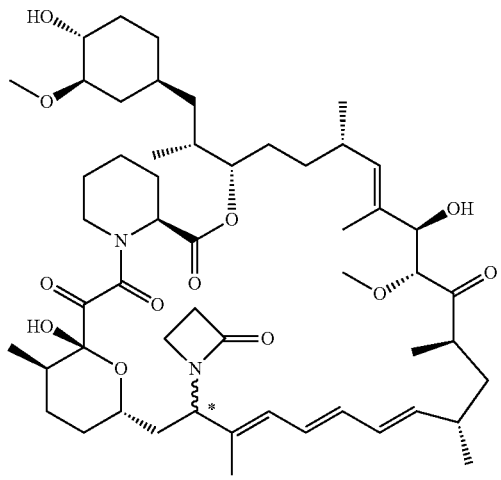<br>*Absolute sterochemistry at C16 not assigned |
| Example 4 | 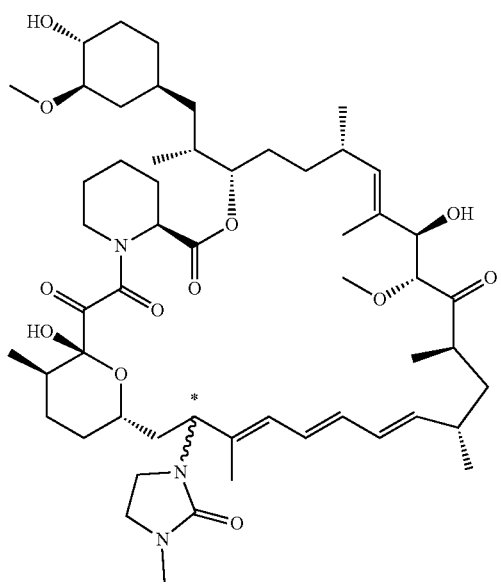<br>*Absolute sterochemistry at C16 not assigned |

| Compound | Structure |
|---|---|
| Example 5 | 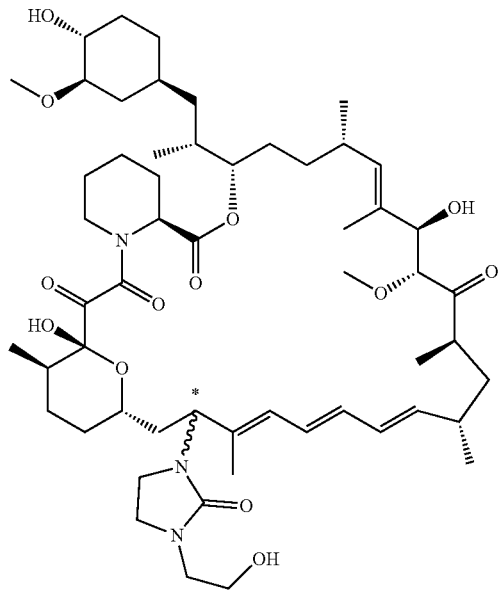<br>*Absolute sterochemistry at C16 not assigned |
| Example 6<br>Example 7<br>diastereomers<br>at C16 | 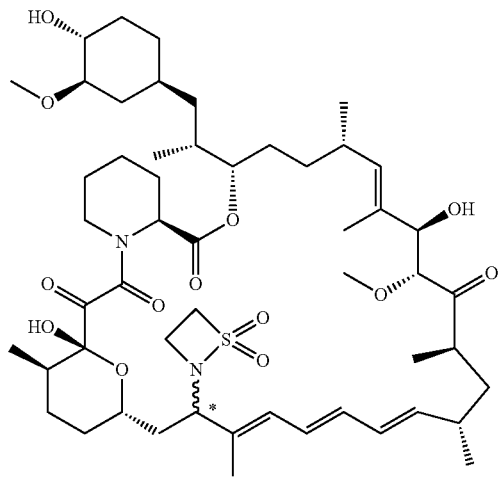<br>*Absolute sterochemistry at C16 not assigned |

| Compound | Structure |
|---|---|
| Example 8<br>Example 9<br>diastereomers<br>at C16 | 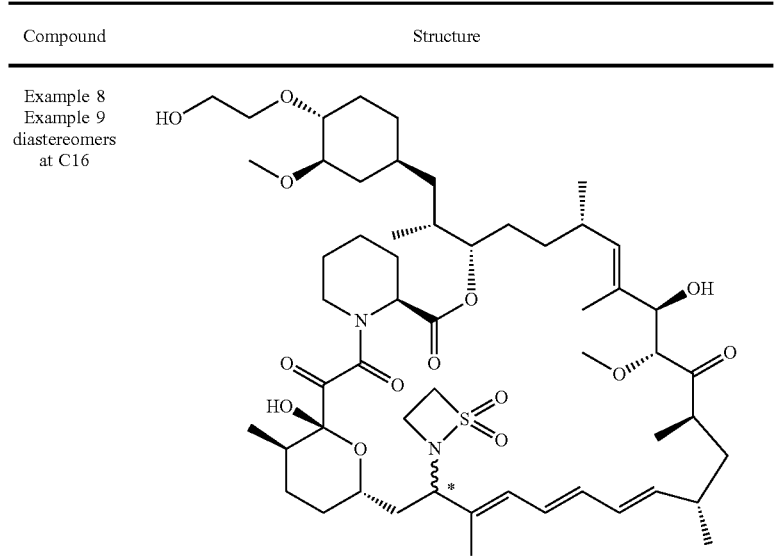<br>*Absolute sterochemistry at C16 not assigned |
| Example 10<br>Example 11<br>diastereomers<br>at C16 | 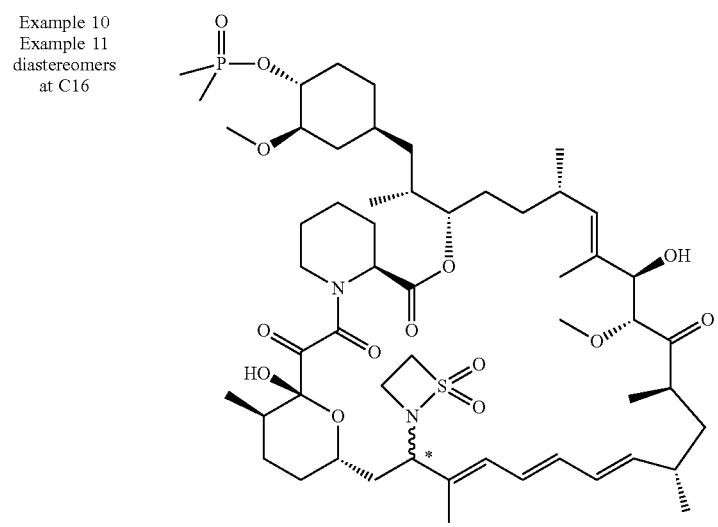<br>*Absolute sterochemistry at C16 not assigned |

| Compound | Structure |
|---|---|
| Example 12<br>Example 13<br>Single diastereomer at C16 | 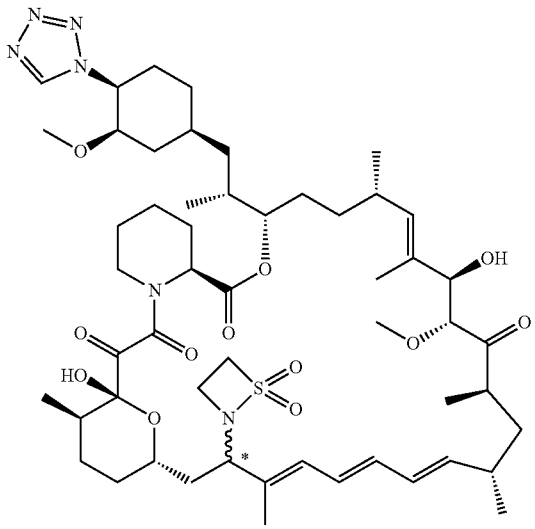<br>*Absolute sterochemistry at C16 not assigned |
| Example 14<br>Example 15<br>diastereomers at C16 | 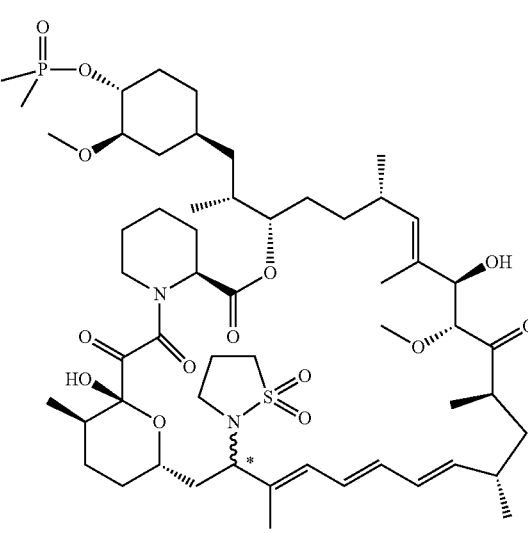<br>*Absolute sterochemistry at C16 not assigned |
| Example 16 | 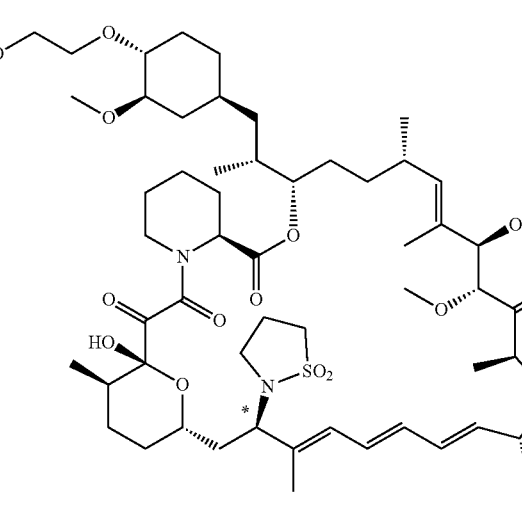 |

| Compound | Structure |
|---|---|
| Example 17 | 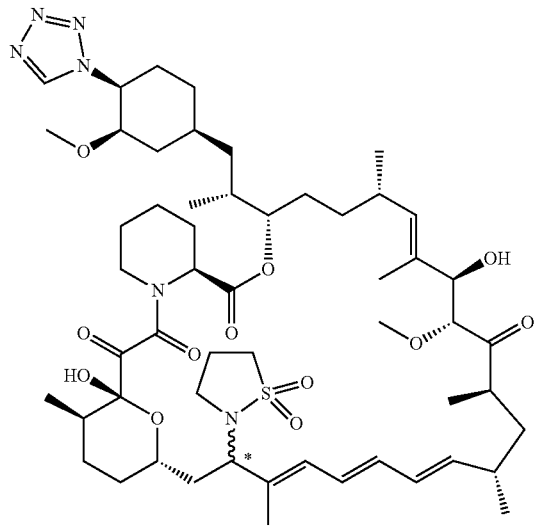
*Absolute sterochemistry at C16 not assigned |
| Example 18 | 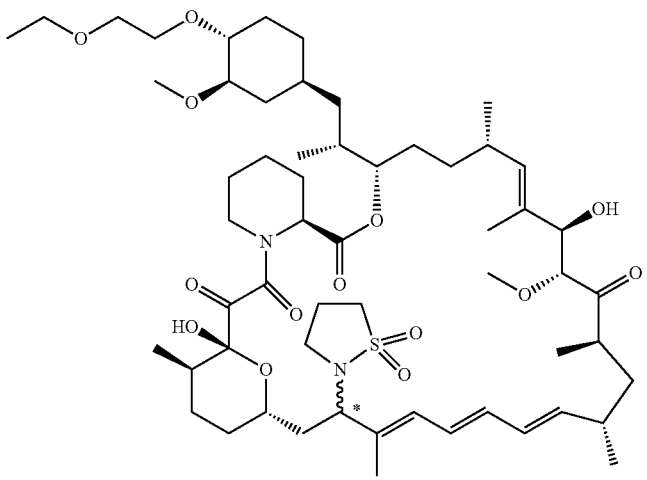
*Absolute sterochemistry at C16 not assigned |

| Compound | Structure |
|---|---|
| Example 19 | 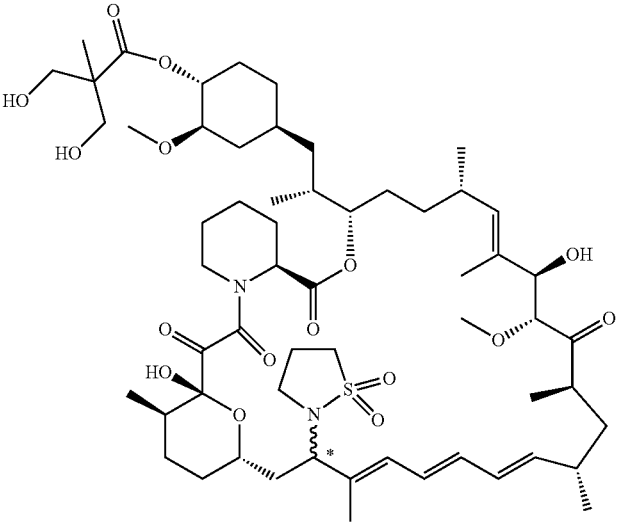 |

*Absolute sterochemistry at C16 not assigned

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Thomas Sorrell, Organic Chemistry, University Science Books, Sausalito, 1999; Smith and March, March's Advanced Organic Chemistry, 5$^{th}$ Edition, John Wiley & Sons, Inc., New York, 2001; Larock, Comprehensive Organic Transformations, VCH Publishers, Inc., New York, 1989; and Carruthers, Some Modern Methods of Organic Synthesis, 3$^{rd}$ Edition, Cambridge University Press, Cambridge, 1987.

Depending on the choice of the starting materials and procedures, the compounds of the disclosure can be present in the form of one of the possible stereoisomers or as mixtures thereof for stereocenters not fixed by formula (I), formula (I)-A and formula (I)-B—for example as pure optical isomers, or as stereoisomer mixtures, such as racemates and diastereoisomer mixtures, depending on the number of asymmetric carbon atoms. The disclosure is meant to include all such possible stereoisomers, including racemic mixtures, diastereomeric mixtures and optically pure forms. Optically active (R)- and (S)-stereoisomers may be prepared using chiral synthons or chiral reagents, or resolved using conventional techniques. If the compound contains a double bond, the substituent may be the E or Z configuration. If the compound contains a disubstituted cycloalkyl, the cycloalkyl substituent may have a cis- or trans-configuration. All tautomeric forms are also intended to be included.

The term "tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane that are likewise formed by treatment with acid or base. Tautomeric forms may be relevant to the attainment of the optimal chemical reactivity and biological activity of a compound of interest.

As used herein, the terms "salt" or "salts" refers to an acid addition or base addition salt of a compound of the disclosure. "Salts" include in particular "pharmaceutical acceptable salts". The term "pharmaceutically acceptable salts" refers to salts that retain the biological effectiveness and properties of the compounds of the disclosure and, which typically are not biologically or otherwise undesirable. In many cases, the compounds of the disclosure are capable of forming acid and/or base salts by virtue of the presence of amino and/or carboxyl groups or groups similar thereto. Pharmaceutically acceptable salts are well known in the art. For example, Berge et al., describe pharmaceutically acceptable salts in detail in J. Pharmaceutical Sciences, 1977, 66, 1-19, incorporated herein by reference.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the disclosure provides compounds in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

Any formula given herein is also intended to represent unlabeled forms as well as isotopically labeled forms of the compounds. Isotopically labeled compounds have structures depicted by the formulae given herein except that one or more atoms are replaced by an atom having a selected atomic mass or mass number. Isotopes that can be incorporated into compounds of the disclosure include, for example, isotopes of hydrogen.

Further, incorporation of certain isotopes, particularly deuterium (i.e., $^2$H or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of a compound of the disclosure. The concentration of deuterium, may be defined by the isotopic enrichment factor. The term "isotopic enrichment factor" as used herein means the ratio between the isotopic abundance and the natural abundance of a specified isotope. If a substituent in a compound of this disclosure is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

Other examples of isotopes that can be incorporated into compounds of the disclosure include isotopes of hydrogen, carbon, nitrogen, oxygen, phosphorous, fluorine, and chlorine, such as $^3$H, $^{11}$C, $^{13}$C, $^{14}$C, $^{15}$N, $^{18}$F, $^{31}$P, $^{32}$P, $^{35}$S, $^{36}$Cl, $^{123}$I, $^{124}$I, $^{125}$I respectively.

Accordingly it should be understood that the disclosure includes compounds that incorporate one or more of any of the aforementioned isotopes, including for example, radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of the disclosure can generally be prepared by conventional techniques known to those skilled in the art or by processes analogous to those described in the accompanying Examples and Preparations using an appropriate isotopically-labeled reagents in place of the non-labeled reagent previously employed.

As used herein, the term "pharmaceutical composition" refers to a compound of the disclosure, or a pharmaceutically acceptable salt thereof, together with at least one pharmaceutically acceptable carrier, in a form suitable for oral or parenteral administration.

As used herein, the term "pharmaceutically acceptable carrier" refers to a substance useful in the preparation or use of a pharmaceutical composition and includes, for example, suitable diluents, solvents, dispersion media, surfactants, antioxidants, preservatives, isotonic agents, buffering agents, emulsifiers, absorption delaying agents, salts, drug stabilizers, binders, excipients, disintegration agents, lubricants, wetting agents, sweetening agents, flavoring agents, dyes, and combinations thereof, as would be known to those skilled in the art (see, for example, Remington The Science and Practice of Pharmacy, 22$^{nd}$ Ed. Pharmaceutical Press, 2013, pp. 1049-1070).

The term "a therapeutically effective amount" of a compound of the disclosure refers to an amount of the compound of the disclosure that will elicit the biological or medical response of a subject, for example, reduction or inhibition of an enzyme or a protein activity, or ameliorate symptoms, alleviate conditions, slow or delay disease progression, or prevent a disease, etc. In an embodiment, the term "a therapeutically effective amount" refers to the amount of the compound of the disclosure that, when administered to a subject, is effective to (1) at least partially alleviate, prevent and/or ameliorate a condition, or a disorder or a disease (i) mediated by the mTOR pathway, or (ii) associated with mTOR activity, or (iii) characterized by activity (normal or abnormal) of mTOR; or (2) reduce or inhibit the activity of mTOR; or (3) reduce or inhibit the expression of mTOR. In an embodiment, the term "a therapeutically effective amount" refers to the amount of the compound of the disclosure that, when administered to a cell, or a tissue, or a non-cellular biological material, or a medium, is effective to at least partially reducing or inhibiting the activity of mTOR; or at least partially reducing or inhibiting the expression of mTOR.

As used herein, the term "subject" refers to primates (e.g., humans, male or female), dogs, cats, rabbits, guinea pigs, pigs, rats and mice. In certain embodiments, the subject is a primate. In yet other embodiments, the subject is a human.

The terms "administer," "administering," or "administration," as used herein refers to implanting, absorbing, ingesting, injecting, inhaling, or otherwise introducing an inventive compound, or a pharmaceutical composition thereof.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers to alleviating, delaying the onset of, ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient. In some embodiments, "treatment," "treat," and "treating" require that signs or symptoms of the disease, disorder or condition have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

As used herein, the term "prevent", "preventing" or "prevention" of any disease or disorder refers to the prophylactic treatment of the disease or disorder; or delaying the onset or progression of the disease or disorder.

As used herein, "age-related disease or disorder" refers to any disease or disorder whose incidence in a population or severity in an individual correlates with the progression of age. More specifically, an age-related disease or disorder is a disease or disorder whose incidence is at least 1.5 fold higher among human individuals greater than 65 years of age relative to human individuals between the ages of 25-35. Examples of age-related disorders include, but are not limited to: sarcopenia, skin atrophy, cherry angiomas, seborrheic keratoses, brain atrophy—also referred to as dementia, atherosclerosis, arteriosclerosis, pulmonary emphysema, osteoporosis, osteoarthritis, high blood pressure, erectile dysfunction, cataracts, macular degeneration, glaucoma, stroke, cerebrovascular disease (strokes), chronic kidney disease, diabetes-associated kidney disease, impaired hepatic function, liver fibrosis, autoimmune hepatitis, endometrial hyperplasia, metabolic dysfunction, renovascular disease, hearing loss, mobility disability (e.g., frailty), cognitive decline, tendon stiffness, heart dysfunction such as cardiac hypertrophy and/or systolic and/or diastolic dysfunction and/or hypertension, heart dysfunction which results in a decline in ejection fraction, immune senescence, Parkinson's disease, Alzheimer's disease, cancer, immune-senescence leading to cancer due to a decrease in immune-surveillance, infections due to an decline in immune-function, chronic obstructive pulmonary disease (COPD), obesity, loss of taste, loss of olfaction, arthritis, and type II diabetes including complications stemming from diabetes, such as kidney failure, blindness and neuropathy.

As used herein, a subject is "in need of" a treatment if such subject would benefit biologically, medically or in quality of life from such treatment.

All methods described herein can be performed in any suitable order unless otherwise indicated herein or otherwise clearly contradicted by context. The use of any and all examples, or exemplary language (e.g. "such as") provided herein is intended merely to better illuminate the disclosure and does not pose a limitation on the scope of the disclosure otherwise claimed.

Any asymmetric atom (e.g., carbon or the like) of the compound(s) of the disclosure can be present in racemic or enantiomerically enriched, for example the (R)-, (S)- or (R,S)-configuration. In certain embodiments, each asymmetric atom has at least 50 enantiomeric excess, at least 60% enantiomeric excess, at least 70% enantiomeric excess, at least 80% enantiomeric excess, at least 90% enantiomeric excess, at least 95 enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the disclosure can be in the form of one of the possible stereoisomers, rotamers, atropisomers, tautomers or mixtures thereof, for example, as substantially pure geometric (cis or trans) stereoisomers, diastereomers, optical isomers (antipodes), racemates or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of compounds of the disclosure or of intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the disclosure into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds of the disclosure or racemic intermediates can also be resolved by chiral chromatography, e.g., high pressure liquid chromatography (HPLC) using a chiral adsorbent.

Methods of Making Compounds of Formula (I)

In another aspect, the disclosure provides a process for the production of compounds of formula (I), formula (I)-A and formula (I)-B. Compounds of formula (I), formula (I)-A and formula (I)-B can be made according to the following process as described in Schemes 1, 2 and 3:

Scheme 1

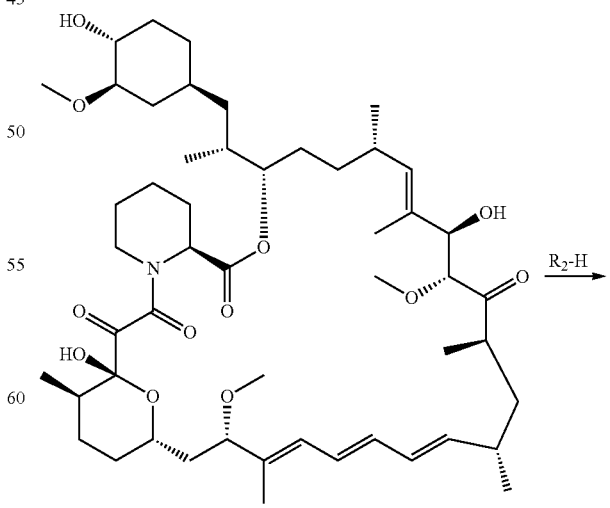

C32-deoxy rapamycin (Intermediate 1)

-continued

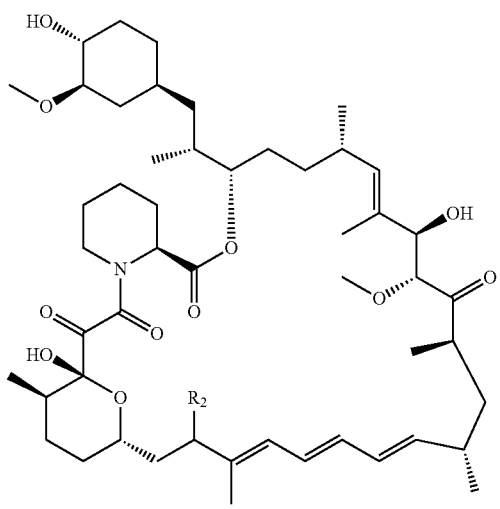

Scheme 2

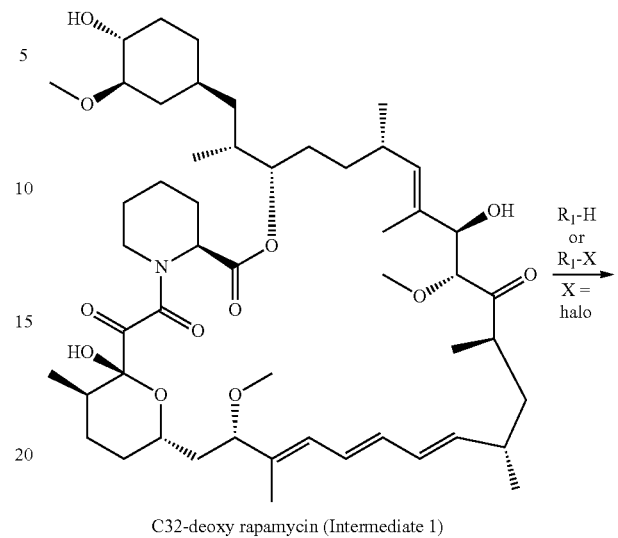

C32-deoxy rapamycin (Intermediate 1)

$R_1$—H
or
$R_1$—X
X = halo

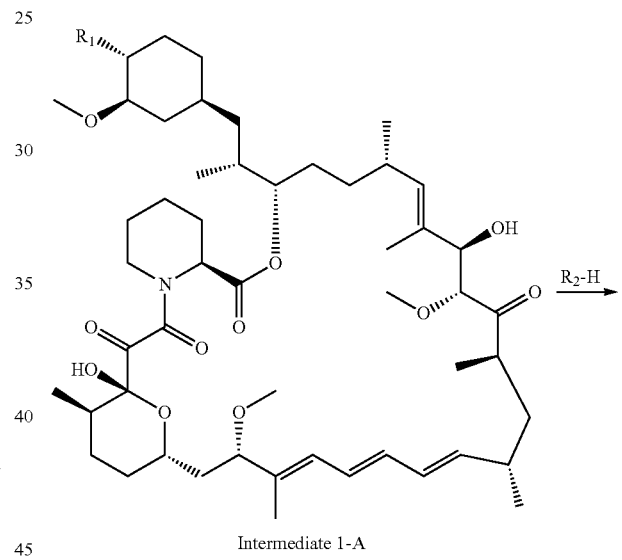

Intermediate 1-A $R_2$—H (I)-A

A compound of formula (I), in which $R_2$ is as defined under formula (I), may be obtained by reacting C32-deoxy rapamycin (Intermediate 1) with $R_2$—H, wherein $R_2$ is as defined under formula (I), in the presence of a suitable reagent for a substitution reaction, e.g. p-toluenesulphonic acid, in the presence of a suitable solvent, e.g. dichloromethane. Suitable conditions are as follows:

1) $R_2$—H, p-toluenesulphonic acid-$H_2O$, dichloromethane, room temperature
2) $R_2$—H, trifluoroacetic acid, −40° C., dichloromethane (see EP121233161)
3) $R_2$—H, 5M $LiClO_4$, $Et_2O$ (0.1M), room temperature (see TL, 1995, 43, 7823)
4) $R_2$—H, $Cp_2HfCl_2$—$AgClO_4$ (Suzuki's catalyst), 4A MS, dichloromethane, room temperature (see TL, 1995, 43, 7823)
5) $R_2$—H, $BF_3$—$OEt_2$ or $Zn(OTf)_2$, THF, 0° C. (see TL, 1994, 37, 6835)
6) $R_2$—H, $ZnCl_2$, dichloromethane, 0° C. (see JOC, 1994, 59, 6512).

C32-deoxy rapamycin used as the starting material can be prepared by methods known in the art, e.g. as described in US Patent Publication No. 005985890 or WO2007085400.

A compound of formula (I)-A, wherein $R_1$ is selected from

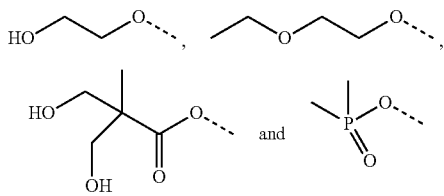

and $R_2$ is as defined under formula (I), may be obtained by reacting Intermediate 1 with $R_1$—H or $R_1$—X followed by reaction with $R_2$—H. In an embodiment, Intermediate 1 is reacted with $R_1$—H or $R_1$—X under alkylation, phosphination or esterification conditions to provide Intermediate 1-A. In an embodiment, Intermediate 1-A is reacted with $R_2$—H under substitution reaction conditions, e.g., as provided herein, to afford a compound of formula (I)-A.

Scheme 3

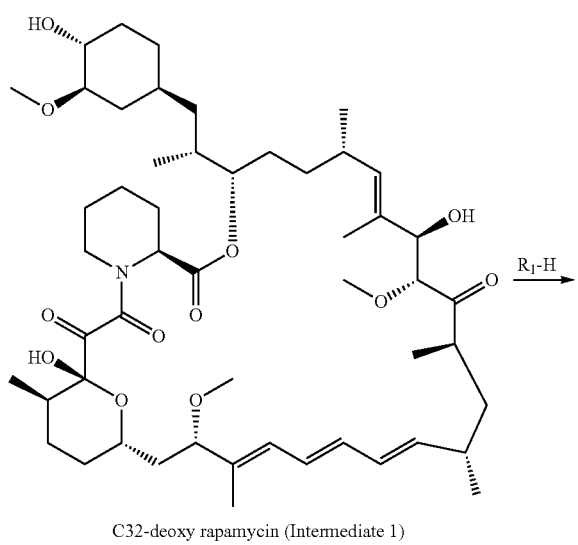

C32-deoxy rapamycin (Intermediate 1)

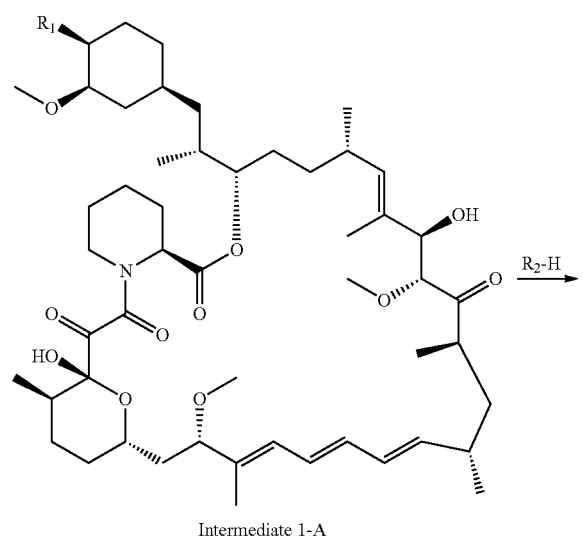

Intermediate 1-A

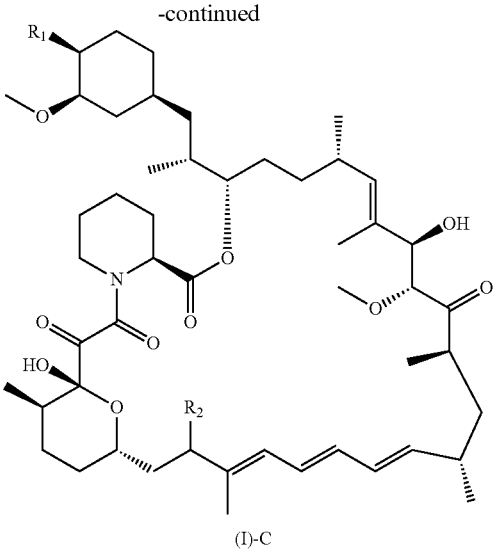

(I)-C

A compound of formula (I)-C, wherein $R_1$ is and $R_2$ is as defined under formula (I), may be obtained by reacting Intermediate 1 with $R_1$—H followed by reaction with $R_2$—H. In an embodiment, Intermediate 1 is activated and reacted under nucleophilic conditions to provide Intermediate 1-A. In an embodiment, Intermediate 1-A is reacted with $R_2$—H under substitution reaction conditions, e.g., as provided herein, to afford the compound of formula (I)-C.

The reactions can be effected according to conventional methods, for example as described in the Examples.

The work-up of the reaction mixtures and the purification of the compounds thus obtainable may be carried out in accordance with known procedures.

Acid addition salts may be produced from the free bases in known manner, and vice-versa.

Starting materials may be known or prepared according to conventional procedures starting from known compounds, for example as described in the Examples.

In another aspect, the disclosure provides a pharmaceutical composition comprising a compound of the disclosure, or a pharmaceutically acceptable salt thereof, and a pharmaceutically acceptable carrier. In a further embodiment, the composition comprises at least two pharmaceutically acceptable carriers, such as those described herein. The pharmaceutical composition can be formulated for particular routes of administration such as oral administration, parenteral administration (e.g. by injection, infusion, transdermal or topical administration), and rectal administration. Topical administration may also pertain to inhalation or intranasal application. The pharmaceutical compositions of the disclosure can be made up in a solid form (including, without limitation, capsules, tablets, pills, granules, powders or suppositories), or in a liquid form (including, without limitation, solutions, suspensions or emulsions). Tablets may be either film coated or enteric coated according to methods known in the art. Typically, the pharmaceutical compositions are tablets or gelatin capsules comprising the active ingredient together with one or more of:
a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and
e) absorbents, colorants, flavors and sweeteners.

The compound of the disclosure, or a pharmaceutically acceptable salt thereof, may also be in the form of a drug-eluting stent, i.e. a stent coated with a compound of the disclosure, or a pharmaceutically acceptable salt thereof.

The compounds of the disclosure in free form or in pharmaceutically acceptable salt form, exhibit valuable pharmacological properties, e.g. mTOR pathway modulating properties, e.g. as indicated in vitro and in vivo tests as provided in the next sections, and are therefore indicated for therapy or for use as research chemicals, e.g. as tool compounds.

Methods to measure potency of mTORC1 inhibitors are well known in the art. Generally, potency is determined by IC50 values, assessed by determining of inhibition of phosphorylation of S6, which is in the mTORC1 signaling pathway. The IC50 values of the mTORC1 inhibitors are compared to the IC50 value of rapamycin in the same assay. An mTORC1 inhibitor having an IC50 value within 100-fold that of the IC50 of rapamycin in the same assay is suitable for use in the disclosure—meaning a less potent rapalog may still be desirable, so as to more easily achieve only partial inhibition of mTORC1 activity in particular settings, and so as to improve the ability to measure the molecule in the bloodstream (since higher concentrations are necessary for a less potent molecule)—which would be helpful in fine-tuning the blood concentration/efficacy relationship.

Suitable assays to measure the potency of mTOR inhibitors are described for instance in U.S. Pat. No. 5,665,772 as measured by the IC50 value in an MLR (mixed lymphocyte reaction) assay and/or in an IL-6 (interleukin-6)-dependent mediated proliferation assay.

The MLR assay is typically carried out as follows: Spleen cells (0.5×106) from Balb/c mice (female, 8-10 weeks) are co-incubated for 5 days with 0.5×106 irradiated (2000 rads) or mitomycin C treated spleen cells from CBA mice (female, 8-10 weeks). The irradiated allogeneic cells induce a proliferative response in the Balb/c spleen cells, which can be measured by labeled precursor incorporation into the DNA. Since the stimulator cells are irradiated (or mitomycin C treated) they do not respond to the Balb/c cells with proliferation but do retain their antigenicity. The antiproliferative effect of the compounds tested on the Balb/c cells is measured at various dilutions and the concentration resulting in 50% inhibition of cell proliferation (IC50) is calculated. The inhibitory capacity of the test sample may be compared to rapamycin and expressed as a relative IC50 (i.e. IC50 test sample/IC50 rapamycin).

The IL-6 mediated proliferation assay is typically carried as follows: the assay uses an interleukin-6 (IL-6)-dependent mouse hybridoma cell line and is performed in 96-well microtiter plates. 5000 cells/well are cultivated in serum-free medium (as described by M. H. Schreier and R. Tees in Immunological Methods, I. Lefkovits and B. Pernis, eds., Academic Press 1981. Vol. II, pp. 263-275), supplemented with 1 ng recombinant IL-6/ml. Following a 66 hour incubation in the absence or presence of a test sample, cells are pulsed with 1 µCi (3-H)-thymidine/well for another 6 hours, harvested and counted by liquid scintillation. (3-H)-thymidine incorporation into DNA correlates with the increase in cell number and is thus a measure of cell proliferation. A dilution series of the test sample allows the calculation of the concentration resulting in 50% inhibition of cell proliferation (IC50). The inhibitory capacity of the test sample may be compared to rapamycin and expressed as a relative IC50 (i.e. IC50 test sample/IC50 rapamycin).

Potency of mTOR inhibitors may also be determined using a MEF TSC1−/− cell-based assay. MEF TSC1−/− cells are Mouse Embryonic Fibroblasts deficient in the Tuberous sclerosis protein, TSC1, which negatively regulates mTORC1 signaling. Thus, the deficiency of TSC1 induces constitutive mTORC1 activation, resulting in phosphorylation (activation) of the downstream proteins in the mTORC1 signaling pathways. This cell-based assay is used to measure inhibition (de-phosphorylation) of the mTORC1 signaling components S6 and 4EBP1, by rapalogs or other mTOR inhibitors.

The assay is typically carried out as follows: MEF TSC1−/− cells are plated on Poly-D-lysine coated 384 well Griener clear bottom plates and incubated overnight at 37° C., 5% CO2. On the following day, cells are washed 8 times with "Hard starve" solution (1 L DPBS+1 g D-(+) glucose+10 ml of 7.5% Sodium Bicarbonate+20 ml of 1M HEPES) and incubated for further 2 hours in the same solution. Cells are next treated with compounds with decreasing concentrations (8 points at 3.16 fold dilutions) and incubated for 2 hours at 37° C., 5% CO2. Cells are fixed with 4% paraformaldehyde for 30 min and washed 5 times with TBS-EDTA followed by immuno-staining with florescent tag labeled antibodies for pS6 and p4EBP1. Nuclei are visualized with Hoechst staining. Cells are imaged using respective florescence channels and the potency of mTOR inhibitors is defined by pS6 $IC_{50}$ (nM).

Diseases and Disorders

Compounds of the disclosure may be useful in the prevention or treatment of an indication or prodromal condition selected from:
Acute or chronic organ or tissue transplant rejection;
Transplant vasculopathies;
Smooth muscle cell proliferation and migration leading to vessel intimal thickening, blood vessel obstruction, obstructive coronary atherosclerosis, restenosis;
Autoimmune diseases and inflammatory conditions;
Treatment and prevention of asthma;
Multi-drug resistance (MDR);
Fungal infections;
Inflammation;
Infection;
Age-related diseases;
Neurodegenerative diseases;
Proliferative disorders, in particular cancer;
Seizures and seizure related disorders;
Mitochondrial myopathy and mitochondrial stress;
Treatable conditions which have been shown to make age-related diseases more likely, such as settings where there is an increase in senescence inducing cytokines (e.g. IL6);
Disorders that include the process of fibrosis and/or inflammation, e.g., liver and kidney disorders. Examples include, liver fibrosis, which occurs in end-stage liver disease; liver cirrhosis; liver failure due to toxicity; non-alcohol-associated hepatic steatosis or NASH; and alcohol-associated steatosis. Another example is kidney fibrosis, which occurs as a result of acute kidney injury, leading to chronic kidney disease. Also, diabetic nephropathy can induce kidney fibrosis and inflammation. Often kidney disease causes heart failure, as a result of an increase in blood pressure; this can also be associated with cardiac fibrosis. Rapalogs possess preclinical efficacy in treating models of cardiac failure, and are effective in decreasing liver fibrosis in patients who have undergone liver transplants (Buss, S. J. et al. Beneficial effects of Mammalian target of rapamycin inhibition on left ventricular remodeling after myocardial infarction. J Am Coll Cardiol. (2009) 54(25): 2435-46; Buss, S. J. et al. Augmentation of autophagy by mTOR-inhibition in myocardial infarction: When size matters. Autophagy. (2010) 6(2):304-6; Villamil, F. G. et al. Fibrosis progression in maintenance liver transplant patients with hepatitis C recurrence: a randomized study of everolimus vs. calcineurin inhibitors. Liver Int. (2014) 34(10): 1513-21).

Treatment of acute or chronic organ or tissue transplant rejection, include the treatment of recipients of e.g., heart, lung, combined heart-lung, liver, kidney, pancreatic, skin or corneal transplants. The compounds of the disclosure also indicated for the prevention of graft-versus-host disease, such as following bone marrow transplantation.

Transplant vasculopathies include atherosclerosis.

Autoimmune diseases and inflammatory conditions include in particular inflammatory conditions with an etiology including an autoimmune component such as arthritis (for example rheumatoid arthritis, arthritis chronica progrediente and arthritis deformans) and rheumatic diseases. Specific autoimmune diseases for which the compounds of formula (I), formula (I)-A, formula (I)-B and formula (I)-C may be employed include, autoimmune hematological disorders (including e. g. hemolytic anemia, aplastic anemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, psoriasis, Steven-Johnson syndrome, idiopathic sprue, autoimmune inflammatory bowel disease (including e. g. ulcerative colitis and Crohn's disease) endocrine ophthalmopathy, Graves disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis, glomerulonephritis (with and without nephrotic syndrome, e.g. including idiopathic nephrotic syndrome or minimal change nephropathy) and juvenile dermatomyositis.

Treatment of multi-drug resistance (MDR) includes enhancing the efficacy of other chemotherapeutic agents in the treatment and control of multidrug resistant conditions such as multidrug resistant cancer or multidrug resistant AIDS. MDR is particularly problematic in cancer patients and ADS patients who will not respond to conventional chemotherapy because the medication is pumped out of the cells by Pgp.

Infection includes infection by pathogens having Mip or Mip-like factors.

Age-related diseases include: sarcopenia, skin atrophy, cherry angiomas, seborrheic keratoses, brain atrophy—also referred to as dementia, atherosclerosis, arteriosclerosis, pulmonary emphysema, osteoporosis, osteoarthritis, high blood pressure, erectile dysfunction, cataracts, macular degeneration, glaucoma, stroke, cerebrovascular disease (strokes), chronic kidney disease, diabetes-associated kidney disease, impaired hepatic function, liver fibrosis, autoimmune hepatitis, endometrial hyperplasia, metabolic dysfunction, renovascular disease, hearing loss, mobility disability (e.g., frailty), cognitive decline, tendon stiffness, heart dysfunction such as cardiac hypertrophy and/or systolic and/or diastolic dysfunction and/or hypertension, heart dysfunction which results in a decline in ejection fraction, immune senescence, Parkinson's disease, Alzheimer's disease, cancer, immune-senescence leading to cancer due to a decrease in immune-surveillance, infections due to an decline in immune-function, chronic obstructive pulmonary disease (COPD), obesity, loss of taste, loss of olfaction, arthritis, and type II diabetes including complications stemming from diabetes, such as kidney failure, blindness and neuropathy.

Neurodegenerative diseases include Huntington's Disease, Parkinson's disease, spinocerebellar ataxia type 3, Alzheimer's disease, motor neuron disease and peripheral neuropathy.

Proliferative disorders include cancer. Such conditions include those listed in U.S. Pat. No. 9,669,032, in particular renal cancer, renal cell carcinoma, colorectal cancer, uterine sarcoma, endometrial uterine cancer, endometrial cancer, breast cancer, ovarian cancer, cervical cancer, gastric cancer, fibro-sarcoma, pancreatic cancer, liver cancer, melanoma, leukemia, multiple myeloma, nasopharyngeal cancer, prostate cancer, lung cancer, glioblastoma, bladder cancer, mesothelioma, head cancer, rhabdomyosarcoma, sarcoma, lymphoma, or neck cancer.

Seizures and seizure related disorders include West syndrome, Focal Cortical Dysplasia (FCD), tuberous sclerosis complex (TSC), childhood absence epilepsy, benign focal epilepsies of childhood, juvenile myoclonic epilepsy (JME), temporal lobe epilepsy, frontal lobe epilepsy, refractory epilepsy, Lennox-Gastaut syndrome, occipital lobe epilepsy, Proteus syndrome, hemi-megalencephaly syndrome (HMEG), megalencephaly syndrome (MEG), megalencephaly-capillary malformation (MCAP) and megalencephaly-polymicrogyria-polydactyly-hydrocephalus syndrome (MPPH).

Mitochondrial myopathy and mitochondrial stress are mitochondrial disorders as described in Chinnery, P. F. (2015); EMBO Mol. Med. 7, 1503-1512; Koopman, W. J. et al., (2016); EMBO Mol. Med. 8, 311-327 and Young, M. J., and Yound and Copeland, W. C. (2016); Curr. Opin. Genet. Dev. 38, 52-62.

Treatable conditions which have been shown to make age-related diseases more likely include senescence, e.g., immune senescence. This is diagnosed by (i) an increase in circulating cytokines, such as IL-6, but also by (ii) senescent cells found in muscle, kidney, liver, brain, neurons, liver, pancreas, or the heart; or also (iii) a decline in the efficiency of DNA-repair, which can be shown by an increase in transcription of repetitive elements, including transposon-encoded genes. For background, see Baker, D. J. et al, Nature, 2016; 530(7589):184-9. doi: 10.1038/nature16932. Epub 2016 Feb. 3.

Methods of Treatment and Uses

The disclosure provides the use of a compound of the disclosure for use in therapy. In a further embodiment, the therapy is selected from a disease or disorder or co-morbidity, which may be treated by modulation of the mTOR pathway. In an embodiment, the disease is selected from the afore-mentioned list, in an embodiment an age-related disease, such as respiratory tract infection-related morbidity in the elderly.

The disclosure provides a compound of the disclosure for use in therapy. In a further embodiment, the therapy is selected from a disease that may be treated by modulation of the mTOR pathway. In an embodiment, the disease is selected from the afore-mentioned list, in an embodiment an age-related disease, such as respiratory tract infection-related morbidity in the elderly.

The disclosure provides the use of a compound of the disclosure for the manufacture of a medicament. In a further embodiment, the medicament is for prevention or treatment of a disease which may be treated by modulation of the mTOR pathway. In an embodiment, the disease is selected from the afore-mentioned list, in an embodiment an age-related disease, such as respiratory tract infection-related morbidity in the elderly.

In one aspect, the disclosure provides a method of treating a disorder or a disease mediated by the mTOR pathway in a subject in need thereof, the method comprising administering to the subject a therapeutically effective amount of a compound of formula (I), formula (I)-A, formula (I)-B and formula (I)-C or a pharmaceutically acceptable salt thereof, a pharmaceutical composition comprising a compound of formula (I), formula (I)-A, formula (I)-B and formula (I)-C or a pharmaceutically acceptable salt thereof, or a pharmaceutical combination comprising a compound of formula (I), formula (I)-A, formula (I)-B and formula (I)-C or a pharmaceutically acceptable salt thereof.

In one aspect, the disclosure provides a method of treating a disease or disorder in a subject, wherein the target tissue or organ associated with the pathology of the disease or disorder has FKBP12 levels sufficient to inhibit mTORC1, the method comprising administering to the subject in need thereof a therapeutically effective amount of a compound of formula (I), formula (I)-A, formula (I)-B and formula (I)-C or a pharmaceutically acceptable salt thereof, a pharmaceutical composition comprising a compound of formula (I), formula (I)-A, formula (I)-B and formula (I)-C or a pharmaceutically acceptable salt thereof, or a pharmaceutical combination comprising a compound of formula (I), formula (I)-A, formula (I)-B and formula (I)-C or a pharmaceutically acceptable salt thereof.

In one aspect, the disclosure provides a method of treating a disease or disorder in a subject having, or previously determined as having, FKBP12 levels sufficient to inhibit mTORC1, the method comprising administering to the subject in need thereof a therapeutically effective amount of a compound of formula (I), formula (I)-A, formula (I)-B and formula (I)-C or a pharmaceutically acceptable salt thereof, a pharmaceutical composition comprising a compound of formula (I), formula (I)-A, formula (I)-B and formula (I)-C or a pharmaceutically acceptable salt thereof, or a pharmaceutical combination comprising a compound of formula (I), formula (I)-A, formula (I)-B and formula (I)-C or a pharmaceutically acceptable salt thereof.

In an embodiment, the disease or disorder is selected from sarcopenia, skin atrophy, cherry angiomas, seborrheic keratoses, brain atrophy, atherosclerosis, arteriosclerosis, pulmonary emphysema, osteoporosis, osteoarthritis, high blood pressure, erectile dysfunction, cataracts, macular degeneration, glaucoma, stroke, cerebrovascular disease (strokes), chronic kidney disease, diabetes-associated kidney disease, impaired hepatic function, liver fibrosis, autoimmune hepatitis, endometrial hyperplasia, metabolic dysfunction, renovascular disease, hearing loss, mobility disability, cognitive decline, tendon stiffness, heart dysfunction such as cardiac hypertrophy and/or systolic and/or diastolic dysfunction and/or hypertension, heart dysfunction which results in a decline in ejection fraction, immune senescence, Parkinson's disease, Alzheimer's disease, cancer, immune-senescence leading to cancer due to a decrease in immune-surveillance, infections due to an decline in immune-function, chronic obstructive pulmonary disease (COPD), obesity, loss of taste, loss of olfaction, arthritis, and type II diabetes including complications stemming from diabetes, such as kidney failure, blindness and neuropathy.

In an embodiment, the disorder is liver fibrosis.

In one aspect, the disclosure provides a method of treating a disease or disorder in a subject in need thereof, the method comprising administering to the subject a therapeutically effective amount of a compound of formula (I), formula (I)-A, formula (I)-B and formula (I)-C or a pharmaceutically acceptable salt thereof, a pharmaceutical composition comprising a compound of formula (I), formula (I)-A, formula (I)-B and formula (I)-C or a pharmaceutically acceptable salt thereof, or a pharmaceutical combination comprising a compound of formula (I), formula (I)-A, formula (I)-B and formula (I)-C or a pharmaceutically acceptable salt thereof, wherein the disorder or disease is selected from:

Acute or chronic organ or tissue transplant rejection;
Transplant vasculopathies;
Smooth muscle cell proliferation and migration leading to vessel intimal thickening, blood vessel obstruction, obstructive coronary atherosclerosis, restenosis;
Autoimmune diseases and inflammatory conditions;
Treatment and prevention of asthma;
Multi-drug resistance (MDR);
Fungal infections;
Inflammation;
Infection;
Age-related diseases;
Neurodegenerative diseases;
Proliferative disorders, in particular cancer;
Seizures and seizure related disorders; and
Mitochondrial myopathy and mitochondrial stress.

In an embodiment, the disorder is a disorder that includes the process of fibrosis and/or inflammation.

In an embodiment, the disorder is selected from liver and kidney disorders.

In an embodiment, the liver disorder is selected from: liver fibrosis, which occurs in end-stage liver disease; liver cirrhosis; liver failure due to toxicity; non-alcohol-associated hepatic steatosis or NASH; and alcohol-associated steatosis.

In an embodiment, the kidney disorder is kidney fibrosis.

In an embodiment, the kidney fibrosis occurs as a result of acute kidney injury.

In an embodiment, the kidney disorder is chronic kidney disorder.

In an embodiment, the kidney disorder is diabetic nephropathy.

In one aspect, the disclosure provides a method of treating an age-related disorder or disease in a subject in need thereof, the method comprising administering to the subject a therapeutically effective amount of a compound of formula (I), formula (I)-A, formula (I)-B and formula (I)-C or a pharmaceutically acceptable salt thereof, a pharmaceutical composition comprising a compound of formula (I), formula (I)-A, formula (I)-B and formula (I)-C or a pharmaceutically acceptable salt thereof, or a pharmaceutical combination comprising a compound of formula (I), formula (I)-A, formula (I)-B and formula (I)-C or a pharmaceutically acceptable salt thereof, wherein the disorder or disease is selected from: sarcopenia, skin atrophy, cherry angiomas, seborrheic keratoses, brain atrophy, atherosclerosis, arteriosclerosis, pulmonary emphysema, osteoporosis, osteoarthritis, high blood pressure, erectile dysfunction, cataracts, macular degeneration, glaucoma, stroke, cerebrovascular disease (strokes), chronic kidney disease, diabetes-associated kidney disease, impaired hepatic function, liver fibrosis, autoimmune hepatitis, endometrial hyperplasia, metabolic dysfunction, renovascular disease, hearing loss, mobility disability, cognitive decline, tendon stiffness, heart dysfunction such as cardiac hypertrophy and/or systolic and/or diastolic dysfunction and/or hypertension, heart dysfunction which results in a decline in ejection fraction, immune senescence, Parkinson's disease, Alzheimer's disease, cancer, immune-senescence leading to cancer due to a decrease in immune-surveillance, infections due to an decline in immune-function, chronic obstructive pulmonary disease (COPD), obesity, loss of taste, loss of olfaction, arthritis, and type II diabetes including complications stemming from diabetes, such as kidney failure, blindness and neuropathy.

In one aspect, the disclosure provides a method of treating cancer in a subject, the method comprising administering to the subject a therapeutically effective amount of a compound of formula (I), formula (I)-A, formula (I)-B and formula (I)-C or a pharmaceutically acceptable salt thereof, a pharmaceutical composition comprising a compound of formula (I), formula (I)-A, formula (I)-B and formula (I)-C or a pharmaceutically acceptable salt thereof, or a pharmaceutical combination comprising a compound of formula (I), formula (I)-A, formula (I)-B and formula (I)-C or a pharmaceutically acceptable salt thereof.

In an embodiment, the method further comprises a PD-1/PDL-1 inhibitor.

In an embodiment, the cancer is selected from renal cancer, renal cell carcinoma, colorectal cancer, uterine sarcoma, endometrial uterine cancer, endometrial cancer, breast cancer, ovarian cancer, cervical cancer, gastric cancer, fibrosarcoma, pancreatic cancer, liver cancer, melanoma, leukemia, multiple myeloma, nasopharyngeal cancer, prostate cancer, lung cancer, glioblastoma, bladder cancer, mesothelioma, head cancer, rhabdomyosarcoma, sarcoma, lymphoma, and neck cancer.

In one aspect, the disclosure provides a compound of formula (I), formula (I)-A, formula (I)-B and formula (I)-C or a pharmaceutically acceptable salt thereof, a pharmaceutical composition comprising a compound of formula (I), formula (I)-A, formula (I)-B and formula (I)-C or a pharmaceutically acceptable salt thereof, or a pharmaceutical combination comprising a compound of formula (I), formula (I)-A, formula (I)-B and formula (I)-C or a pharmaceutically acceptable salt thereof, for use as a medicament.

In one aspect, the disclosure provides a compound of formula (I), formula (I)-A, formula (I)-B and formula (I)-C or a pharmaceutically acceptable salt thereof, a pharmaceutical composition comprising a compound of formula (I), formula (I)-A, formula (I)-B and formula (I)-C or a pharmaceutically acceptable salt thereof, or a pharmaceutical combination comprising a compound of formula (I), formula (I)-A, formula (I)-B and formula (I)-C or a pharmaceutically acceptable salt thereof, for use in the prevention or treatment of a disorder or disease mediated by the mTOR pathway.

In one aspect, the disclosure provides a compound of formula (I), formula (I)-A, formula (I)-B and formula (I)-C or a pharmaceutically acceptable salt thereof, a pharmaceutical composition comprising a compound of formula (I), formula (I)-A, formula (I)-B and formula (I)-C or a pharmaceutically acceptable salt thereof, or a pharmaceutical combination comprising a compound of formula (I), formula (I)-A, formula (I)-B and formula (I)-C or a pharmaceutically acceptable salt thereof, for use in the prevention or treatment of a disorder or disease selected from:
Acute or chronic organ or tissue transplant rejection;
Transplant vasculopathies;
Smooth muscle cell proliferation and migration leading to vessel intimal thickening, blood vessel obstruction, obstructive coronary atherosclerosis, restenosis;
Autoimmune diseases and inflammatory conditions;
Treatment and prevention of asthma;
Multi-drug resistance (MDR);
Fungal infections;
Inflammation;
Infection;
Age-related diseases;
Neurodegenerative diseases;
Proliferative disorders, in particular cancer;
Seizures and seizure related disorders;
Mitochondrial myopathy and mitochondrial stress; and
Treatable conditions which have been shown to make age-related diseases more likely, such as settings where there is an increase in senescence inducing cytokines.

In one aspect, the disclosure provides a compound of formula (I), formula (I)-A, formula (I)-B and formula (I)-C or a pharmaceutically acceptable salt thereof, a pharmaceutical composition comprising a compound of formula (I), formula (I)-A, formula (I)-B and formula (I)-C or a pharmaceutically acceptable salt thereof, or a pharmaceutical combination comprising a compound of formula (I), formula (I)-A, formula (I)-B and formula (I)-C or a pharmaceutically acceptable salt thereof, for use in the prevention or treatment of a disorder or disease that includes the process of fibrosis and/or inflammation.

In an embodiment, the disorder is selected from liver and kidney disorders.

In an embodiment, the liver disorder is selected from: liver fibrosis, which occurs in end-stage liver disease; liver cirrhosis; liver failure due to toxicity; non-alcohol-associated hepatic steatosis or NASH; and alcohol-associated steatosis.

In an embodiment, the kidney disorder is kidney fibrosis, which occurs as a result of acute kidney injury.

In an embodiment, the kidney disorder is chronic kidney disorder.

In an embodiment, the kidney disorder is diabetic nephropathy.

In one aspect, the disclosure provides a compound of formula (I), formula (I)-A, formula (I)-B and formula (I)-C or a pharmaceutically acceptable salt thereof, a pharmaceutical composition comprising a compound of formula (I), formula (I)-A, formula (I)-B and formula (I)-C or a pharmaceutically acceptable salt thereof, or a pharmaceutical combination comprising a compound of formula (I), formula (I)-A, formula (I)-B and formula (I)-C or a pharmaceutically acceptable salt thereof, for use in the prevention or treatment of an age-related disorder or disease selected from sarcopenia, skin atrophy, cherry angiomas, seborrheic keratoses, brain atrophy—also referred to as dementia, atherosclerosis, arteriosclerosis, pulmonary emphysema, osteoporosis, osteoarthritis, high blood pressure, erectile dysfunction, cataracts, macular degeneration, glaucoma, stroke, cerebrovascular disease (strokes), chronic kidney disease, diabetes-associated kidney disease, impaired hepatic function, liver fibrosis, autoimmune hepatitis, endometrial hyperplasia, metabolic dysfunction, renovascular disease, hearing loss, mobility disability (e.g., frailty), cognitive decline, tendon stiffness, heart dysfunction such as cardiac hypertrophy and/or systolic and/or diastolic dysfunction and/or hypertension, heart dysfunction which results in a decline in ejection fraction, immune senescence, Parkinson's disease, Alzheimer's disease, cancer, immune-senescence leading to cancer due to a decrease in immune-surveillance, infections due to an decline in immune-function, chronic obstructive pulmonary disease (COPD), obesity, loss of taste, loss of olfaction, arthritis, and type II diabetes including complications stemming from diabetes, such as kidney failure, blindness and neuropathy.

In one aspect, the disclosure provides a compound of formula (I), formula (I)-A, formula (I)-B and formula (I)-C or a pharmaceutically acceptable salt thereof, a pharmaceutical composition comprising a compound of formula (I), formula (I)-A, formula (I)-B and formula (I)-C or a pharmaceutically acceptable salt thereof, or a pharmaceutical combination comprising a compound of formula (I), formula (I)-A, formula (I)-B and formula (I)-C or a pharmaceutically acceptable salt thereof, for use in the prevention or treatment of cancer.

In one aspect, the disclosure provides a compound of formula (I), formula (I)-A, formula (I)-B and formula (I)-C or a pharmaceutically acceptable salt thereof, a pharmaceutical composition comprising a compound of formula (I), formula (I)-A, formula (I)-B and formula (I)-C or a pharmaceutically acceptable salt thereof, or a pharmaceutical combination comprising a compound of formula (I), formula (I)-A, formula (I)-B and formula (I)-C or a pharmaceutically acceptable salt thereof, for use in the treatment of renal cancer, renal cell carcinoma, colorectal cancer, uterine sarcoma, endometrial uterine cancer, endometrial cancer, breast cancer, ovarian cancer, cervical cancer, gastric cancer, fibrosarcoma, pancreatic cancer, liver cancer, melanoma, leukemia, multiple myeloma, nasopharyngeal cancer, prostate cancer, lung cancer, glioblastoma, bladder cancer, mesothelioma, head cancer, rhabdomyosarcoma, sarcoma, lymphoma, or neck cancer.

In an embodiment, the disclosure provides a compound

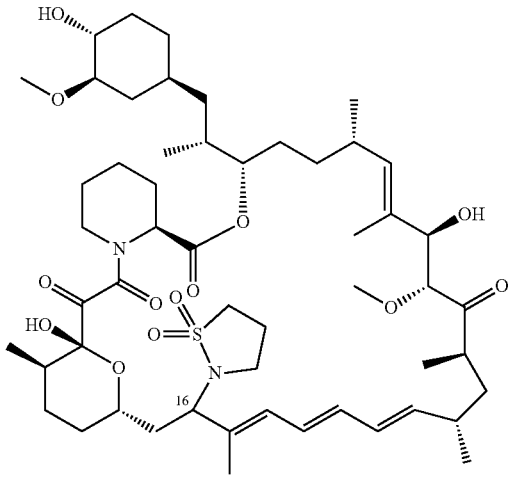 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)C(N3CCCS3(=O)=O)C[C@@H]3CC[C@@H](C)[C@@](O)(O3)C(=O)C(=O)N3CCCC[C@H]3C(=O)O2)CC[C@H]1O]

or a pharmaceutically acceptable salt thereof for use in the treatment of an age-related disease, such as respiratory tract infection-related morbidity in the elderly. In an embodiment, the compound is (S)-C16-(1,1-dioxidoisothiazolidin-2-yl)-C32-deoxo-rapamycin (Example 1) or a pharmaceutically acceptable salt thereof. In an embodiment, the compound is (R)—C16-(1,1-dioxidoisothiazolidin-2-yl)-C32-deoxo-rapamycin (Example 2) or a pharmaceutically acceptable salt thereof.

In an embodiment, the disorder or disease is selected from:
Acute or chronic organ or tissue transplant rejection;
Transplant vasculopathies;
Smooth muscle cell proliferation and migration leading to vessel intimal thickening, blood vessel obstruction, obstructive coronary atherosclerosis, restenosis;
Autoimmune diseases and inflammatory conditions;
Treatment and prevention of asthma;
Multi-drug resistance (MDR);
Fungal infections;
Inflammation;
Infection;
Age-related diseases;
Neurodegenerative diseases;
Proliferative disorders, in particular cancer;
Seizures and seizure related disorders;
Mitochondrial myopathy and mitochondrial stress; and
Treatable conditions which are shown to make age-related diseases more likely, such as settings where there is an increase in senescence inducing cytokines (e.g. IL6).

In an embodiment, the disorder or disease is an age-related disorder or disease selected from sarcopenia, skin atrophy, cherry angiomas, seborrheic keratoses, brain atrophy—also referred to as dementia, atherosclerosis, arteriosclerosis, pulmonary emphysema, osteoporosis, osteoarthritis, high blood pressure, erectile dysfunction, cataracts, macular degeneration, glaucoma, stroke, cerebrovascular disease (strokes), chronic kidney disease, diabetes-associated kidney disease, impaired hepatic function, liver fibrosis, autoimmune hepatitis, endometrial hyperplasia, metabolic dysfunction, renovascular disease, hearing loss, mobility disability (e.g., frailty), cognitive decline, tendon stiffness, heart dysfunction such as cardiac hypertrophy and/or systolic and/or diastolic dysfunction and/or hypertension, heart dysfunction which results in a decline in ejection fraction, immune senescence, Parkinson's disease, Alzheimer's disease, cancer, immune-senescence leading to cancer due to a decrease in immune-surveillance, infections due to an decline in immune-function, chronic obstructive pulmonary disease (COPD), obesity, loss of taste, loss of olfaction, arthritis, and type II diabetes including complications stemming from diabetes, such as kidney failure, blindness and neuropathy.

In an embodiment, the disorder or disease includes the process of fibrosis and/or inflammation, e.g., liver and kidney disorders. In an embodiment, the disorder is a kidney disorder. In an embodiment, the disorder is a liver disorder. Examples include, liver fibrosis, which occurs in end-stage liver disease; liver cirrhosis; liver failure due to toxicity; non-alcohol-associated hepatic steatosis or NASH; and alcohol-associated steatosis. Another example is kidney fibrosis, which occurs as a result of acute kidney injury, leading to chronic kidney disease. Also, diabetic nephropathy can induce kidney fibrosis and inflammation. Often kidney disease causes heart failure, as a result of an increase in blood pressure; this can also be associated with cardiac fibrosis. Rapalogs possess preclinical efficacy in treating models of cardiac failure, and are effective in decreasing liver fibrosis in patients who have undergone liver transplants.

The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the disclosure may be applied in vitro in the form of solutions, e.g., aqueous solutions, and in vivo either enterally, parenterally, advantageously intravenously, e.g., as a suspension or in aqueous solution. The dosage in vitro may range between about $10^{-9}$ molar and $10^{-9}$ molar concentrations. A therapeutically effective amount in vivo may range depending on the route of administration, between about 0.1-500 mg/kg, or between about 0.1-500 mg per subject.

The compound of the disclosure may be administered either simultaneously with, or before or after, one or more other therapeutic agent. The compound of the disclosure may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the disclosure.

In an embodiment, the disclosure provides a product comprising a compound of the disclosure and at least one other therapeutic agent as a combined preparation for simultaneous, separate or sequential use in therapy. In an embodiment, the therapy is the treatment of a disease or condition via partial or full inhibition of mTOR. Products provided as a combined preparation include a composition comprising the compound of the disclosure and the other therapeutic agent(s) together in the same pharmaceutical composition, or the compound of the disclosure and the other therapeutic agent(s) in separate form, e.g. in the form of a kit.

In an embodiment, the disclosure provides a pharmaceutical composition comprising a compound of the disclosure and another therapeutic agent(s). Optionally, the pharmaceutical composition may comprise a pharmaceutically acceptable carrier, as described above.

In an embodiment, the disclosure provides a kit comprising two or more separate pharmaceutical compositions, at least one of which contains a compound of the disclosure. In an embodiment, the kit comprises means for separately retaining said compositions, such as a container, divided bottle, or divided foil packet. An example of such a kit is a blister pack, as typically used for the packaging of tablets, capsules and the like.

The kit of the disclosure may be used for administering different dosage forms, for example, oral and parenteral, for administering the separate compositions at different dosage intervals, or for titrating the separate compositions against one another. To assist compliance, the kit of the disclosure typically comprises directions for administration.

In the combination therapies of the disclosure, the compound of the disclosure and the other therapeutic agent may be manufactured and/or formulated by the same or different manufacturers. Moreover, the compound of the disclosure and the other therapeutic may be brought together into a combination therapy: (i) prior to release of the combination product to physicians (e.g. in the case of a kit comprising the compound of the disclosure and the other therapeutic agent); (ii) by the physician themselves (or under the guidance of the physician) shortly before administration; (iii) in the patient themselves, e.g. during sequential administration of the compound of the disclosure and the other therapeutic agent.

Accordingly, the disclosure provides the use of a compound of the disclosure for preventing or treating a disease or condition via partial or full inhibition of mTOR, wherein the medicament is prepared for administration with another therapeutic agent. The disclosure also provides the use of another therapeutic agent for preventing or treating a disease or condition mediated by mTOR inhibition, wherein the medicament is administered with a compound of the disclosure.

The disclosure also provides a compound of formula (I), formula (I)-A and formula (I)-B or a pharmaceutically acceptable salt thereof for use in a method of preventing or treating a disease or condition mediated by mTOR inhibition, wherein the compound of the disclosure is prepared for administration with another therapeutic agent. The disclosure also provides another therapeutic agent for use in a method of preventing or treating a disease or condition mediated by mTOR inhibition, wherein the other therapeutic agent is prepared for administration with a compound of formula (I), formula (I)-A and formula (I)-B or a pharmaceutically acceptable salt thereof. The disclosure also provides a compound of formula (I), formula (I)-A and formula (I)-B or a pharmaceutically acceptable salt thereof for use in a method of preventing or treating a disease or condition mediated by mTOR inhibition, wherein the compound is administered with another therapeutic agent. The disclosure also provides another therapeutic agent for use in a method of preventing or treating a disease or condition mediated by mTOR inhibition, wherein the other therapeutic agent is administered with a compound of formula (I), formula (I)-A and formula (I)-B or a pharmaceutically acceptable salt thereof.

The disclosure also provides the use of a compound of formula (I), formula (I)-A and formula (I)-B or a pharmaceutically acceptable salt thereof for preventing or treating a disease or condition mediated by mTOR, wherein the patient has previously (e.g. within 24 hours) been treated with another therapeutic agent. The disclosure also provides the use of another therapeutic agent for preventing or treating a disease or condition mediated by mTOR, wherein the patient has previously (e.g. within 24 hours) been treated with a compound of formula (I), formula (I)-A and formula (I)-B or a pharmaceutically acceptable salt thereof.

Specific individual combinations which may provide particular treatment benefits include a combination of a compound

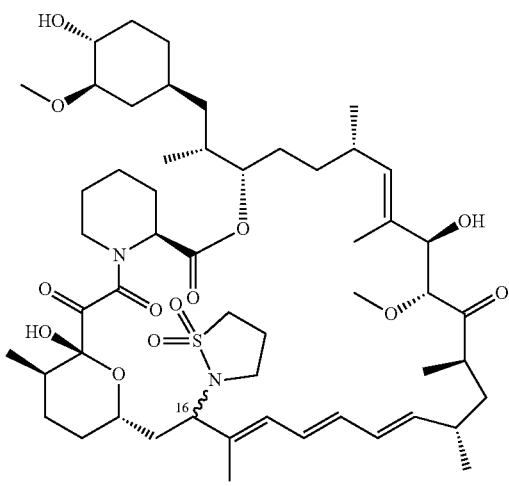 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)C(N3CCCS3(=O)=O)C[C@@H]3CC[C@@H](C)[C@@](O)(O3)C(=O)C(=O)N3CCCC[C@H]3C(=O)O2)CC[C@H]1O]

or a pharmaceutically acceptable salt thereof and a catalytic mTOR inhibitor, in particular one as mentioned above. In an embodiment, the compound is (S)-C16-(1,1-dioxidoisothiazolidin-2-yl)-C32-deoxo-rapamycin (Example 1) or a pharmaceutically acceptable salt thereof. In an embodiment, the compound is (R)—C16-(1,1-dioxidoisothiazolidin-2-yl)-C32-deoxo-rapamycin (Example 2) or a pharmaceutically acceptable salt thereof.

In an embodiment, the disclosure provides a product comprising a compound

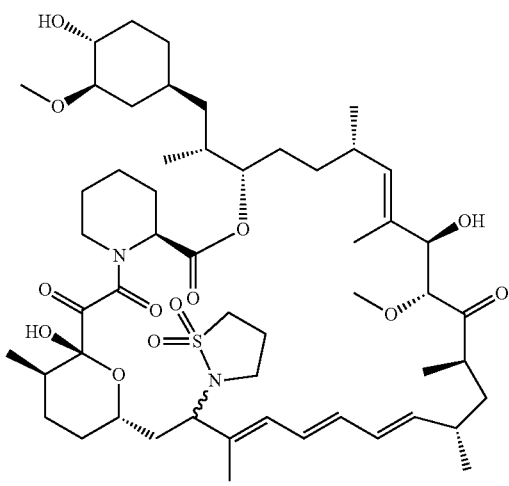 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)C(N3CCCS3(=O)=O)C[C@@H]3CC[C@@H](C)[C@@](O)(O3)C(=O)C(=O)N3CCCC[C@H]3C(=O)O2)CC[C@H]1O]

or a pharmaceutically acceptable salt thereof and a catalytic mTOR inhibitor, in particular one as mentioned above as a combined preparation for simultaneous, separate or sequential use in therapy. In an embodiment, the compound is (S)-C16-(1,1-dioxidoisothiazolidin-2-yl)-C32-deoxo-rapamycin (Example 1) or a pharmaceutically acceptable salt thereof. In an embodiment, the compound is (R)—C16-(1,1-dioxidoisothiazolidin-2-yl)-C32-deoxo-rapamycin (Example 2) or a pharmaceutically acceptable salt thereof.

In an embodiment, the disclosure provides a pharmaceutical composition comprising a compound

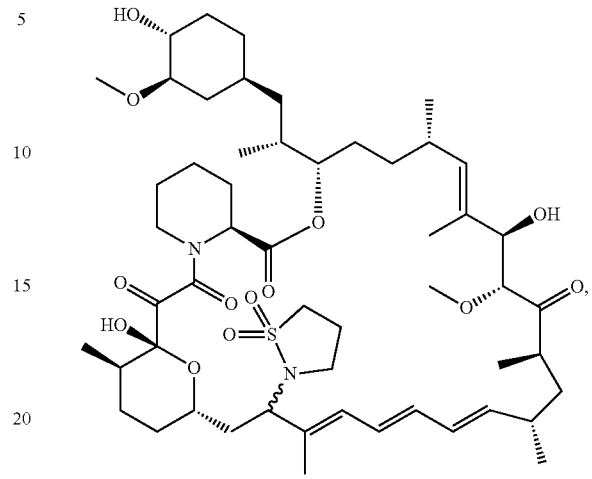

or a pharmaceutically acceptable salt thereof and a catalytic mTOR inhibitor, in particular one as mentioned above, and a pharmaceutically acceptable carrier. In an embodiment, the compound is (S)-C16-(1,1-dioxidoisothiazolidin-2-yl)-C32-deoxo-rapamycin (Example 1) or a pharmaceutically acceptable salt thereof. In an embodiment, the compound is (R)—C16-(1,1-dioxidoisothiazolidin-2-yl)-C32-deoxo-rapamycin (Example 2) or a pharmaceutically acceptable salt thereof.

In an embodiment, the other therapeutic agent is selected from a CD4 lymphocyte depleting agent, such as an anti-CD4 antibody or antigen-binding fragment thereof, such as a humanized anti-CD4 antibody, e.g. zanolimumab. Such a therapeutic agent may in particular be used for the treatment of a proliferative disorder, in particular cancer. See also U.S. Pat. Nos. 8,906,374 and 9,427,463 for such a combination therapy.

Specific individual combinations which may provide particular treatment benefits include a combination of a compound

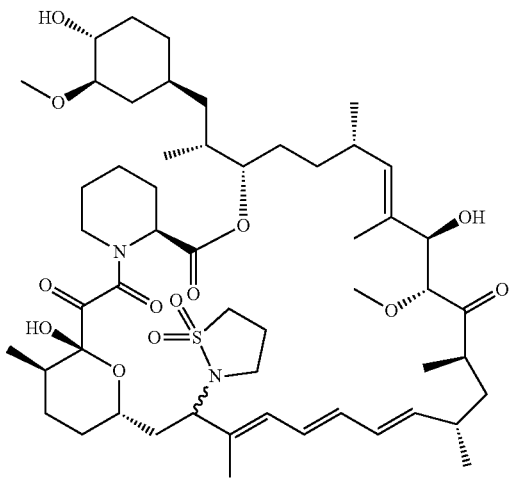

or a pharmaceutically acceptable salt thereof and a CD4 lymphocyte depleting agent, in particular one as mentioned above. In an embodiment, the compound is (S)-C16-(1,1-dioxidoisothiazolidin-2-yl)-C32-deoxo-rapamycin (Example 1) or a pharmaceutically acceptable salt thereof. In an embodiment, the compound is (R)—C16-(1,1-dioxidoisothiazolidin-2-yl)-C32-deoxo-rapamycin (Example 2) or a pharmaceutically acceptable salt thereof.

In an embodiment, the disclosure provides a product comprising a compound

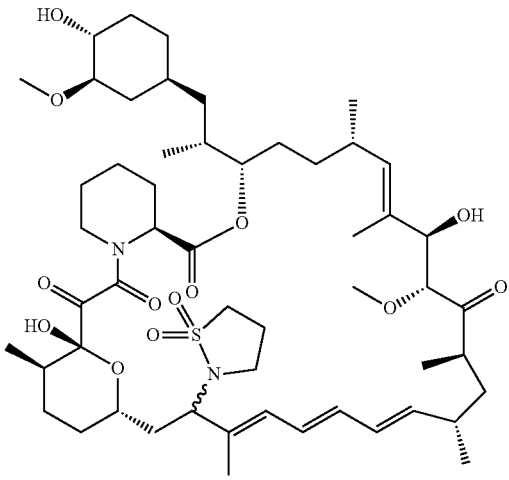 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)C(N3CCCS3(=O)=O)C[C@@H]3CC[C@@H](C)[C@@](O)(O3)C(=O)C(=O)N3CCCC[C@H]3C(=O)O2)CC[C@H]1O]

or a pharmaceutically acceptable salt thereof and a CD4 lymphocyte depleting agent, in particular one as mentioned above as a combined preparation for simultaneous, separate or sequential use in therapy. In an embodiment, the compound is (S)-C16-(1,1-dioxidoisothiazolidin-2-yl)-C32-deoxo-rapamycin (Example 1) or a pharmaceutically acceptable salt thereof. In an embodiment, the compound is (R)—C16-(1,1-dioxidoisothiazolidin-2-yl)-C32-deoxo-rapamycin (Example 2) or a pharmaceutically acceptable salt thereof.

In an embodiment, the disclosure provides a pharmaceutical composition comprising a compound

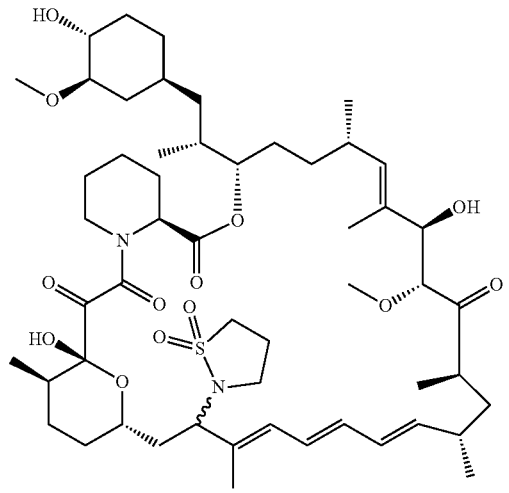 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)C(N3CCCS3(=O)=O)C[C@@H]3CC[C@@H](C)[C@@](O)(O3)C(=O)C(=O)N3CCCC[C@H]3C(=O)O2)CC[C@H]1O]

or a pharmaceutically acceptable salt thereof, a CD4 lymphocyte depleting agent, in particular one as mentioned above, and a pharmaceutically acceptable carrier. In an embodiment, the compound is (S)-C16-(1,1-dioxidoisothiazolidin-2-yl)-C32-deoxo-rapamycin (Example 1) or a pharmaceutically acceptable salt thereof. In an embodiment, the compound is (R)—C16-(1,1-dioxidoisothiazolidin-2-yl)-C32-deoxo-rapamycin (Example 2) or a pharmaceutically acceptable salt thereof.

In an embodiment, the other therapeutic agent is selected from an agent that modulates the activity of immunoinhibitory proteins, such as PD-1/PDL-1, such as an anti-PD-1 antibody or PDL-1 antibody. Anti-PD-1 antibodies which are useful as such a therapeutic agent are as disclosed in U.S. Pat. No. 9,683,048. Such a therapeutic agent may be used in the treatment of cancer, in particular for cancer immunotherapy.

Specific individual combinations which may provide particular treatment benefits include a combination of a compound

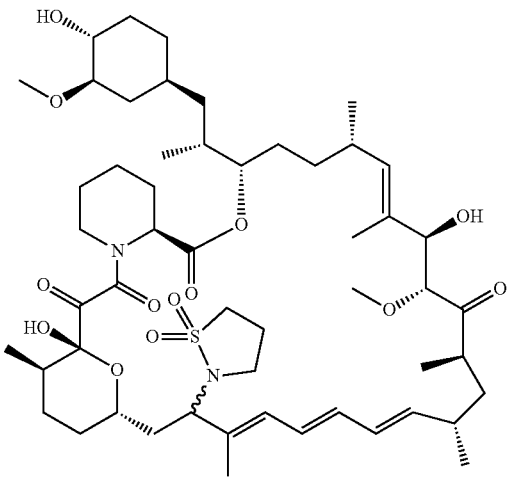 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)C(N3CCCS3(=O)=O)C[C@@H]3CC[C@@H](C)[C@@](O)(O3)C(=O)C(=O)N3CCCC[C@H]3C(=O)O2)CC[C@H]1O]

or a pharmaceutically acceptable salt thereof and an agent that modulates the activity of immunoinhibitory proteins, such as PD-1, in particular one as mentioned above. In an embodiment, the compound is (S)-C16-(1,1-dioxidoisothiazolidin-2-yl)-C32-deoxo-rapamycin (Example 1) or a pharmaceutically acceptable salt thereof. In an embodiment, the compound is (R)—C16-(1,1-dioxidoisothiazolidin-2-yl)-C32-deoxo-rapamycin (Example 2) or a pharmaceutically acceptable salt thereof.

In an embodiment, the disclosure provides a product comprising a compound

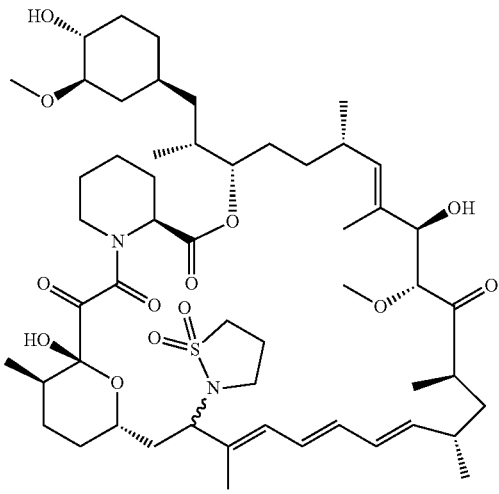 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)C(N3CCCS3(=O)=O)C[C@@H]3CC[C@@H](C)[C@@](O)(O3)C(=O)C(=O)N3CCCC[C@H]3C(=O)O2)CC[C@H]1O]

or a pharmaceutically acceptable salt thereof and an agent that modulates the activity of immunoinhibitory proteins, such as PD-1, in particular one as mentioned above as a combined preparation for simultaneous, separate or sequential use in therapy. In an embodiment, the compound is (S)-C16-(1,1-dioxidoisothiazolidin-2-yl)-C32-deoxo-rapamycin (Example 1) or a pharmaceutically acceptable salt thereof. In an embodiment, the compound is (R)—C16-(1,1-dioxidoisothiazolidin-2-yl)-C32-deoxo-rapamycin (Example 2) or a pharmaceutically acceptable salt thereof.

In an embodiment, the disclosure provides a pharmaceutical composition comprising

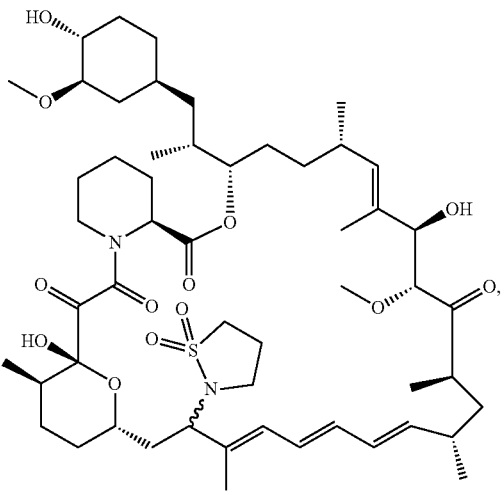 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)C(N3CCCS3(=O)=O)C[C@@H]3CC[C@@H](C)[C@@](O)(O3)C(=O)C(=O)N3CCCC[C@H]3C(=O)O2)CC[C@H]1O]

or a pharmaceutically acceptable salt thereof, an agent that modulates the activity of immunoinhibitory proteins, such as PD-1, in particular one as mentioned above, and a pharmaceutically acceptable carrier. In an embodiment, the compound is (S)-C16-(1,1-dioxidoisothiazolidin-2-yl)-C32-deoxo-rapamycin (Example 1) or a pharmaceutically acceptable salt thereof. In an embodiment, the compound is (R)—C16-(1,1-dioxidoisothiazolidin-2-yl)-C32-deoxo-rapamycin (Example 2) or a pharmaceutically acceptable salt thereof.

EXAMPLES

The disclosure sets for the following examples. The synthetic and biological examples described in this application are offered to illustrate the compounds, pharmaceutical compositions, and methods provided herein and are not to be construed in any way as limiting their scope.

The compounds provided herein can be prepared from readily available starting materials using modifications to the specific synthesis protocols set forth below that would be well known to those of skill in the art. It will be appreciated that where typical or preferred process conditions (i.e., reaction temperatures, times, mole ratios of reactants, solvents, pressures, etc.) are given other process conditions can also be used unless otherwise stated. Optimum reaction conditions may vary with the particular reactants or solvents used, but such conditions can be determined by those skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., *Protecting Groups in Organic Synthesis*, Second Edition, Wiley, New York, 1991, and references cited therein.

Rapamycin and its derivatives, for example, compounds of formula (I), formula (I)-A and formula (I)-B exist as a solvent and pH dependent equilibrium of six-membered and seven-membered hemi-ketal forms shown below as E and F (Schemes 4 and 5). See *The Journal of Antibiotics* (Tokyo) (1991) 44(6):688-90; and *Tetrahedron Letters* (1992) 33(33):4139-4142. Rapamycin and its derivatives also exist as a mixture of cis- and trans-amides shown below as E, H, J and K (Schemes 4 and 5). [See Werke, D. F., Schmieder, P., Karuso, P. and Kessler, H. (1991), Conformational Analysis of the cis- and trans-isomers of FK506 by NMR and Molecular Dynamics. *Helvetica Chimica Acta*, 74: 1027-1047.] The NMR characterization data shown in the examples corresponds only to the major equilibrium form observed under the reported deutero solvent conditions.

Scheme 4
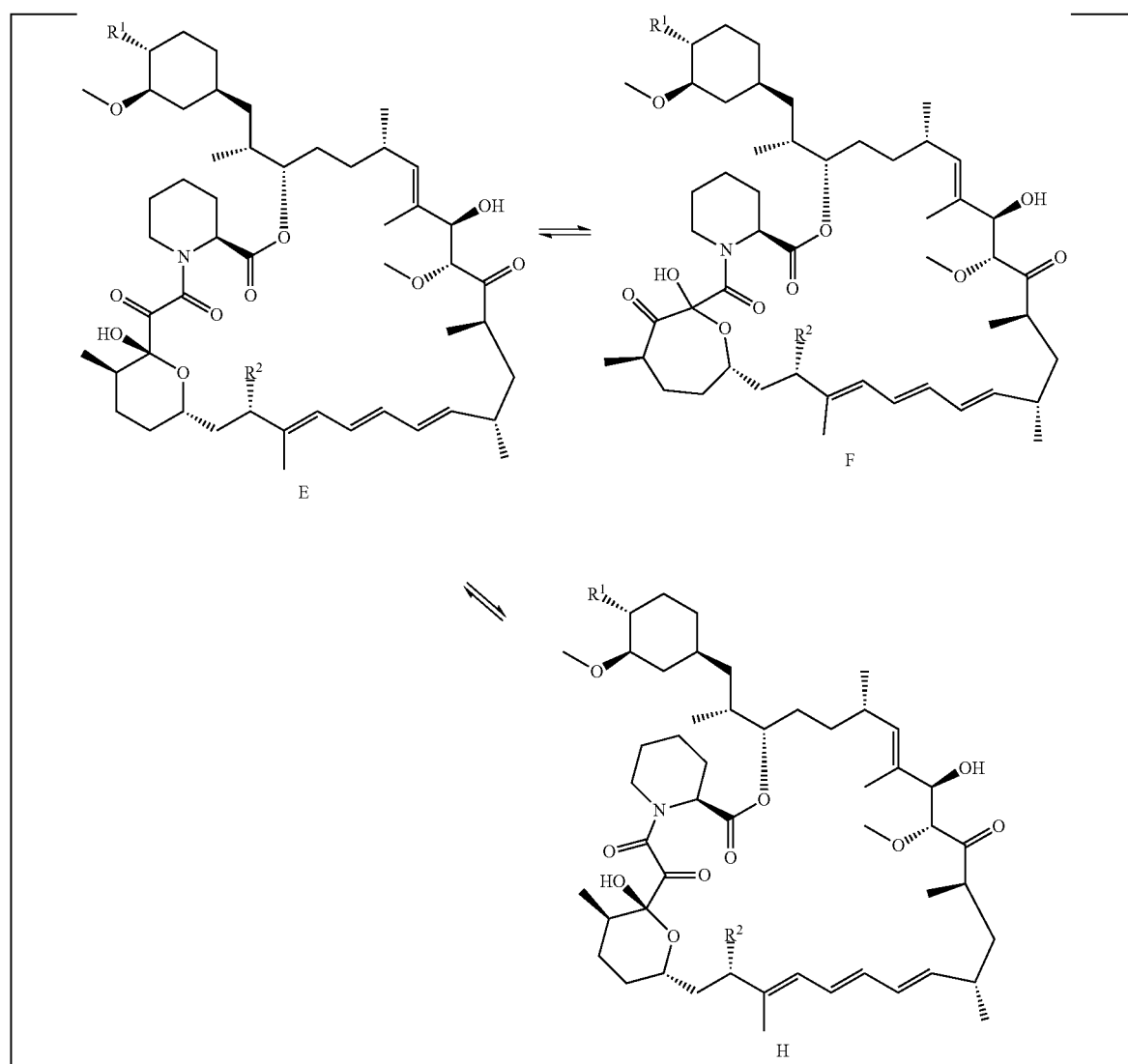
wherein:
$R_1$ is selected from the group consisting of hydroxy,
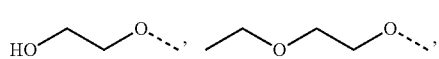
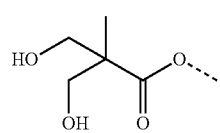
and, and
$R_2$ is selected from the group consisting of
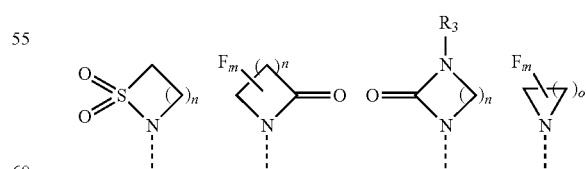
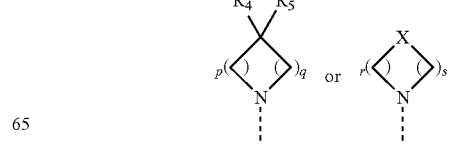

wherein
- m is 0, 1, 2 or 3;
- n is 1, 2 or 3;
- is 1, 2, 3, 4, 5 or 6;
- p is 1, 2, 3, 4 or 5
- q is 1, 2, 3, 4 or 5 wherein the sum of p and q is 2, 3, 4, 5 or 6;
- r is 2, 3 or 4;
- s is 2, 3 or 4 wherein the sum of r and s is 4, 5 or 6;
- X is O, S, $NR_6$ or $SO_2$;
- $R_3$ is hydrogen, $C_{1-6}$alkyl, hydroxy$C_{1-6}$alkyl, $C_{3-8}$cycloalkyl$C_{0-6}$alkyl or phenyl$C_{0-6}$alkyl;
- $R_4$ is hydrogen and $R_5$ is hydrogen, hydroxy or cyano or $R_4$ and $R_5$ together form =O; and
- $R_6$ is hydrogen, $C_{1-6}$alkyl, $C_{3-8}$cycloalkyl$C_{0-6}$alkyl, phenyl$C_{0-6}$alkyl, $C_{1-6}$alkyl-CO—, $C_3$-acycloalkyl$C_{0-6}$alkyl-CO—, $C_{1-6}$alkyl-$SO_2$— or $C_{3-8}$cycloalkyl$C_{0-6}$alkyl-$SO_2$—.

In an embodiment, $R_1$ is hydroxy.

In an embodiment, $R_2$ is and n is 1, 2 or 3. In an embodiment, $R_2$ is

Scheme 5

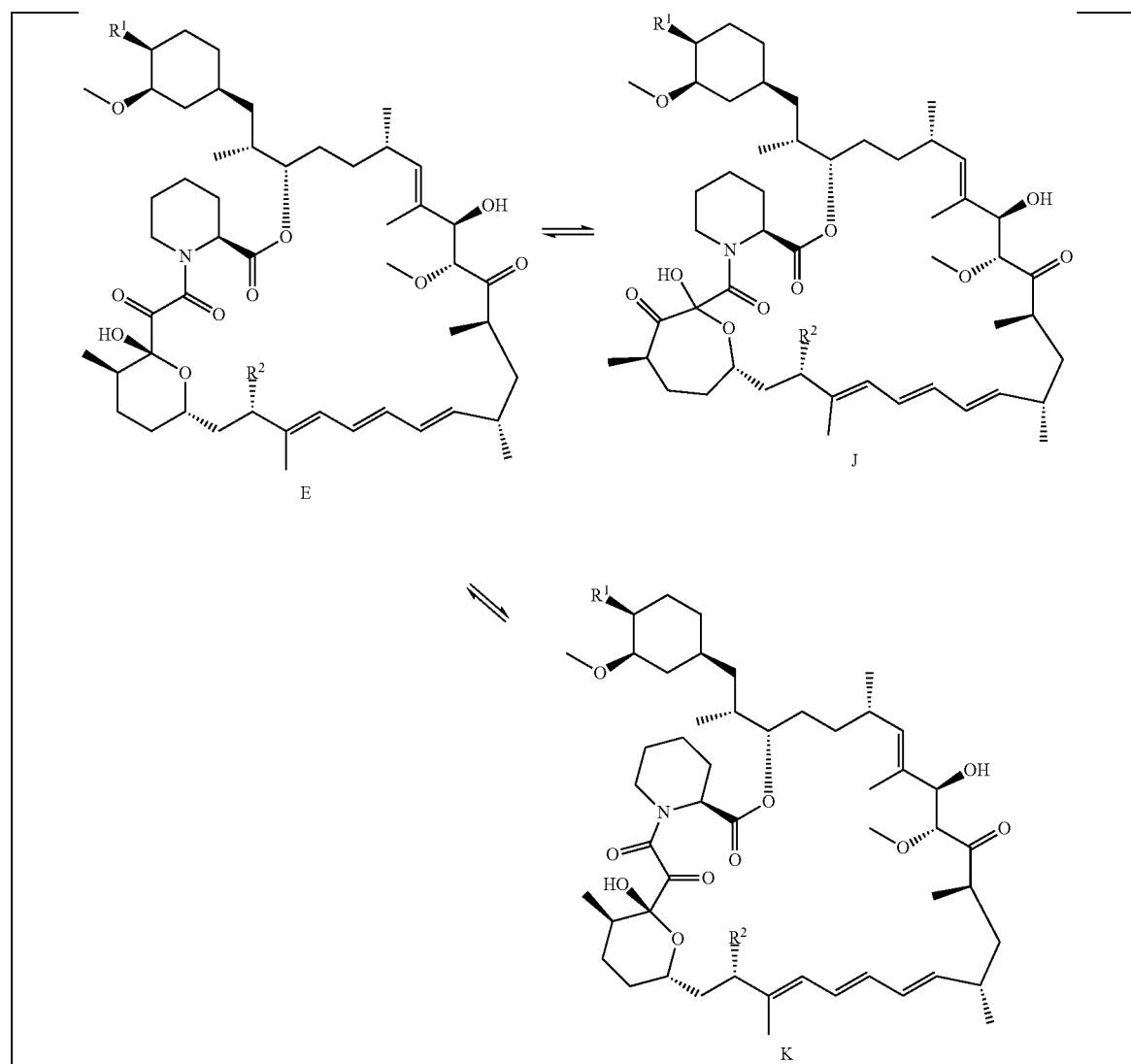

wherein:
R₁ is

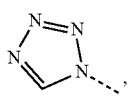

and
R₂ is selected from the group consisting of

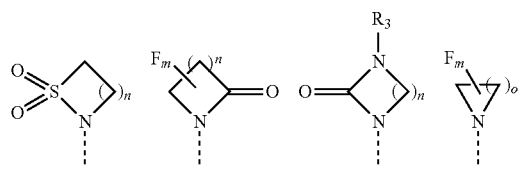

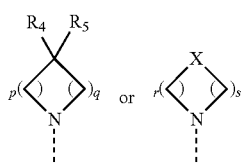

wherein
m is 0, 1, 2 or 3;
n is 1, 2 or 3;
is 1, 2, 3, 4, 5 or 6;
p is 1, 2, 3, 4 or 5
q is 1, 2, 3, 4 or 5 wherein the sum of p and q is 2, 3, 4, 5 or 6;
r is 2, 3 or 4;

s is 2, 3 or 4 wherein the sum of r and s is 4, 5 or 6;
X is O, S, NR₆ or SO₂;
R₃ is hydrogen, $C_{1-6}$alkyl, hydroxy$C_{1-6}$alkyl, $C_{3-8}$cycloalkyl$C_{0-6}$alkyl or phenyl$C_{0-6}$alkyl;
R₄ is hydrogen and R₅ is hydrogen, hydroxy or cyano or R₄ and R₅ together form =O; and
R₆ is hydrogen, $C_{1-6}$alkyl, $C_{3-8}$cycloalkyl$C_{0-6}$alkyl, phenyl$C_{0-6}$alkyl, $C_{1-6}$alkyl-CO—, $C_3$-acycloalkyl$C_{0-6}$alkyl-CO—, $C_{1-6}$alkyl-SO₂— or $C_{3-8}$cycloalkyl$C_{0-6}$alkyl-SO₂—.

In an embodiment, R₂ is

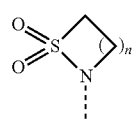

and n is 1, 2 or 3. In an embodiment, R₂ is

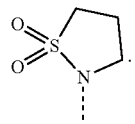

In an embodiment, compounds of formula (I), formula (I)-A and formula (I)-B exist as a solvent and pH dependent equilibrium of six-membered and seven-membered hemiketal forms shown below as E-1 and F-1 (Scheme 6). In an embodiment, compounds of formula (I), formula (I)-A and formula (I)-B exist as a mixture of cis- and trans-amides E-1 and H-1.

Scheme 6

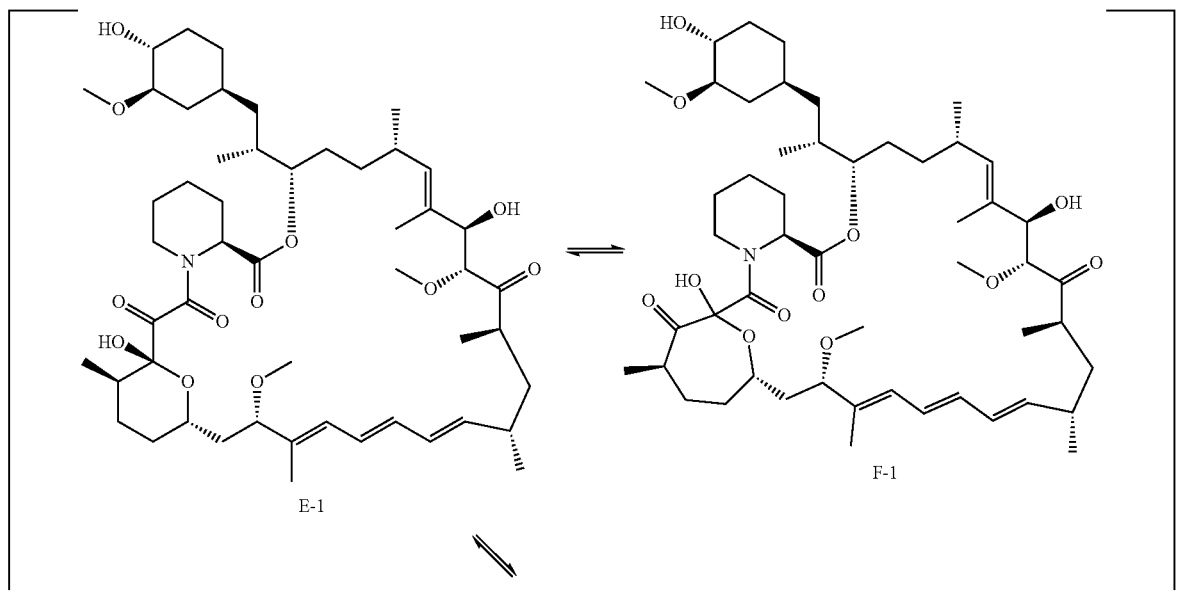

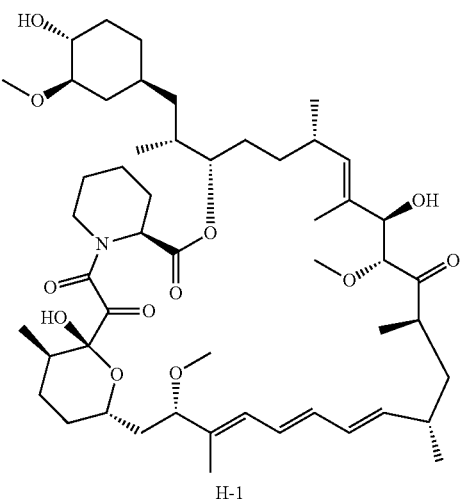

H-1

Preparation of Compounds

Compounds of the disclosure can be prepared as described in the following Examples.

Abbreviations

4-EP 4-ethyl pyridine
AcOH acetic acid
ACN acetonitrile
Aq aqueous
C Celsius
d doublet
dd doublet of doublets
DCM dichloromethane
DIPEA N,N-diisopropylethylamine
DMSO dimethylsulfoxide
EDTA ethylenediaminetetraacetic acid
ESIMS Electrospray ionization mass spectrometry
EtOAc ethyl acetate
EtOH ethanol
FA formic acid
g gram
h hour(s)
HPLC high performance liquid chromatography
HRMS High resolution Mass Spectrometry
iPrOH 2-propanol or isopropanol
L liter
LC liquid chromatography
LCMS liquid chromatography and mass spectrometry
MeOH methanol
MS mass spectrometry
M molar
m multiplet
min minutes
mL milliliter(s)
μM micromolar
m/z mass to charge ratio
$N_2$ nitrogen gas
nM nanomolar
NMR nuclear magnetic resonance
$^1$HNMR: Proton Nuclear Magnetic Resonance spectroscopy
PEI Polyethylenimine
PPU Propyl-pyridyl-urea
pTsOH p-toluenesulfonic acid
prep preparative
rac racemic
rpm revolutions per minute
r.t. room temperature
s singlet
sat. saturated
SFC Supercritical Fluid Chromatography
t triplet
TCEP tris(2-carboxyethyl)phosphine
TFA trifluoroacetic acid
THF tetrahydrofuran
TLC thin layer chromatography
vol. volume Methods Employed in the Purification of the Examples Purification of intermediates and final products was carried out via either normal or reverse phase chromatography.

Normal phase chromatography was carried out using prepacked $SiO_2$ cartridges (e.g., RediSep® Rf columns from Teledyne Isco, Inc.) eluting with gradients of appropriate solvent systems (e.g., hexanes and ethyl acetate; DCM and MeOH; or unless otherwise indicated).

SFC was carried out using the methods described below:
Method 1: Princeton PPU 5 μm (100 A) column (30×250 mm); $CO_2$/MeOH
Method 2: Princeton 4-EP 5 μm (60 A) column (30×250 mm); $CO_2$/MeOH
Method 3: Reprospher PEI 5 μm (100 A) column (30×250 mm); $CO_2$/MeOH Gradients were selected based on analytical separation.
Reverse phase preparative HPLC was carried out using the methods described below:
Method 1: (Agilent) Phenomenex Luna C18; 5 μm column (30×250 mm); 0.1% formic acid and 5% water in acetonitrile; 0.1% formic acid and 5% acetonitrile in water.
Gradients were selected based on analytical separation.
Method 2: (EZprep) YMC Actus Triart C18; 5 μm column (20×150 mm); acetonitrile/water.
Gradients were selected based on analytical separation.
Chiral preparative HPLC was carried out using the methods described below:
Method 1: Chiralpak IC; 5 μm column (20×250 mm); n-Heptane/DCM/EtOH Method 2: Chiralpak ID; 5 μm column (20×250 mm); n-Heptane/DCM/iPrOH Gradients were selected based on analytical separation.

LC/MS Method:

Column: Acquity UPLC BEH C18, 130 Angstrom, 1.7 uM, 2.1 mm×50 mm

Temperature: 50° C.

Injection: 1 uL

Solvent A: water+5 mM ammonium hydroxide

Solvent B: acetonitrile+5 mM ammonium hydroxide

Gradient:

| Time (min) | Flow Rate | A % | B % | Curve |
| --- | --- | --- | --- | --- |
| Initial | 1.000 | 98.0 | 2.0 | Initial |
| 4.40 | 1.0 | 2.0 | 98.0 | 6 |
| 5.15 | 1.0 | 2.0 | 98.0 | 6 |
| 5.19 | 1.0 | 98.0 | 2.0 | 6 |

$^1$H NMR Instruments:

Bruker UltraShield™ Advance III HD 400 MHz with a cryo-DCI probe. Data were processed with MestReNova 11.0 software.

Preparation of Intermediates 1 to 7

Intermediate 1: C32-deoxo-rapamycin

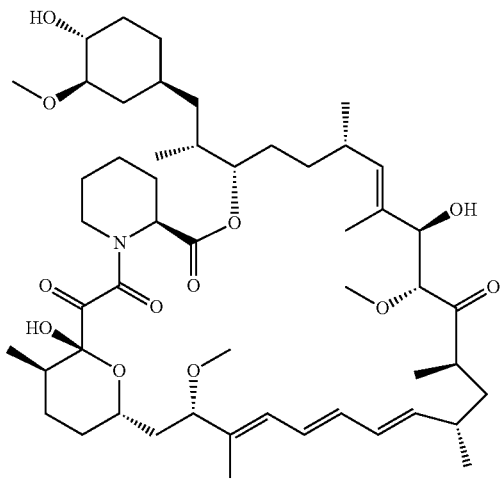

Intermediate 1

Intermediate 1 was prepared according to procedures known in the literature including those disclosed in US Patent Publication No. 005985890 and WO2007/085400 A1, each of which is incorporated by reference herein in its entirety.

Intermediate 2: RAD001 (Everolimus; Afinitor®)

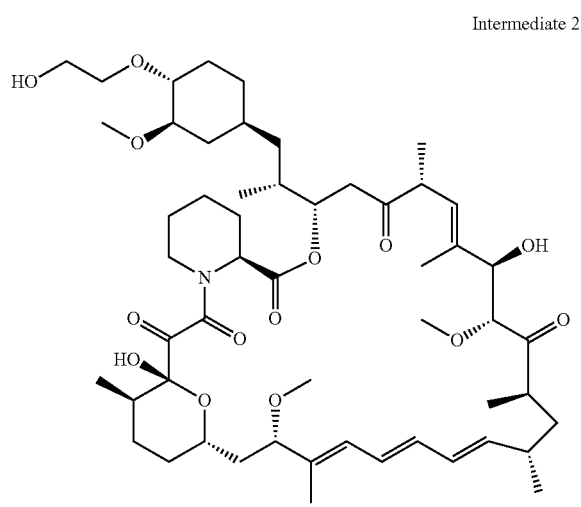 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCO)[C@H](OC)C2)CC(=O)[C@H](C)/C=C(\C)[C@@H](O)[C@@H](OC)C(=O)[C@H](C)C[C@H](C)/C=C/C=C/C=C/1C]

Intermediate 2

Intermediate 2 was prepared according to procedures known in the literature including those disclosed in WO2012103959, which is incorporated herein by reference herein in its entirety.

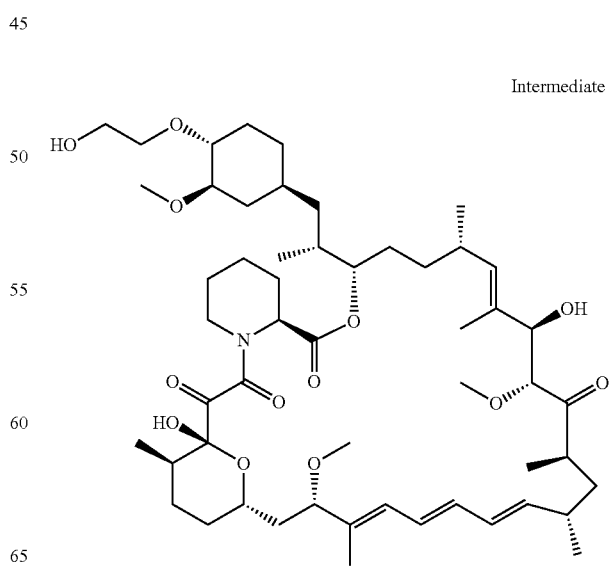

Intermediate 3

Intermediate 3

Intermediate 3 was prepared in two steps through Intermediate A as shown below:

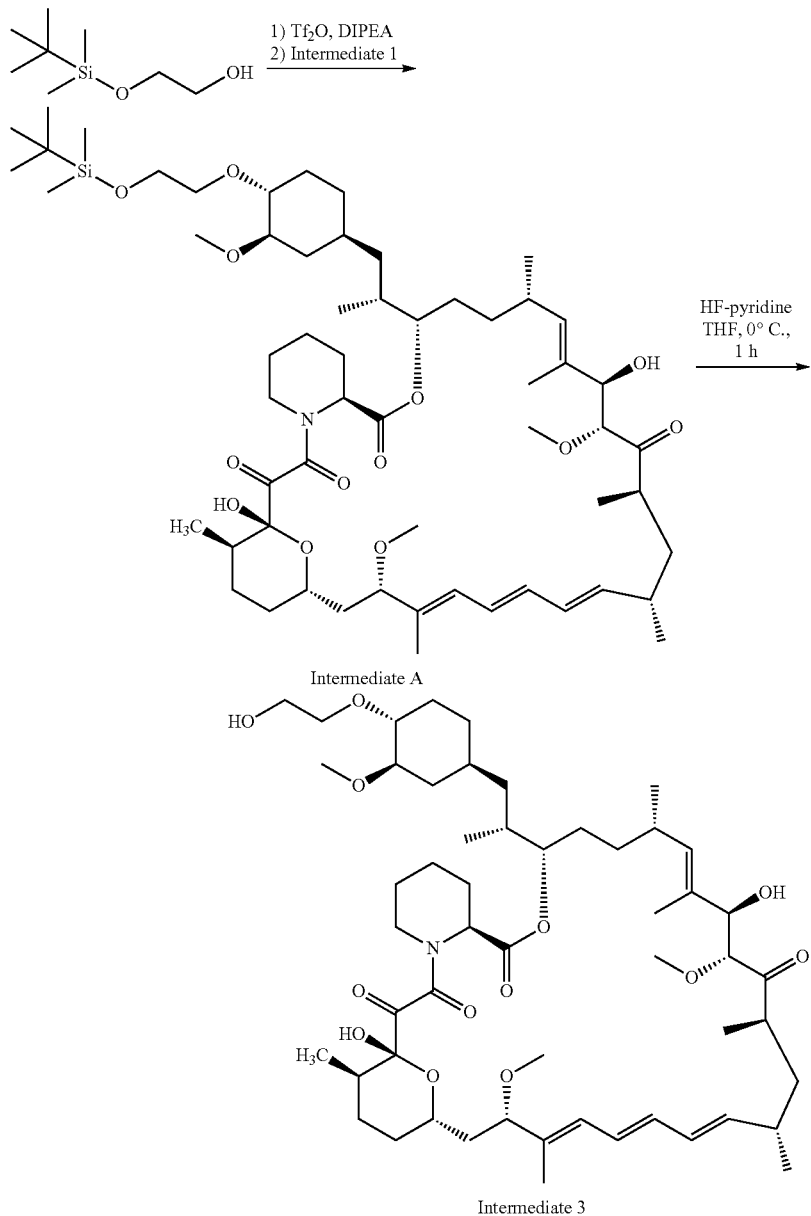

Step 1. Synthesis of Intermediate A 2-((tert-butyldimethylsilyl)oxy)ethanol (0.471 g, 2.67 mmol) was dissolved in anhydrous toluene (0.95 mL) in a reaction vial. The vial was capped and then was vacuum purged with nitrogen. N,N-diisopropylethylamine (DIPEA) (0.490 ml, 2.81 mmol) was added via syringe. The mixture was chilled to 0° C. in an ice-water bath. Triflic anhydride (Tf$_2$O) (0.438 ml, 2.59 mmol) was added dropwise at 0° C. over a period of about two minutes. The reaction mixture was stirred at 0° C. for 30 minutes.

The vial was lifted out of the cold bath. DIPEA (0.490 ml, 2.81 mmol) was added via syringe. The vial was opened and solid Intermediate 1 (0.600 g, 0.667 mmol) was quickly added in one portion. The vial was quickly recapped and the mixture was vacuum purged with nitrogen. Toluene (0.5 mL) was added.

The reaction was stirred at 40° C. under nitrogen overnight. The reaction was diluted with saturated aqueous NaHCO$_3$. The quenched mixture was extracted with EtOAc five times. The organic extracts were combined, dried over Na$_2$SO$_4$, vacuum filtered through celite and concentrated to afford a waxy white solid crude product.

The crude product was purified by silica gel flash column chromatography (0-35% acetone-heptane, gradient elution, 40 g silica column, TLC in 35% acetone-heptane, visualize under UV) to give the desired intermediate A (0.245 g, 0.231 mmol, 34.7% yield) as a glass which was immediately used "as is" in the following step.

Intermediate A: ESIMS [M+NH4] 1076.1, ESIMS [M−H] 1056.0.

Step 2. Synthesis of Intermediate 3

Intermediate A (0.135 g, 0.128 mmol) was dissolved in anhydrous THF (1.2 mL) in a glass reaction vial. The vial was capped and the mixture was vacuum purged twice with nitrogen. The mixture was chilled to 0° C. in an ice-water bath. HF-Pyridine (0.12 mL, 1.332 mmol) was added dropwise via syringe over a period of 30 seconds. The reaction was stirred at 0° C. for 60 minutes.

The reaction mixture was added dropwise to a saturated aqueous NaHCO₃ solution. The quenched mixture was extracted five times with EtOAc. The organic extracts were combined, dried over Na₂SO₄, vacuum filtered through celite and concentrated to afford a white solid crude product.

The crude product was purified by silica gel flash column chromatography (0-50% Acetone-heptane gradient elution, 40 g silica column, TLC in 50% Acetone-heptane, visualize under UV) to give Intermediate 3 (0.087 g, 0.092 mmol, 72.2% yield) as a white solid.

Intermediate 3: ESIMS [M+NH4] 962.0, ESIMS [M−H] 943.0

¹H NMR (400 MHz, Chloroform-d) δ 6.46-6.25 (m, 2H), 6.19-6.09 (m, 1H), 5.91 (m, 1H), 5.55 (m, 1H), 5.34-5.26 (m, 1H), 5.26-5.15 (m, 1H), 4.88-4.64 (m, 2H), 4.11 (m, 1H), 3.94-3.82 (m, 1H), 3.79 (m, 1H), 3.73-3.63 (m, 3H), 3.63-3.47 (m, 4H), 3.45 (m, 4H), 3.33 (m, 3H), 3.28-3.15 (m, 2H), 3.13 (s, 3H), 3.08 (m, 1H), 2.80 (m, 1H), 2.32 (m, 3H), 2.14 (m, 2H), 2.07-1.94 (m, 2H), 1.94-1.72 (m, 5H), 1.72-1.56 (m, 8H), 1.56-1.40 (m, 3H), 1.39-1.21 (m, 7H), 1.21-1.09 (m, 1H), 1.08-0.99 (m, 8H), 0.98-0.83 (m, 9H), 0.73 (q, J=12.0 Hz, 1H).

Intermediate 4

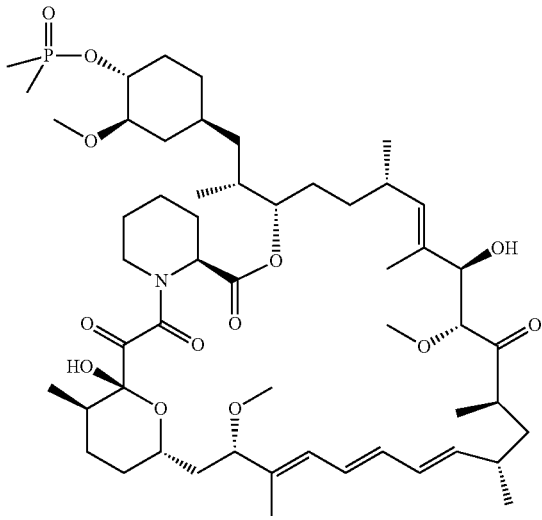

Intermediate 1 (0.233 g, 0.259 mmol) was combined with 2,6-di-tert-butyl-4-methylpyridine (0.425 g, 2.071 mmol) in anhydrous dichloromethane (2.6 mL). The reaction mixture was vacuum purged once with nitrogen. The reaction mixture was chilled to 0° C. in an ice-water bath. Solid dimethylphosphinic chloride (0.146 g, 1.294 mmol) was added in one portion. The reaction mixture was stirred at 0° C. for 80 minutes.

The reaction was diluted with saturated aqueous NaHCO3 and was extracted several times with EtOAc. The organic extracts were combined, dried over Na₂SO₄, decanted and concentrated to give a colorless tar crude product (0.768 g).

The crude product was purified by silica gel flash column chromatography (0-80% Acetone-heptane gradient elution, 24 g silica column, TLC in 80% EtOAc-heptane, visualize under UV). Product containing fractions were pooled and concentrated to give Intermediate 4 (0.087 g, 0.089 mmol, 34.4% yield) as a white solid.

Intermediate 4: ESIMS [M+NH4] 993.7, ESIMS [M−H] 974.7.

HRMS: Calculated: 999.5812 (as sodium adduct). Found: 999.5807.

¹H NMR (600 MHz, Chloroform-d) δ 6.47-6.26 (m, 2H), 6.22-6.08 (m, 1H), 6.02-5.83 (m, 1H), 5.54 (m, 1H), 5.35-5.26 (m, 1H), 5.21 (m, 1H), 4.85-4.76 (m, 1H), 4.12 (m, 2H), 3.93-3.81 (m, 1H), 3.67 (t, J=7.7 Hz, 1H), 3.62 (d, J=6.7 Hz, 1H), 3.60-3.53 (m, 1H), 3.53-3.44 (m, 1H), 3.42-3.36 (m, 3H), 3.32 (m, 3H), 3.28-3.18 (m, 1H), 3.13 (m, 3H), 3.05 (m, 1H), 2.82 (m, 1H), 2.42-2.21 (m, 3H), 2.16-2.08 (m, 3H), 1.99 (m, 1H), 1.95-1.83 (m, 1H), 1.83-1.72 (m, 4H), 1.71-1.57 (m, 9H), 1.57-1.43 (m, 12H), 1.39 (m, 1H), 1.34-1.20 (m, 4H), 1.20-1.10 (m, 1H), 1.05 (m, 4H), 1.00 (d, J=6.5 Hz, 3H), 0.95 (dd, J=6.6, 2.1 Hz, 3H), 0.92 (d, J=6.6 Hz, 3H), 0.91-0.84 (m, 4H), 0.77 (q, J=12.1 Hz, 1H).

Intermediate 5

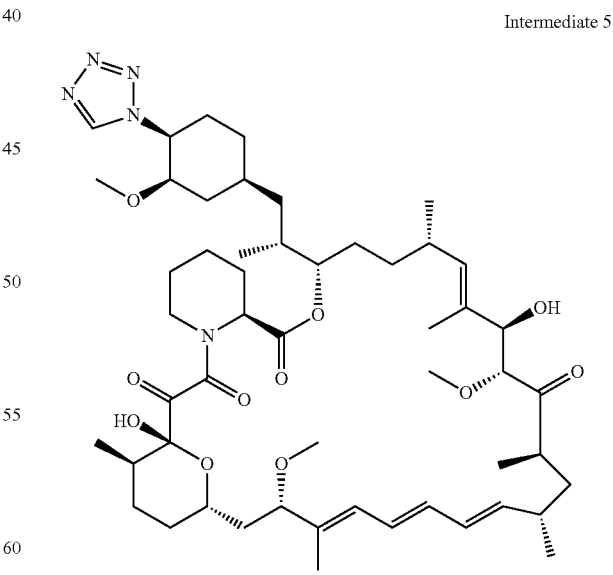

Intermediate 1 (4.372 g, 4.86 mmol) was dissolved in anhydrous dichloromethane (20 mL). Anhydrous toluene was added (20 mL). The reaction mixture was evaporated to dryness on a rotary evaporator. This azeotropic drying process was repeated twice more.

The dried starting material was combined with 2,6-lutidine (1.388 ml, 11.91 mmol) in anhydrous dichloromethane (58 mL). The flask was capped and the mixture was twice vacuum purged with nitrogen. The mixture was chilled to −30 C in an acetonitrile/dry-ice bath.

Triflic anhydride (1.209 ml, 7.16 mmol) was added dropwise via syringe over a period of four minutes. The reaction mixture was stirred at −30° C. for 30 minutes. The reaction mixture was transferred to a 0° C. ice-water bath and was stirred for 20 minutes at 0° C.

The reaction mixture was placed on the rotary evaporator and was concentrated without heat. Isopropyl acetate (22 mL) was added. Tetrazole (1.170 g, 16.71 mmol) was added in one portion. The flask was quickly capped and was twice vacuum purged with nitrogen. N,N-diisopropylethylamine (4.18 ml, 23.94 mmol) was added via syringe over a period of one minute. The reaction mixture was stirred overnight at room temperature.

The reaction mixture was concentrated on a rotary evaporator. The concentrate was purified by normal-phase silica gel flash column chromatography (0 to 40% acetone-heptane gradient elution, 80 g silica column, TLC 40% acetone-heptane, visualize under UV).

The second eluting peak fractions (as determined by UV absorbance at 279 nm) were pooled and concentrated to give Intermediate 5 (2.194 g, 2.304 mmol, 47.4% yield) as a white solid.

Intermediate 5: ESIMS [M+NH4] 969.8, ESIMS [M−H] 950.8.

$^1$H NMR (400 MHz, DMSO-d$_6$) δ 9.33 (d, J=6.4 Hz, 1H), 6.58-6.41 (m, 2H), 6.35-6.14 (m, 2H), 6.09-5.98 (m, 1H), 5.55-5.43 (m, 1H), 5.19 (m, 1H), 5.05 (m, 1H), 5.00-4.93 (m, 1H), 4.87-4.79 (m, 1H), 4.67-4.56 (m, 1H), 3.98-3.87 (m, 1H), 3.87 (d, J=6.9 Hz, 1H), 3.61 (m, 2H), 3.55 (dd, J=11.8, 1.9 Hz, 1H), 3.49-3.38 (m, 1H), 3.31-3.17 (m, 4H), 3.10 (m, 4H), 3.04 (s, 3H), 2.88-2.75 (m, 1H), 2.29-2.09 (m, 3H), 2.07-1.86 (m, 3H), 1.88-1.60 (m, 9H), 1.59-1.44 (m, 7H), 1.43-1.01 (m, 11H), 0.96 (t, J=7.1 Hz, 5H), 0.95-0.77 (m, 7H), 0.72 (m, 4H).

Intermediate 6

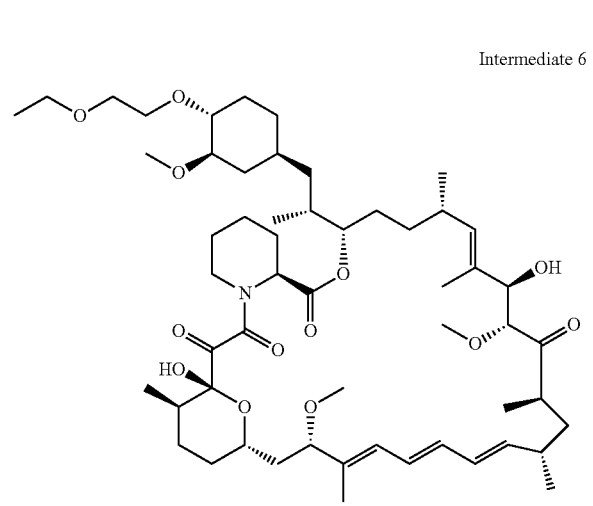 [SMILES: CCOCCO[C@@H]1CC[C@@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](OC)C[C@@H]3CC[C@@H](C)[C@@](O)(O3)C(=O)C(=O)N3CCCC[C@H]3C(=O)O2)C[C@H]1OC]

2-ethoxyethanol (0.538 ml, 5.55 mmol) was combined in anhydrous toluene (2.0 mL) and anhydrous dioxane (0.22 mL). N,N-diisopropylethylamine (1.067 ml, 6.11 mmol) was added via syringe. The reaction mixture was twice vacuum purged with nitrogen. The mixture was chilled to 0° C. in an ice-water bath.

Triflic anhydride (0.901 ml, 5.33 mmol) was added dropwise via syringe over a period of two minutes. The reaction was stirred at 0° C. for 15 minutes. The cold bath was removed and the reaction was allowed to equilibrate to room temperature over 15 minutes.

N,N-diisopropylethylamine (1.067 ml, 6.11 mmol) was added dropwise via syringe over a period of 30 seconds. Intermediate 1 (1.00 g, 1.111 mmol) was added in one portion.

The reaction mixture was quickly capped and vacuum purged with nitrogen. Anhydrous toluene (2.0 mL) and anhydrous dioxane (0.22 mL) were added via syringe. The reaction mixture was stirred at 55° C. for 24 hours.

The reaction mixture was diluted with brine and was extracted several times with EtOAc. The organic extracts were combined, dried over Na$_2$SO$_4$, decanted and concentrated to give a colorless tar crude product (4.25 g).

The crude product was purified by silica gel flash column chromatography (0-50% Acetone-heptane gradient elution, 80 g silica column, TLC in 40% Acetone-heptane, visualize under UV). Product containing fractions were pooled and concentrated to give Intermediate 6 (0.443 g, 0.456 mmol, 41.0% yield) as a colorless glass.

Intermediate 6: ESIMS [M−H] 970.9.

HRMS: calculated—989.6678 (as ammonium adduct); found—989.6655 calculated—994.6232 (as sodium adduct); found—994.6215.

Intermediate 7

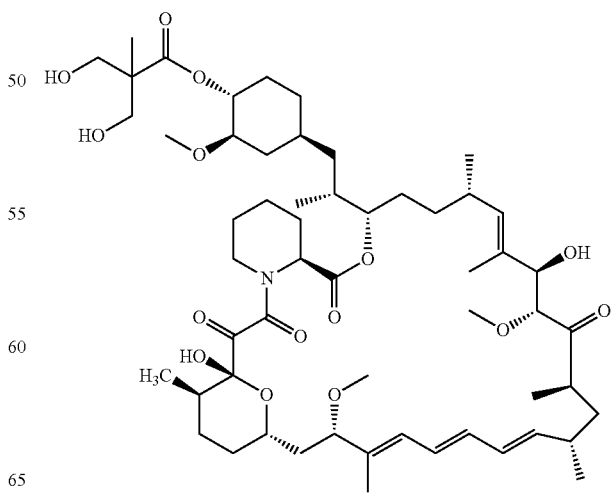

Intermediate 7 was prepared in two steps through Intermediate B as shown below:

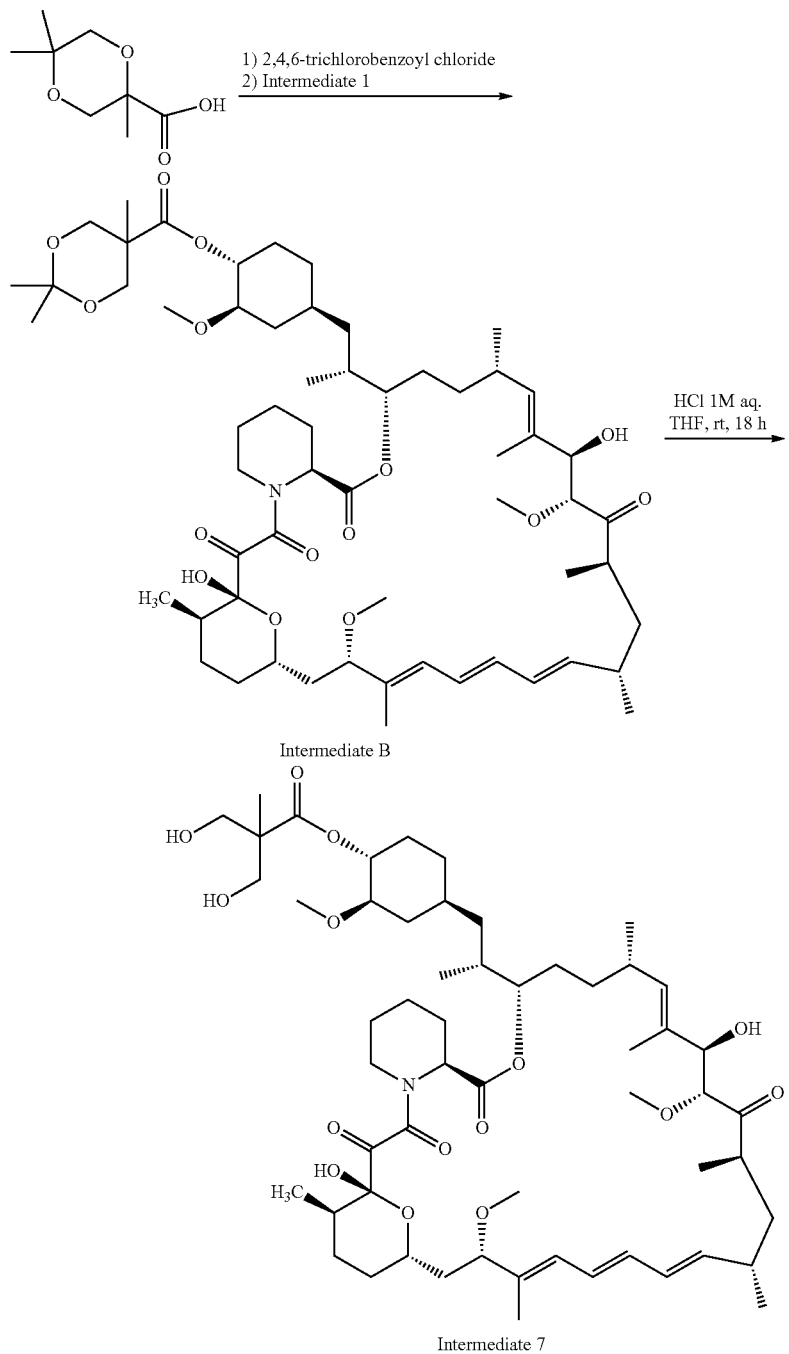

Step 1. Synthesis of Intermediate B 2,2,5-trimethyl-1,3-dioxane-5-carboxylic acid (0.400 g, 2.296 mmol) and triethylamine (0.320 ml, 2.296 mmol) were combined dissolved in anhydrous THF (7.6 mL). The reaction mixture was chilled to 0° C. 2,4,6-Trichlorobenzoyl chloride (0.359 ml, 2.296 mmol) was added via syringe. The reaction was stirred at 0° C. for ten minutes. The cold bath was removed and the reaction was stirred at room temperature for 2.5 hours. A white solid precipitated.

The reaction mixture was filtered through a syringe filter. The filter was rinsed with THF (2 mL). The filtrates were combined and concentrated on the rotary evaporator leaving a colorless tar.

To the concentrate, toluene (7.6 mL) was added. Intermediate 1 (1.447 g, 1.607 mmol) was added in one portion followed by 4-dimethylaminopyridine (0.281 g, 2.296 mmol). The reaction mixture was stirred at room temperature overnight.

The mixture was diluted with water and was extracted four times with EtOAc. The organic extracts were combined, dried over Na$_2$SO$_4$, decanted and concentrated to give a yellow tar crude product (2.15 g).

The crude product was purified by silica gel flash column chromatography (0-40% Acetone-heptane gradient elution, 40 g silica column, TLC in 40% Acetone-heptane, visualize under UV). Product containing fractions were pooled and concentrated to give Intermediate B (0.438 g, 0.415 mmol, 18.1% yield) as a white foam.

Intermediate B: ESIMS [M+NH4] 1074.0, ESIMS [M−H] 1055.1.

Step 2. Synthesis of Intermediate 7

Intermediate B (0.431 g, 0.408 mmol) was dissolved in THF (4 mL). HCl (1M, aq.) (2.0 ml, 2.00 mmol) was added via syringe. The reaction was stirred at room temperature for 36 hours.

The reaction mixture was diluted with water and was extracted four times with EtOAc. The organic extracts were combined, dried over Na$_2$SO$_4$, decanted and concentrated to give a faint yellow tar. The tar was dissolved in dichloromethane and was diluted with heptane. The mixture was concentrated and dried on high vacuum to give Intermediate 7 (0.407 g, 0.400 mmol, 98% yield) as a white solid.

Intermediate 7: ESIMS [M+NH4] 1034.0, ESIMS [M−H] 1015.0.

HRMS calculated—1033.6576 (as ammonium adduct); found—1033.6588 calculated—1038.6130 (as sodium adduct); found—1038.6138.

Example 1: (S)—C16-(1,1-dioxidoisothiazolidin-2-yl)-C32-deoxo-rapamycin

Example 2: (R)—C16-(1,1-dioxidoisothiazolidin-2-yl)-C32-deoxo-rapamycin

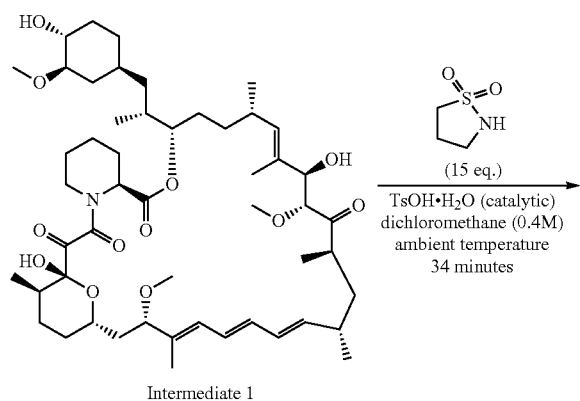

Intermediate 1

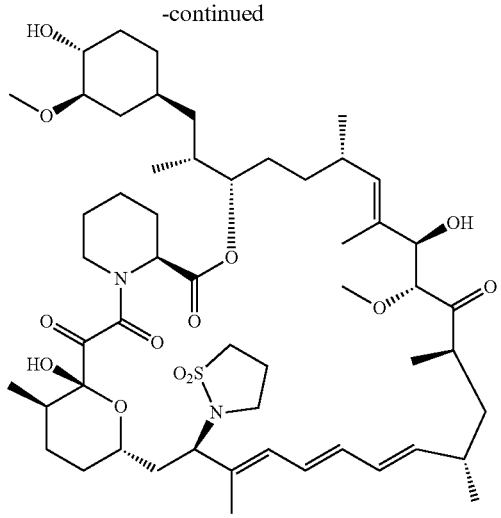

Example 1 (S)-diastereomer at C16
Example 2 (R)-diastereomer at C16 (depicted)

To a stirring solution of Intermediate 1 (2.0 g, 2.222 mmol) and isothiazolidine 1,1-dioxide (4.04 g, 33.3 mmol, 15 equivalents) in anhydrous dichloromethane (5.6 mL) was added p-toluenesulphonic acid. H$_2$O (0.042 g, 0.222 mmol, 0.1 equivalent) in one portion. The reaction was stirred at ambient temperature under a nitrogen atmosphere for 34 minutes. The entire reaction mixture was directly chromatographed by over silica (gradient elution from 100% heptane to 40% acetone-heptane) to give a product mixture of both diastereomers in a ratio of about 3:1 by UV absorbance at 279 nm on LC/MS analysis.

The diastereomeric mixture was separated by normal phase chromatography on silica (gradient elution from 100% dichloromethane to 40% acetonitrile-dichloromethane).

The first eluting diastereomer (Rf~0.23 on silica TLC developed in 30% acetonitrile-dichloromethane) affords Example 1 (S)-diastereomer as a white solid.

Example 1: ESIMS [M+NH4] 1006.7, ESIMS [M−H] 987.8

$^1$H NMR (600 MHz, Chloroform-d) δ 6.43 (dd, J=14.9, 10.4 Hz, 1H), 6.35 (dd, J=14.9, 10.7 Hz, 1H), 6.16 (dd, J=15.1, 10.2 Hz, 1H), 6.06-6.01 (m, 1H), 5.67 (dd, J=15.2, 8.6 Hz, 1H), 5.35 (dd, J=6.4, 1.8 Hz, 1H), 5.26 (d, J=9.6 Hz, 1H), 4.83 (td, J=6.6, 4.7 Hz, 1H), 4.12 (d, J=7.4 Hz, 1H), 3.88 (dd, J=11.1, 5.1 Hz, 1H), 3.84-3.77 (m, 1H), 3.63-3.60 (m, 2H), 3.51 (d, J=7.5 Hz, 1H), 3.46 (s, 3H), 3.45-3.42 (m, 3H), 3.35 (s, 3H), 3.29-3.14 (m, 3H), 3.06-2.96 (m, 2H), 2.93 (ddd, J=10.4, 6.4, 1.5 Hz, 1H), 2.44 (tt, J=8.6, 6.2 Hz, 1H), 2.37-2.23 (m, 4H), 2.22-2.14 (m, 2H), 2.03 (dt, J=12.3, 3.8 Hz, 1H), 1.96 (pd, J=6.4, 5.7, 3.5 Hz, 2H), 1.92-1.82 (m, 3H), 1.80-1.76 (m, 2H), 1.75 (d, J=1.2 Hz, 4H), 1.72 (d, J=3.1 Hz, 1H), 1.68 (d, J=1.3 Hz, 3H), 1.65-1.53 (m, 4H), 1.48-1.17 (m, 9H), 1.07 (d, J=6.5 Hz, 1H), 1.06 (s, 3H), 1.04 (d, J=7.3 Hz, 3H), 1.01 (d, J=6.6 Hz, 3H), 0.99 (dd, J=6.7, 2.3 Hz, 3H), 0.95 (d, J=6.8 Hz, 3H), 0.74 (q, J=11.9 Hz, 1H).

The second eluting diastereomer (Rf~0.16 on silica TLC developed in 30% acetonitrile-dichloromethane) affords Example 2 (R)-diastereomer as a white solid Example 2: ESIMS [M+NH4] 1006.9, ESIMS [M−H] 988.1

$^1$H NMR (Chloroform-d) δ 6.48 (dd, J=14.7, 10.9 Hz, 1H), 6.24 (dd, J=14.6, 10.6 Hz, 1H), 6.16 (dd, J=14.9, 10.6 Hz, 1H), 6.01 (d, J=11.0 Hz, 1H), 5.38 (dd, J=14.9, 9.8 Hz, 1H), 5.23 (dd, J=6.2, 2.0 Hz, 1H), 5.12 (d, J=9.9 Hz, 1H), 4.73 (dd, J=12.1, 2.9 Hz, 1H), 4.65 (dt, J=8.3, 3.9 Hz, 1H), 4.14 (d, J=6.7 Hz, 1H), 3.97 (m, 1H), 3.74 (d, J=6.7 Hz, 1H), 3.62 (qd, J=13.9, 12.7, 5.5 Hz, 2H), 3.42 (s, 3H), 3.39 (m, 1H), 3.31 (s, 3H), 3.24 (ddd, J=12.2, 7.5, 4.6 Hz, 1H), 3.10 (td, J=8.2, 3.8 Hz, 1H), 3.08 (s, 1H), 3.02-2.97 (m, 1H), 2.97-2.92 (m, 1H), 2.83-2.71 (m, 1H), 2.42 (ddt, J=13.1, 9.5, 6.4 Hz, 1H), 2.34 (d, J=4.3 Hz, 1H), 2.31 (s, 1H), 2.28-2.23 (m, 1H), 2.22-2.19 (m, 1H), 2.19 (s, 2H), 2.12-2.08 (m, 2H), 2.03-1.99 (m, 1H), 1.90 (s, 3H), 1.88 (s, 1H), 1.79 (s, 1H), 1.77 (s, 1H), 1.76 (s, 1H), 1.72-1.68 (m, 1H), 1.48 (s, 1H), 1.46 (s, 1H), 1.40 (d, J=3.0 Hz, 1H), 1.38 (s, 1H), 1.66 (d, J=3.0 Hz, 2H), 1.64 (d, J=2.9 Hz, 1H), 1.62 (s, 2H), 1.62 (s, 2H), 1.58-1.53 (m, 1H), 1.37 (s, 1H), 1.36 (d, J=2.3 Hz, 1H), 1.33 (d, J=2.9 Hz, 1H), 1.30 (dd, J=6.7, 1.8 Hz, 1H), 1.28 (s, 2H), 1.28 (s, 2H), 1.24 (s, 1H), 1.09 (s, 1H), 1.07 (d, J=6.6 Hz, 3H), 1.05 (d, J=6.6 Hz, 3H), 1.01 (d, J=3.2 Hz, 1H), 0.95 (d, J=6.8 Hz, 3H), 0.92 (s, 1H), 0.92-0.90 (m, 3H), 0.88 (d, J=6.8 Hz, 2H), 0.66 (q, J=12.0 Hz, 1H)

The absolute configurations of the C16 substituents in Example 1 and Example 2 were determined by X-ray crystallographic co-crystallization with FKBP12. [See Stuart L. Schrieber and Jon Clardy, et al., Atomic Structure of the Rapamycin Humano Immunophilin FKBP-12 Complex, *J. Am. Chem. Soc.*, 1991, 113, 7433-7434.] Crystal structures are depicted in FIGS. 1A and 1B and FIGS. 2A and 2B.

Pure FKBP12(1-108) protein was concentrated to 9 mg/mL in 50 mM Tris pH 8.0, 150 mM NaCl, 1 mM EDTA, 1 mM TCEP. The complex for co-crystallization was prepared by mixing the protein with 3 mM of compound (from a 50 mM stock prepared in 90% dDMSO, 10% D2O). The complex was incubated for two hours at 4° C. then was centrifuged at 10000 rpm for 2 minutes to remove any potential pellet before crystallization. Co-crystals were obtained at 20° C. and by sitting drop vapor diffusion using microseed matrix screening [Allan D'Arcy et al., An automated microseed matrix-screening method for protein crystallization, *Acta Cryst.*, (2007) D63, 550-554.] The drops were made up of 200 nL of protein solution, 160 nL of well solution and 40 nL seed-stock. Crystals appeared within a few days in the A1 condition of the commercially available "Ammonium sulfate" screen from Qiagen. The reservoir solution consisted of 2.2M Ammonium sulfate. Crystals were cryo-protected in reservoir solution supplemented with 20% Ethylene Glycol and flash-frozen into liquid nitrogen. Data was collected at the Swiss Light Source Facility (SLS, Villigen, Switzerland) on beamline X10SA.

The data were processed with XDS (Kabsch, W. (2010), XDS. Acta Cryst. D, 66: 125-132). The structures were determined by molecular replacement (Collaborative Computational Project, Number 4 (1994). Acta Cryst. D50, 760-763) using previous FKBP12 X-ray structures as search model. Programs REFMAC (Murshudov G N, Skubak P, Lebedev A A, et al., REFMAC5 for the refinement of macromolecular crystal structures. *Acta Crystallographica Section D: Biological Crystallography.* 2011; 67(Pt 4):355-367) and COOT (Emsley P, Lohkamp B, Scott W G, Cowtan K. Features and development of Coot, *Acta Crystallographica Section D: Biological Crystallography.* 2010; 66(Pt 4):486-501) were used for refinement and model (re)building.

In the following examples, the absolute stereochemistry of the C16 substituent was not determined by X-ray co-crystallization and is not known. In some examples, only the major diastereomer product from the reaction was isolated and characterized. In other examples, each diastereomer was isolated and characterized without absolute stereochemical assignment.

Example 3:
C16-(4-oxoazetidin-2-yl)-C32-deoxo-rapamycin

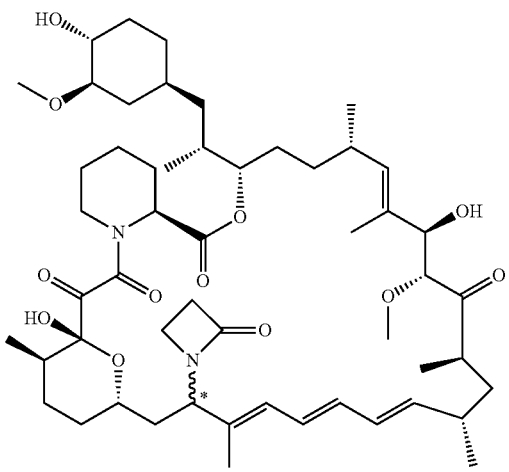 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)C(N3CCC3=O)C[C@@H]3CC[C@@H](C)[C@@](O)(O3)C(=O)C(=O)N3CCCC[C@H]3C(=O)O2)CC[C@H]1O]

Example 3

*Absolute stereochemistry at C16 not assigned

To a solution of Intermediate 1 (130 mg, 0.144 mmol, 1.0 eq) and azetidin-2-one (205 mg, 2.89 mmol, 20 eq) in acetonitrile (3 mL) was added para-toluenesulfonic acid monohydrate (82 mg, 0.433 mmol, 3 eq). The reaction mixture was stirred at room temperature for 15 min and then was diluted with $H_2O$ and was extracted with ethyl acetate. The organic extract was evaporated under reduced pressure. The crude product was purified by preparative-HPLC chromatography (method 1) followed by a SFC purification (method 1) to give of Example 3 (2.5 mg, 1.7% yield) as a white solid.

Example 3: ESIMS [M−H] 938.0

Exact Mass: 938.59

$^1$H NMR (400 MHz, DMSO-$d_6$) δ 6.45 (dd, J=14.0, 11.0 Hz, 1H), 6.28-6.11 (m, 2H), 5.98 (d, J=10.9 Hz, 1H), 5.95-5.85 (m, 1H), 5.50 (dd, J=14.2, 9.5 Hz, 1H), 5.06 (d, J=4.7 Hz, 1H), 5.02-4.97 (m, 1H), 4.94 (d, J=9.8 Hz, 1H), 4.63-4.53 (m, 2H), 4.34-4.22 (m, 1H), 3.99-3.92 (m, 1H), 3.84-3.74 (m, 1H), 3.61-3.53 (m, 1H), 3.49 (d, J=7.3 Hz, 1H), 3.46-3.39 (m, 1H), 3.37-3.25 (m, 3H), 3.22-3.12 (m, 4H), 3.10-3.04 (m, 1H), 3.04-2.95 (m, 1H), 2.92-2.65 (m, 4H), 2.27-2.11 (m, 2H), 2.10-1.99 (m, 2H), 1.96-1.87 (m, 1H), 1.84-1.70 (m, 5H), 1.69-1.37 (m, 15H), 1.37-1.05 (m, 8H), 1.03-0.93 (m, 4H), 0.90 (d, J=6.4 Hz, 3H), 0.88-0.83 (m, 5H), 0.79 (d, J=6.7 Hz, 3H), 0.75 (d, J=6.7 Hz, 3H), 0.59 (q, J=11.8 Hz, 1H).

Example 4: C16-(3-methylimidazolidin-2-one-1-yl)-C32-deoxo-rapamycin

Example 5: C16-(2-hydroxyethyl)-2-oxoimidazolidin-1-yl)-C32-deoxo-rapamycin

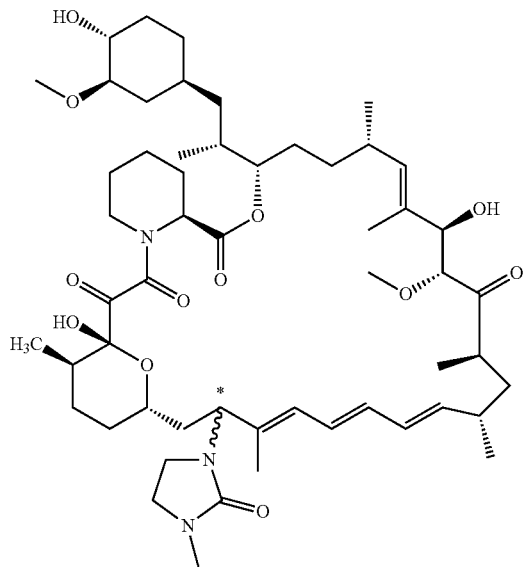 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)C(N3CCN(C)C3=O)C[C@@H]3CC[C@@H](C)[C@@](O)(O3)C(=O)C(=O)N3CCCC[C@H]3C(=O)O2)CC[C@H]1O]

Example 4

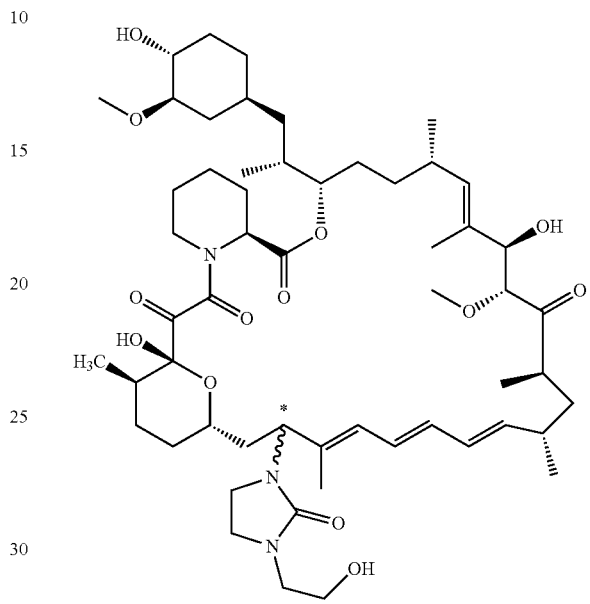

Example 5

*Absolute stereochemistry at C16 not assigned

To a solution of Intermediate 1 (100 mg, 0.111 mmol, 1.0 eq) and 1-methylimidazolidin-2-one (167 mg, 1.66 mmol, 15 eq) in DCM (2 mL) was added para-toluenesulfonic acid monohydrate (63 mg, 0.333 mmol, 3 eq). The reaction mixture was stirred at room temperature for 24 h. The mixture was diluted with $H_2O$ and was extracted with DCM. The organic extract was evaporated under reduced pressure. The crude product was purified by preparative-HPLC chromatography (method 1) to afford Example 4 (9.0 mg, 8% yield) as a white solid.

Example 4: ESIMS [M−H] 966.5

Exact Mass: 967.61

$^1$H NMR (600 MHz, DMSO-$d_6$) δ 0.59 (q, J=11.9 Hz, 1H), 0.74 (d, J=6.7 Hz, 3H), 0.79 (d, J=6.7 Hz, 3H), 0.80-0.90 (m, 8H), 0.92-1.00 (m, 4H), 1.04-1.10 (m, 1H), 1.12-1.34 (m, 7H), 1.34-1.67 (m, 14H), 1.69 (s, 3H), 1.71-1.78 (m, 2H), 1.88-1.94 (m, 1H), 1.96-2.08 (m, 3H), 2.10-2.25 (m, 2H), 2.60-2.69 (m, 4H), 2.80-2.94 (m, 2H), 3.07-3.20 (m, 5H), 3.21-3.26 (m, 2H), 3.33 (s, 3H), 3.41-3.48 (m, 1H), 3.56-3.66 (m, 3H), 3.99 (dd, J=6.5, 3.5 Hz, 1H), 4.53-4.63 (m, 3H), 4.95-5.00 (m, 2H), 5.07 (d, J=4.8 Hz, 1H), 5.35 (s, 1H), 5.45 (dd, J=14.9, 9.8 Hz, 1H), 5.98 (d, J=11.0 Hz, 1H), 6.15 (dd, J=14.8, 10.7 Hz, 1H), 6.23 (dd, J=14.6, 10.7 Hz, 1H), 6.44 (dd, J=14.6, 11.0 Hz, 1H).

*Absolute stereochemistry at C16 not assigned

To a solution of Intermediate 1 (100 mg, 0.111 mmol, 1.0 eq) and 1-(2-hydroxyethyl)limidazolidin-2-one (289 mg, 1.66 mmol, 15 eq) in DCM (2 mL) was added 4-methylbenzenesulfonic acid monohydrate (119 mg, 0.626 mmol, 3 eq). The reaction was stirred at room temperature overnight. The reaction was diluted with $H_2O$ and was extracted with DCM. The organic extract was evaporated under reduced pressure. The crude product was purified by preparative HPLC chromatography (method 1) followed chiral preparative HPLC (method 2) to yield Example 5 (13.7 mg, 12% yield) as a white solid.

Example 5: ESIMS [M+H] 998.5

Exact Mass: 997.62

$^1$H NMR (400 MHz, DMSO-$d_6$) δ 6.45 (dd, J=14.3, 11.0 Hz, 1H), 6.23 (dd, J=14.3, 10.6 Hz, 1H), 6.14 (dd, J=14.6, 10.6 Hz, 1H), 5.98 (d, J=10.9 Hz, 1H), 5.44 (dd, J=14.5, 9.8 Hz, 1H), 5.28 (s, 1H), 5.07 (d, J=4.7 Hz, 1H), 5.02-4.96 (m, 2H), 4.67 (t, J=5.3 Hz, 1H), 4.64-4.53 (m, 3H), 4.03-3.96 (m, 1H), 3.71-3.57 (m, 3H), 3.52-3.42 (m, 2H), 3.42-3.29 (m, 1H), 3.22-3.07 (m, 7H), 2.95-2.79 (m, 2H), 2.71-2.56 (m, 1H), 2.27-1.87 (m, 6H), 1.80-1.36 (m, 20H), 1.36-1.12 (m, 6H), 1.11-1.02 (m, 1H), 1.00-0.91 (m, 4H), 0.91-0.76 (m, 11H), 0.74 (d, J=6.7 Hz, 3H), 0.59 (q, J=11.9 Hz, 1H).

Example 6: C16-(1,1-dioxido-1,2-thiazetidin-2-yl)-C32-deoxo-rapamycin (Diastereomer 1)

Example 7: C16-(1,1-dioxido-1,2-thiazetidin-2-yl)-C32-deoxo-rapamycin (Diastereomer 2)

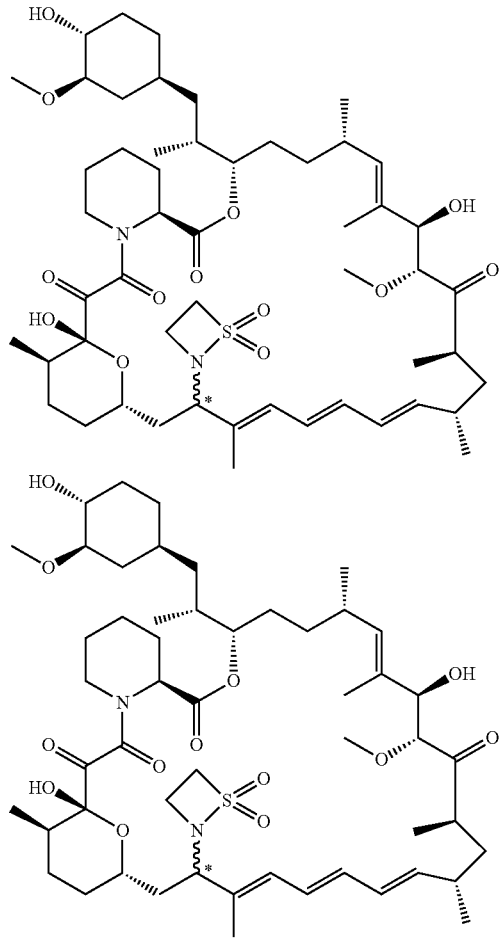

Example 6 and Example 7

*Absolute stereochemistry at C16 not assigned

Diastereomer 1: To a solution of Intermediate 1 (150 mg, 0.167 mmol, 1.0 eq) and 1,2-thiazetidine 1,1-dioxide (89 mg, 0.833 mmol, 5 eq) in DCM (3 mL) was added zinc(II) chloride (1M solution in diethyl ether, 0.5 mL, 0.500 mmol, 3 eq) at 0° C. The reaction mixture was stirred at room temperature for 2 h. The mixture was diluted with $H_2O$ and was extracted with ethyl acetate. The organic extract was evaporated under reduced pressure. The crude product of the diastereomeric mixture was separated by flash chromatography (silica; MeCN/DCM 0:100 to 100:0).

Final purification of the first eluting diastereomer by preparative HPLC (method 2) yielded Example 6 (18 mg, 10.7% yield) as a white solid.

Example 6: ESIMS [M+NH$_4$] 992.6, [M+FA−H] 1019.6
Exact Mass: 974.55

$^1$H NMR (400 MHz, Chloroform-d) δ 6.39 (dd, J=14.8, 9.8 Hz, 1H), 6.34 (dd, J=14.8, 10.3 Hz, 1H), 6.18-6.10 (m, 1H), 6.02 (d, J=10.3, 1.5 Hz, 1H), 5.66 (dd, J=15.1, 8.6 Hz, 1H), 5.38 (s, 1H), 5.32 (dd, J=6.4, 1.8 Hz, 1H), 5.23 (d, J=9.6 Hz, 1H), 4.87-4.76 (m, 1H), 4.12-4.06 (m, 1H), 3.99 (ddd, J=12.0, 8.2, 6.2 Hz, 1H), 3.92-3.86 (m, 1H), 3.84 (dd, J=10.7, 4.4 Hz, 1H), 3.81-3.74 (m, 1H), 3.63-3.59 (m, 2H), 3.59 (d, J=3.6 Hz, 1H), 3.46 (d, J=7.6 Hz, 1H), 3.43 (s, 3H), 3.40-3.37 (m, 1H), 3.32 (s, 3H), 3.04 (ddd, J=8.2, 5.8, 3.8 Hz, 1H), 3.00-2.94 (m, 1H), 2.94-2.89 (m, 1H), 2.88-2.84 (m, 1H), 2.64 (d, J=6.7 Hz, 1H), 2.47-2.38 (m, 1H), 2.36-2.27 (m, 2H), 2.21-2.12 (m, 1H), 2.03-1.97 (m, 1H), 1.95-1.77 (m, 7H), 1.76-1.67 (m, 5H), 1.65 (s, 3H), 1.60-1.50 (m, 6H), 1.47-1.39 (m, 2H), 1.38-1.27 (m, 4H), 1.25-1.10 (m, 3H), 1.08-1.04 (m, 1H), 1.03-1.01 (m, 3H), 1.00 (d, J=1.4 Hz, 3H), 0.99-0.97 (m, 3H), 0.97 (d, J=6.6 Hz, 3H), 0.93 (d, J=6.8 Hz, 3H), 0.75-0.66 (m, 1H).

Final purification of the second eluting diastereomer using SFC chromatography (method 2) yielded Example 7 (15.8 mg, 9.2% yield) as a white solid.

Example 7: ESIMS [M+NH$_4$] 992.7, [M+FA−H] 1019.6
Exact Mass: 974.55

$^1$H NMR (400 MHz, Chloroform-d) δ 6.46 (dd, J=14.2, 10.9 Hz, 1H), 6.22 (dd, J=14.2, 10.6 Hz, 1H), 6.14 (dd, J=14.5, 10.6 Hz, 1H), 6.00 (d, J=10.9 Hz, 1H), 5.38 (dd, J=14.5, 9.6 Hz, 1H), 5.27-5.19 (m, 1H), 5.12-5.05 (m, 1H), 4.66-4.59 (m, 1H), 4.59-4.53 (m, 1H), 4.25 (d, J=1.8 Hz, 1H), 4.17-4.06 (m, 3H), 4.02 (ddd, J=11.8, 8.0, 3.5 Hz, 1H), 3.66 (d, J=7.0 Hz, 1H), 3.60-3.52 (m, 2H), 3.43-3.34 (m, 4H), 3.28 (s, 3H), 3.17-3.07 (m, 1H), 3.03-2.95 (m, 1H), 2.95-2.89 (m, 1H), 2.84-2.73 (m, 1H), 2.65-2.62 (m, 1H), 2.35-2.26 (m, 1H), 2.27-2.21 (m, 1H), 2.21-2.12 (m, 3H), 2.12-2.05 (m, 1H), 2.02-1.98 (m, 1H), 1.97-1.95 (m, 3H), 1.91-1.83 (m, 1H), 1.82-1.70 (m, 3H), 1.70-1.51 (m, 10H), 1.50-1.17 (m, 10H), 1.11-1.06 (m, 1H), 1.06-1.02 (m, 6H), 1.01-0.96 (m, 1H), 0.93 (d, J=6.8 Hz, 4H), 0.89 (d, J=6.6 Hz, 3H), 0.86 (d, J=6.8 Hz, 3H), 0.64 (q, J=11.9 Hz, 1H).

Example 8: C16-(1,1-dioxido-1,2-thiazetidin-2-yl)-C32-deoxo-C40-(2-hydroxyethoxy)-rapamycin (diastereomer 1)

Example 9: C16-(1,1-dioxido-1,2-thiazetidin-2-yl)-C32-deoxo-C40-(2-hydroxyethoxy)-rapamycin (diastereomer 2)

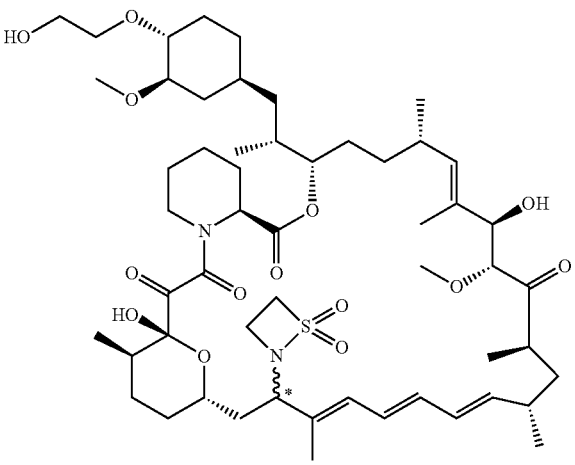

-continued

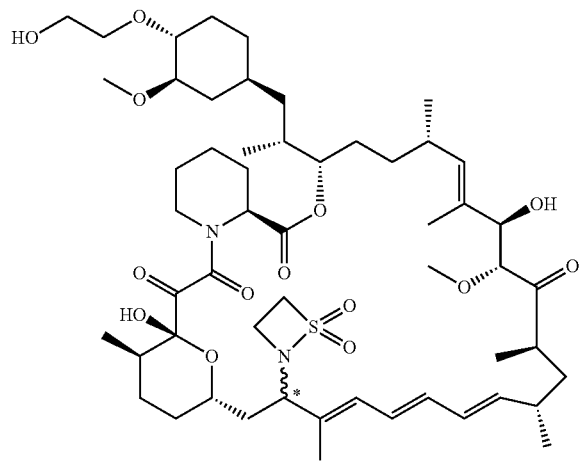

Example 8 and Example 9

*Absolute stereochemistry at C16 not assigned

To a solution of Intermediate 3 (50 mg, 0.053 mmol, 1.0 eq) and 1,2-thiazetidine 1,1-dioxide (56.7 mg, 0.530 mmol, 10 eq) in DCM (1 mL) was added zinc(II) chloride (1M solution in diethyl ether, 0.265 mL, 0.265 mmol, 5 eq). The reaction mixture was stirred at room temperature for 1.5 hours. The reaction was diluted with H$_2$O and was extracted with ethyl acetate. The organic extract was evaporated under reduced pressure. The crude product of the diastereomeric mixture was separated by flash chromatography (silica; MeCN/DCM 0:100 to 100:0).

Final purification of the first eluting diastereomer using preparative HPLC (method 2) yielded Example 8 (3.1 mg, 5.5% yield) as a white solid.

Example 8: ESIMS [M+NH$_4$] 1037.0, [M+FA−H] 1064.1
Exact Mass: 1018.58
$^1$H NMR (400 MHz, DMSO-d$_6$) δ: 6.53-6.44 (m, 1H), 6.41 (dd, J=11.0, 5.6 Hz, 1H), 6.29-6.14 (m, 2H), 6.07 (dd, J=11.0, 1.5 Hz, 1H), 5.54 (dd, J=14.6, 9.1 Hz, 1H), 5.06 (d, J=8.9 Hz, 1H), 4.99-4.93 (m, 1H), 4.92-4.83 (m, 1H), 4.70-4.60 (m, 1H), 4.49-4.42 (m, 1H), 4.13-4.02 (m, 3H), 3.92-3.86 (m, 1H), 3.69-3.64 (m, 1H), 3.59-3.54 (m, 1H), 3.52-3.42 (m, 5H), 3.33 (s, 3H), 3.30-3.27 (m, 1H), 3.13 (s, 3H), 3.10-3.02 (m, 2H), 3.02-2.94 (m, 2H), 2.90-2.80 (m, 1H), 2.30-2.21 (m, 1H), 2.21-2.10 (m, 1H), 2.10-2.00 (m, 2H), 2.00-1.87 (m, 3H), 1.82 (s, 3H), 1.81-1.62 (m, 6H), 1.58-1.54 (m, 1H), 1.53-1.47 (m, 5H), 1.47-1.35 (m, 5H), 1.36-1.23 (m, 2H), 1.23-1.09 (m, 4H), 1.06-1.01 (m, 1H), 1.01-0.95 (m, 6H), 0.90-0.87 (m, 1H), 0.87-0.83 (m, 3H), 0.81 (d, J=6.7 Hz, 3H), 0.76-0.70 (m, 4H), 0.68-0.60 (m, 1H).

Final purification of the second eluting diastereomer using preparative HPLC (method 2) yielded Example 9 (2.8 mg, 4.9% yield) as a white solid.

Example 9: ESIMS [M+NH4] 1037.2, [M+FA−H] 1064.3
Exact Mass: 1018.58
$^1$H NMR (400 MHz, DMSO-d$_6$) δ: 6.48-6.40 (m, 1H), 6.27-6.19 (m, 1H), 6.19-6.13 (m, 1H), 6.10-6.05 (m, 1H), 5.52 (dd, J=14.2, 9.3 Hz, 1H), 5.13-5.00 (m, 2H), 4.96 (d, J=9.4 Hz, 1H), 4.67-4.57 (m, 1H), 4.48-4.40 (m, 1H), 4.17-4.10 (m, 2H), 4.10-4.02 (m, 2H), 3.98-3.90 (m, 1H), 3.56-3.49 (m, 2H), 3.50-3.43 (m, 4H), 3.37 (d, J=11.2 Hz, 1H), 3.33 (s, 3H), 3.23-3.15 (m, 1H), 3.15-3.10 (m, 4H), 3.07-2.95 (m, 2H), 2.75-2.64 (m, 1H), 2.27-2.14 (m, 2H), 2.11-2.00 (m, 2H), 2.00-1.89 (m, 3H), 1.82 (s, 3H), 1.76-1.65 (m, 2H), 1.65-1.56 (m, 3H), 1.56-1.49 (m, 7H), 1.48-1.36 (m, 3H), 1.34-1.23 (m, 3H), 1.23-1.04 (m, 5H), 1.01-0.94 (m, 4H), 0.90 (d, J=6.4 Hz, 3H), 0.88-0.83 (m, 5H), 0.80 (d, J=6.7 Hz, 3H), 0.75 (d, J=6.7 Hz, 3H), 0.62 (q, J=11.8 Hz, 1H).

Example 10: C16-(1,1-dioxido-1,2-thiazetidin-2-yl)-C32-deoxo-C40-dimethylphosphinyl-rapamycin (Diastereomer 1)

Example 11: C16-(1,1-dioxido-1,2-thiazetidin-2-yl)-C32-deoxo-C40-dimethylphosphinyl-rapamycin (Diastereomer 2)

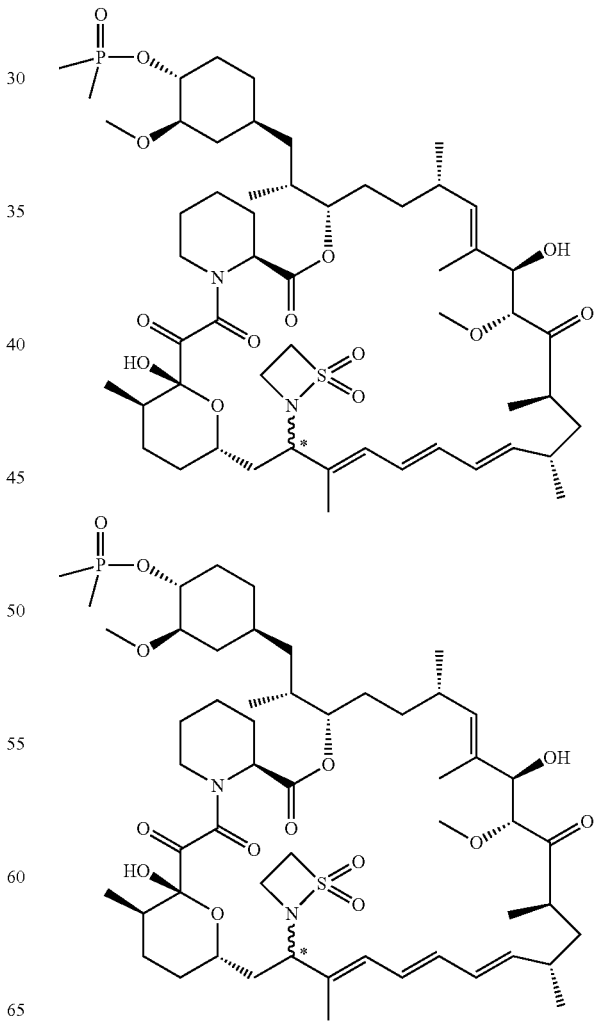

Example 10 and Example 11

*Absolute stereochemistry at C16 not assigned

To a solution of Intermediate 4 (100 mg, 0.102 mmol, 1.0 eq) and 1,2-thiazetidine 1,1-dioxide (54.9 mg, 0.512 mmol, 5 eq) in DCM (5 mL) was added zinc(II) chloride (1M solution in diethyl ether, 0.512 mL, 0.512 mmol, 5 eq). The reaction mixture was stirred at room temperature for 15 minutes. The reaction was diluted with $H_2O$ and was extracted with ethyl acetate. The organic extract was evaporated under reduced pressure. The crude product the diastereomeric mixture was separated by SFC chromatography (method 3).

Final purification of the first eluting diastereomer using preparative HPLC (method 2) yielded Example 10 (20.7 mg, 18.8% yield) as a white solid.

Example 10: ESIMS [M+H] 1051.9, [M+FA−H] 1096.0

Exact Mass: 1050.56

$^1$H NMR (400 MHz, DMSO-$d_6$) δ 6.49-6.39 (m, 2H), 6.30-6.14 (m, 2H), 6.11-6.01 (m, 1H), 5.60-5.50 (m, 1H), 5.06-5.00 (m, 1H), 4.98-4.93 (m, 1H), 4.87 (d, J=9.7 Hz, 1H), 4.67-4.58 (m, 1H), 4.17-4.01 (m, 3H), 4.01-3.92 (m, 1H), 3.92-3.85 (m, 1H), 3.73-3.64 (m, 1H), 3.60-3.52 (m, 1H), 3.50-3.42 (m, 1H), 3.35-3.26 (m, 4H), 3.15-3.12 (m, 3H), 3.11-3.01 (m, 2H), 3.01-2.95 (m, 1H), 2.88-2.79 (m, 1H), 2.29-2.20 (m, 1H), 2.20-2.12 (m, 1H), 2.10-1.99 (m, 2H), 1.99-1.87 (m, 3H), 1.82 (s, 3H), 1.80-1.71 (m, 1H), 1.71-1.62 (m, 4H), 1.58-1.54 (m, 1H), 1.52-1.48 (m, 5H), 1.47-1.31 (m, 13H), 1.28-1.11 (m, 4H), 1.07-1.02 (m, 1H), 1.01-0.95 (m, 8H), 0.87-0.84 (m, 3H), 0.82 (d, J=6.7 Hz, 3H), 0.79-0.76 (m, 1H), 0.74 (d, J=6.7 Hz, 3H), 0.72-0.66 (m, 1H).

Final purification of the second eluting diastereomer using preparative HPLC (method 2) yielded Example 11 (13.4 mg, 12.2% yield) as a white solid.

Example 11: ESIMS [M+H] 1051.8, [M+FA−H] 1095.8

Exact Mass: 1050.56

$^1$H NMR (400 MHz, DMSO-$d_6$) δ 6.51-6.39 (m, 1H), 6.28-6.13 (m, 2H), 6.08 (d, J=11.1 Hz, 1H), 6.04-5.88 (m, 1H), 5.57-5.46 (m, 1H), 5.05 (s, 1H), 5.03 (d, J=5.7 Hz, 1H), 4.96 (d, J=9.9 Hz, 1H), 4.67-4.56 (m, 1H), 4.18-4.11 (m, 2H), 4.09-4.02 (m, 2H), 3.99-3.89 (m, 2H), 3.60-3.49 (m, 2H), 3.37 (d, J=13.3 Hz, 1H), 3.30 (s, 3H), 3.18 (dt, J=7.7, 5.1 Hz, 1H), 3.15-3.11 (m, 4H), 3.07-3.00 (m, 1H), 2.73-2.63 (m, 1H), 2.28-2.13 (m, 2H), 2.13-2.05 (m, 2H), 2.05-1.97 (m, 2H), 1.97-1.88 (m, 1H), 1.83 (s, 3H), 1.80-1.69 (m, 1H), 1.68-1.58 (m, 4H), 1.58-1.48 (m, 7H), 1.48-1.43 (m, 1H), 1.42-1.34 (m, 10H), 1.34-1.28 (m, 1H), 1.28-1.22 (m, 2H), 1.22-1.13 (m, 2H), 1.13-1.03 (m, 1H), 1.03-0.94 (m, 5H), 0.94-0.88 (m, 4H), 0.86 (d, J=6.5 Hz, 3H), 0.81 (d, J=6.7 Hz, 3H), 0.75 (d, J=6.6 Hz, 3H), 0.66 (q, J=12.0 Hz, 1H).

Example 12: C16-(1,1-dioxido-1,2-thiazetidin-2-yl)-C32-deoxo-C40-(S)-(1H-tetrazol-1-yl)-rapamycin (Diastereomer 1)

Example 13: C16-(1,1-dioxido-1,2-thiazetidin-2-yl)-C32-deoxo-C40-(S)-(1H-tetrazol-1-yl)-rapamycin (Diastereomer 2)

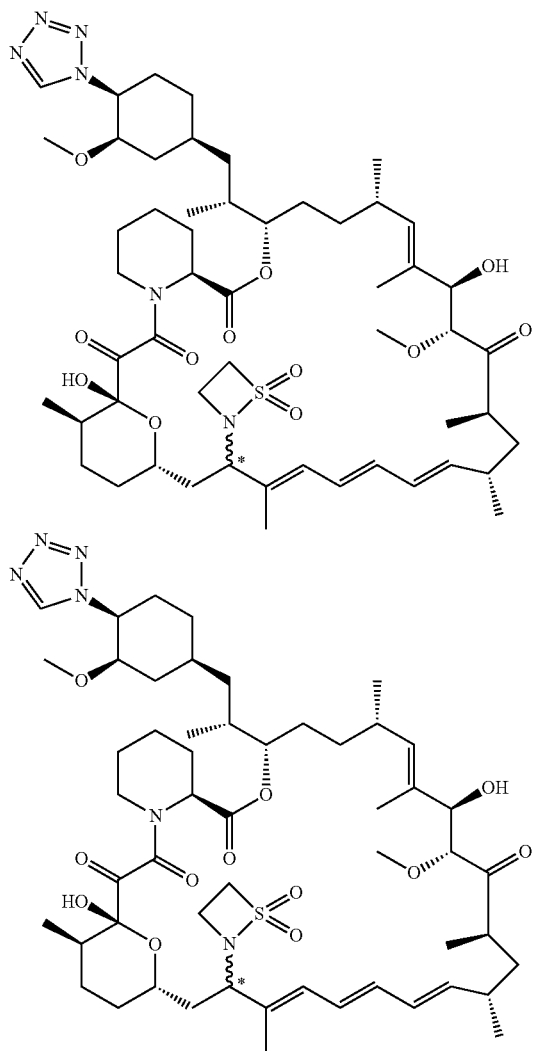

Example 12 and Example 13

*Absolute stereochemistry at C16 not assigned

To a solution of Intermediate 5 (118 mg, 0.124 mmol, 1.0 eq) and 1,2-thiazetidine 1,1-dioxide (66.4 mg, 0.620 mmol, 5 eq) in DCM (6 mL) was added zinc(II) chloride (1M solution in diethyl ether, 0.620 mL, 0.620 mmol, 5 eq). The reaction mixture was stirred at room temperature for three hours. The reaction was diluted with $H_2O$ and was extracted with ethyl acetate. The organic extract was evaporated under reduced pressure. The crude product of the diastereomeric mixture was separated by SFC chromatography (method 3).

Final purification of the first eluting diastereomer using preparative HPLC (method 2) yielded Example 12 (14.8 mg, 11.3% yield) as a white solid.

Example 12: ESIMS [M+NH4] 1050.0, [M+FA−H] 1072.1

Exact Mass: 1026.57

$^1$H NMR (400 MHz, DMSO-d$_6$) δ 9.32 (s, 1H), 6.52 (s, 1H), 6.45-6.37 (m, 1H), 6.31-6.14 (m, 2H), 6.10-6.04 (m, 1H), 5.60-5.49 (m, 1H), 5.23-5.12 (m, 1H), 5.07-5.01 (m, 1H), 4.99-4.93 (m, 1H), 4.87 (d, J=9.7 Hz, 1H), 4.69-4.59 (m, 1H), 4.15-4.02 (m, 3H), 3.94-3.84 (m, 1H), 3.72-3.54 (m, 3H), 3.51-3.42 (m, 1H), 3.27 (s, 4H), 3.11 (s, 3H), 3.07 (dd, J=7.3, 5.1 Hz, 1H), 3.01-2.91 (m, 1H), 2.85 (td, J=10.6, 9.5, 4.7 Hz, 1H), 2.28-2.13 (m, 3H), 2.10-2.00 (m, 2H), 1.98-1.88 (m, 3H), 1.82 (s, 3H), 1.80-1.75 (m, 1H), 1.73-1.67 (m, 4H), 1.59-1.53 (m, 4H), 1.53-1.45 (m, 6H), 1.45-1.34 (m, 3H), 1.33-1.20 (m, 3H), 1.20-1.07 (m, 3H), 1.05-1.01 (m, 1H), 1.00-0.94 (m, 6H), 0.88-0.82 (m, 6H), 0.80-0.75 (m, 1H), 0.73 (d, J=6.7 Hz, 3H).

Final purification of the second eluting diastereomer using preparative HPLC (method 2) yielded Example 13 (12.3 mg, 9.4% yield) as a white solid.

Example 13: ESIMS [M+H] 1027.7, [M−H] 1025.6, [M+FA−H] 1071.6

Exact Mass: 1026.57

$^1$H NMR (400 MHz, DMSO-d$_6$ δ 9.30 (s, 1H), 6.52-6.38 (m, 1H), 6.28-6.14 (m, 2H), 6.08 (d, J=11.1 Hz, 1H), 5.58-5.42 (m, 1H), 5.21-5.14 (m, 1H), 5.10-5.00 (m, 2H), 5.00-4.92 (m, 1H), 4.69-4.57 (m, 1H), 4.16-4.10 (m, 3H), 4.08-4.01 (m, 1H), 3.97-3.91 (m, 1H), 3.61 (dt, J=10.6, 4.1 Hz, 1H), 3.57-3.51 (m, 1H), 3.51-3.46 (m, 1H), 3.46-3.36 (m, 1H), 3.27 (s, 3H), 3.19-3.15 (m, 1H), 3.12 (s, 3H), 3.11-3.08 (m, 1H), 2.80-2.68 (m, 1H), 2.25-2.15 (m, 3H), 2.10-2.01 (m, 2H), 2.01-1.89 (m, 2H), 1.83 (s, 3H), 1.79-1.65 (m, 4H), 1.64-1.58 (m, 2H), 1.57-1.54 (m, 2H), 1.54-1.47 (m, 7H), 1.46-1.35 (m, 3H), 1.32-1.18 (m, 5H), 1.14-1.04 (m, 3H), 0.98 (d, J=6.6 Hz, 3H), 0.91-0.85 (m, 7H), 0.83 (d, J=6.7 Hz, 3H), 0.72 (d, J=6.6 Hz, 3H).

Example 14: C16-(1,1-dioxidoisothiazolidin-2-yl)-C32-deoxo-C40-dimethylphosphinyl-rapamycin (Diastereomer 1)

Example 15: C16-(1,1-dioxidoisothiazolidin-2-yl)-C32-deoxo-C40-dimethylphosphinyl-rapamycin (Diastereomer 2)

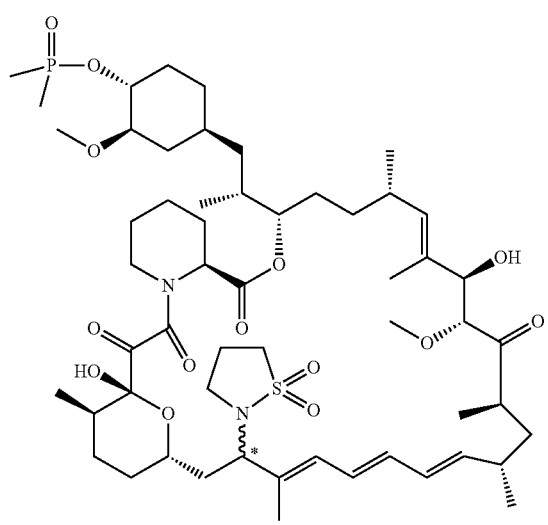

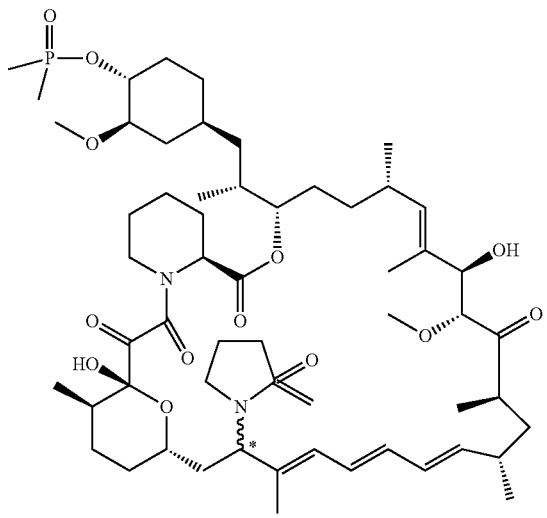

Example 14 and Example 15

*Absolute stereochemistry at C16 not assigned

Intermediate 4 (0.146 g, 0.150 mmol) and isothiazolidine 1,1-dioxide (0.181 g, 1.496 mmol) were dissolved into anhydrous acetonitrile (1.5 mL). para-Toluenesulfonic acid monohydrate (2.84 mg, 0.015 mmol) was added in one portion. The reaction mixture was stirred at room temperature for two hours.

Aqueous saturated NaHCO$_3$ was added. The mixture was extracted several times with ethyl acetate. The organic extracts were combined, dried over Na$_2$SO, decanted and concentrated to give a colorless tar crude product.

The crude product was dissolved in MeOH (2.5 mL) and was purified in one injection via preparative-scale reverse phase chromatography (40-90% acetonitrile-water plus 0.1% TFA modifier on 100 g C18 ISCO column).

The first eluting peak fractions were pooled and reduced to about ⅓ volume on a rotary evaporator. The remaining solution was made basic with saturated aqueous NaHCO$_4$ and was extracted several times with EtOAc. The organic extracts were combined, dried over Na$_2$SO$_4$, decanted and concentrated to give Example 14 (0.055 g, 0.044 mmol, 29.3 yield) as a white solid.

Example 14: ESIMS [M+NH4] 1082.8, [M−H] 1063.7

HRMS: calculated for C55H89N2O14PSNa as sodium adduct—1087.5670. Found—1087.5725.

$^1$H NMR (400 MHz, Chloroform-d) δ 6.45 (dd, J=14.4, 10.9 Hz, 1H), 6.22 (dd, J=14.5, 10.6 Hz, 1H), 6.13 (dd, J=14.6, 10.5 Hz, 1H), 5.98 (d, J=10.8 Hz, 1H), 5.35 (dd, J=14.7, 9.8 Hz, 1H), 5.23-5.17 (m, 1H), 5.10 (d, J=9.8 Hz, 1H), 4.67 (m, 2H), 4.47 (d, J=1.8 Hz, 1H), 4.18-4.04 (m, 2H), 4.03-3.91 (m, 1H), 3.72 (d, J=6.5 Hz, 1H), 3.68-3.48 (m, 2H), 3.38 (m, 4H), 3.28 (s, 3H), 3.26-3.12 (m, 2H), 3.12-2.91 (m, 4H), 2.74 (m, 1H), 2.48-2.26 (m, 3H), 2.26-2.12 (m, 3H), 2.12-2.04 (m, 2H), 1.87 (s, 3H), 1.85-1.72 (m, 4H), 1.72-1.54 (m, 12H), 1.54-1.43 (m, 6H), 1.43-1.33 (m, 3H), 1.33-1.21 (m, 2H), 1.21-1.09 (m, 2H), 1.03 (m, 7H), 1.00-0.78 (m, 9H), 0.72 (q, J=11.9 Hz, 1H).

The second eluting peak fractions were pooled and reduced to about ⅓ volume on the rotary evaporator. The remaining solution was made basic with saturated aqueous NaHCO3. The mixture was extracted several times with ethyl acetate. The organic extracts were combined, dried over Na2SO4, decanted and concentrated to give Example 15 (0.010 g, 7.51 μmol, 5.02% yield) as a white solid.

Example 15: ESIMS [M+NH4] 1082.8, [M−H] 1063.8

¹H NMR (400 MHz, Chloroform-d δ 6.36 (dd, J=19.2, 10.3 Hz, 1H), 6.13 (m, 1H), 6.04-5.84 (m, 1H), 5.65 (m, 1H), 5.32 (m, 1H), 6.21 (m, 1H), 5.11 (m, 1H), 4.81 (dd, J=13.7, 7.5 Hz, 1H), 4.21-4.03 (m, 1H), 3.83 (dd, J=15.2, 5.1 Hz, 2H), 3.74 (d, J=13.2 Hz, 1H), 3.59 (dq, J=10.9, 6.8, 5.6 Hz, 2H), 3.52 (d, J=7.1 Hz, 1H), 3.46-3.33 (m, 7H), 3.30 (m, 3H), 3.18 (m, 3H), 3.10-2.82 (m, 3H), 2.39 (t, J=4.1 Hz, 1H), 2.28 (m, 3H), 2.14 (m, 3H), 1.90-1.77 (m, 4H), 1.74 (m, 4H), 1.66 (d, J=10.4 Hz, 3H), 1.61-1.41 (m, 12H), 1.34-1.19 (m, 5H), 1.18-1.11 (m, 1H), 1.11-0.79 (m, 19H), 0.78-0.68 (m, 1H).

Example 16: (R)—C16-(1,1-dioxidoisothiazolidin-2-yl)-C32-deoxo-C40-(2-hydroxyethoxy)-rapamycin

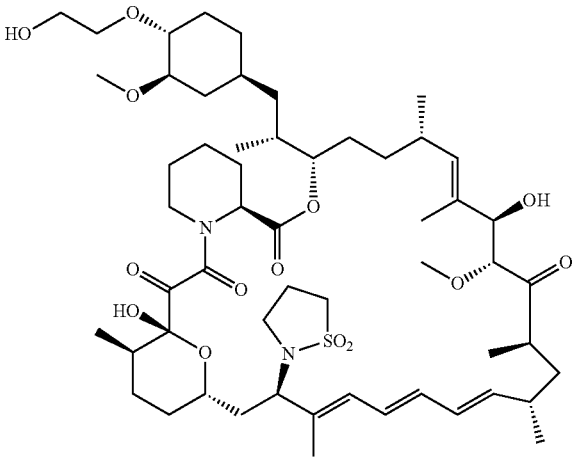 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](N3CCCS3(=O)=O)C[C@@H]3CC[C@@H](C)[C@@](O)(O3)C(=O)C(=O)N3CCCC[C@H]3C(=O)O2)CC[C@H]1OCCO]

Example 16

Absolute stereochemistry at C16 known to be (R) based on using Example 2 as starting material.

Example 16 was prepared in a two-step procedure from 2-((tert-butyldimethylsilyl)oxy)ethanol and Example 2.

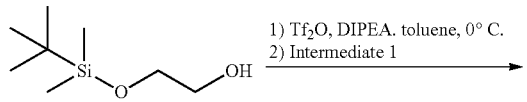

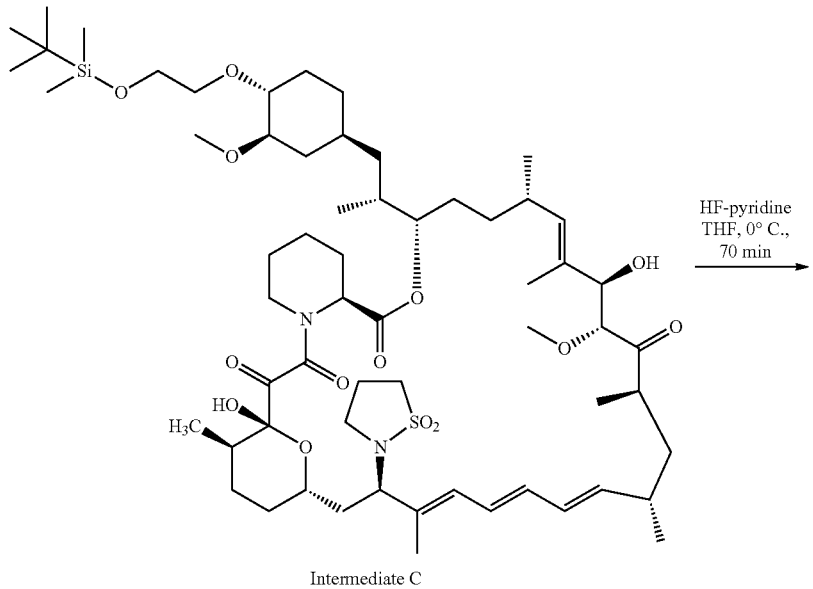

Intermediate C

-continued

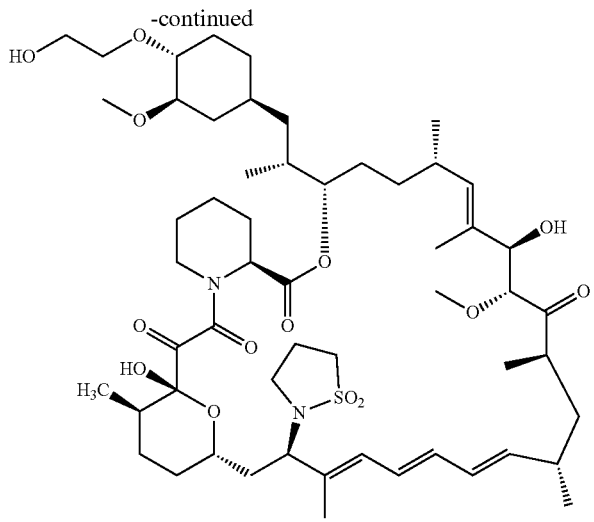

Example 16

Step 1. Preparation of Intermediate C 2-((tert-butyldimethylsilyl)oxy)ethanol (0.142 g, 0.803 mmol) was dissolved in anhydrous toluene (0.4 mL). N,N-diisopropylethylamine (0.147 ml, 0.843 mmol) was added via syringe. The mixture was vacuum purged with nitrogen then was chilled to 0C in an ice-water bath. Triflic anhydride (0.132 ml, 0.779 mmol) was added via syringe over a period of 60 seconds. The reaction was stirred at 0 C for 30 minutes.

N,N-diisopropylethylamine (0.147 ml, 0.843 mmol), toluene (0.5 mL) and Example 2 (0.198 g, 0.200 mmol) were added. The ice bath was removed and the reaction was stirred overnight at 40 C and then for one hour at 55 C.

The reaction was diluted with saturated aqueous NaHCO3 and was extracted four times with EtOAc. The organic extracts were combined, dried over Na2SO4, vacuum filtered through celite, and concentrated to give a crude product colorless oil.

The crude product was purified by silica gel flash column chromatography (0-40% acetone-heptane, gradient elution, 12 g silica column, TLC in 30% Acetone-heptane, visualize under UV) to give Intermediate C (0.077 g, 0.067 mmol, 33.5% yield) as a white solid.

Intermediate C: ESIMS [M+NH4] 1164.7, [M−H] 1147.0.

Step 2. Preparation of Example 16

Intermediate C (0.077 g, 0.067 mmol) was combined with pyridine (5.43 µl, 0.067 mmol) in anhydrous THF (0.7 mL). The mixture was vacuum purged twice with nitrogen and then was chilled to 0 C in an ice-water bath. HF-Pyridine (0.086 ml, 0.671 mmol) was added dropwise via syringe over a period of 15 seconds. The reaction was stirred at 0 C for 70 minutes.

The reaction was quenched with saturated aqueous NaHCO3 and was extracted several times with EtOAc. The organic extracts were combined, dried over Na2SO4, vacuum filtered through celite and concentrated to give a white solid crude product.

The crude product was purified by silica gel flash column chromatography (0-40% acetone-heptane, gradient elution, 12 g silica column, TLC in 40% EtOAc-heptane, visualize under UV) to give Example 16 (0.049 g, 0.046 mmol, 69.0% yield) as a white solid.

Example 16: ESIMS [M+NH4] 1050.9, [M−H] 1031.9

$^1$H NMR (600 MHz, Chloroform-d) δ 6.45 (dd, J=14.6, 10.9 Hz, 1H), 6.22 (dd, J=14.7, 10.6 Hz, 1H), 6.13 (dd, J=14.9, 10.6 Hz, 1H), 5.98 (d, J=10.9 Hz, 1H), 5.35 (dd, J=14.9, 9.8 Hz, 1H), 5.20 (d, J=5.9 Hz, 1H), 5.09 (d, J=9.9 Hz, 1H), 4.71 (d, J=12.3 Hz, 1H), 4.62 (m, 1H), 4.46 (s, 1H), 4.11 (d, J=6.8 Hz, 1H), 3.96 (t, J=11.3 Hz, 1H), 3.78 (m, 1H), 3.70 (m, 3H), 3.63-3.55 (m, 3H), 3.43 (s, 3H), 3.28 (s, 3H), 3.24-3.15 (m, 2H), 3.12-3.04 (m, 2H), 3.07-2.98 (m, 1H), 2.97 (q, J=7.9 Hz, 1H), 2.75 (m, 1H), 2.44-2.33 (m, 1H), 2.30 (M, 2H), 2.23 (m, 1H), 2.16 (m, 2H), 2.09 (d, J=13.1 Hz, 1H), 2.01 (m, 1H), 1.88 (s, 3H), 1.84 (d, J=13.1 Hz, 1H), 1.78-1.70 (m, 3H), 1.70-1.62 (m, 4H), 1.52 (dd, J=11.8, 7.7 Hz, 1H), 1.50-1.41 (m, 2H), 1.43-1.32 (m, 1H), 1.34-1.27 (m, 1H), 1.30-1.17 (m, 8H), 1.04 (dd, J=9.5, 6.6 Hz, 7H), 1.02-0.85 (m, 10H), 0.85 (d, J=6.8 Hz, 3H), 0.69 (q, J=12.0 Hz, 1H).

Example 17: C16-(1,1-dioxidoisothiazolidin-2-yl)-C32-deoxo-C40-(S)-(1H-tetrazol-1-yl)-rapamycin

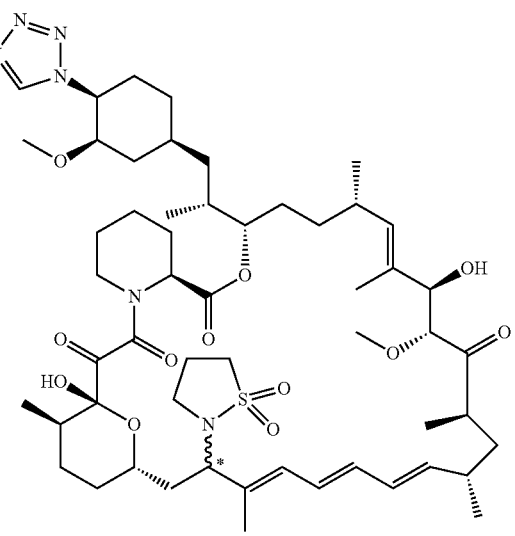

Example 17

*Absolute stereochemistry at C16 not assigned

Intermediate 5 (0.109 g, 0.114 mmol) was combined with isothiazolidine 1,1-dioxide (0.139 g, 1.145 mmol) in anhydrous acetonitrile (1.1 mL). para-Toluenesulfonic acid monohydrate (0.0022 g, 0.011 mmol) was added. The reaction was stirred at room temperature for two hours.

The reaction was diluted with saturated aqueous NaHCO3. The mixture was extracted several times with EtOAc. The organic extracts were combined, dried over $Na_2SO$, decanted and concentrated to give a yellow tar crude product.

The crude product was purified by silica gel flash column chromatography (0-40% acetone-heptane, gradient elution, 24 g silica column, TLC in 40% acetone-heptane, visualize under UV) to give Example 17 (0.053 g, 0.046 mmol, 40.0% yield) as a white solid.

Example 17: ESIMS [M+H] 1041.8, [M−H] 1039.8

HRMS: calculated for C54H84N6O12SNa—1063.5765. Found—1063.5759.

$^1$H NMR (600 MHz, Chloroform-d) δ 8.86 (s, 1H), 6.39 (dd, J=14.7, 11.0 Hz, 1H), 6.22 (dd, J=14.7, 10.7 Hz, 1H), 6.11 (dd, J=15.0, 10.5 Hz, 1H), 5.99 (d, J=10.9 Hz, 1H), 5.34 (dd, J=14.9, 9.8 Hz, 1H), 5.18 (d, J=5.7 Hz, 1H), 5.10 (d, J=9.8 Hz, 1H), 4.87 (m, 1H), 4.67 (m, 1H), 4.63 (d, J=12.2 Hz, 1H), 4.50 (s, 1H), 4.13 (d, J=6.1 Hz, 1H), 3.97 (t, J=11.4 Hz, 1H), 3.78 (d, J=6.2 Hz, 1H), 3.69-3.62 (m, 1H), 3.55 (dt, J=11.2, 4.0 Hz, 1H), 3.50-3.39 (m, 1H), 3.39 (s, 3H), 3.38-3.30 (m, 1H), 3.27 (s, 3H), 3.25-3.13 (m, 1H), 3.07 (td, J=8.4, 3.8 Hz, 1H), 3.01 (m, 1H), 2.96 (q, J=7.9 Hz, 1H), 2.70-2.63 (m, 2H), 2.39 (m, 1H), 2.35-2.21 (m, 3H), 2.18 (d, J=13.7 Hz, 1H), 2.16-2.09 (m, 1H), 1.95-1.81 (m, 3H), 1.82 (s, 3H), 1.75 (m, 3H), 1.65 (s, 3H), 1.60 (m, 6H), 1.58-1.50 (m, 1H), 1.53-1.34 (m, 2H), 1.32 (m, 1H), 1.29 (m, 1H), 1.25 (m, 6H), 1.12 (m, 1H), 1.05 (d, J=6.6 Hz, 3H), 1.05-0.78 (m, 12H).

Example 18: C16-(1,1-dioxidoisothiazolidin-2-yl)-C32-deoxo-C40-(2-ethoxyethoxy)-rapamycin

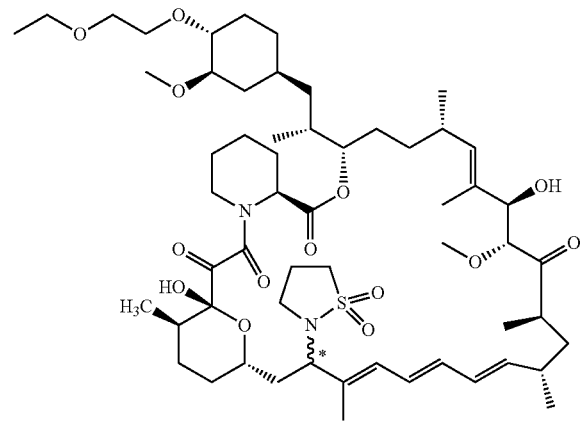 [SMILES: CCOCCO[C@@H]1CC[C@@H](C[C@@H](C)[C@@H]2CC[C@H](C)/C=C(\C)[C@@H](O)[C@@H](OC)C(=O)[C@H](C)C[C@H](C)/C=C/C=C/C=C(\C)C(N3CCCS3(=O)=O)C[C@@H]3CC[C@@H](C)[C@@](O)(O3)C(=O)C(=O)N3CCCC[C@H]3C(=O)O2)C[C@H]1OC]

Example 18

*Absolute stereochemistry at C16 not assigned

Intermediate 6 (0.090 g, 0.093 mmol) was combined with isothiazolidine 1,1-dioxide (0.112 g, 0.926 mmol) in anhydrous dichloromethane (0.93 mL). para-Toluenesulfonic acid monohydrate (1.761 mg, 9.26 µmol) was added in one portion. The reaction was stirred at room temperature for 100 minutes.

The entire reaction mixture was purified by silica gel flash column chromatography (0-40% acetone-heptane, gradient elution, 24 g silica column, TLC in 40% acetone-heptane, visualize under UV) to give a mixture of Example 18 and residual unreacted isothiazolidine 1,1-dioxide.

The mixed material was again purified by silica gel flash column chromatography (0-50% acetonitrile-dichloromethane, gradient elution, 24 g column, TLC in 30% acetonitrile-dichloromethane, visualize under UV) to give Example 18 (0.021 g, 0.019 mmol, 20.4 yield) as a white solid.

Example 18: ESIMS [M+NH4] 1078.9, [M−H] 1059.9

HRMS: calculated for C57H92N2O14SNa sodium adduct—1083.6167. Found 1083.6151.

$^1$H NMR (600 MHz, Chloroform-d) δ 6.45 (dd, J=14.5, 11.0 Hz, 1H), 6.21 (dd, J=14.6, 10.7 Hz, 1H), 6.14 (dd, J=14.8, 10.8 Hz, 1H), 5.98 (d, J=10.9 Hz, 1H), 5.35 (dd, J=14.8, 9.8 Hz, 1H), 5.20 (d, J=5.8 Hz, 1H), 5.09 (d, J=9.8 Hz, 1H), 4.72 (d, J=12.1 Hz, 1H), 4.61 (m, 1H), 4.46 (s, 1H), 4.10 (d, J=6.9 Hz, 1H), 3.96 (t, J=11.4 Hz, 1H), **3.73 (t, J=5.5 Hz, 2H), 3.68 (d, J=6.9 Hz, 1H), 3.59 (m, 4H), 3.53 (m, 2H), 3.46 (s, 3H), 3.28 (s, 3H), 3.21 (m, 1H), 3.13 (m, 1H), 3.07 (m, 2H), 3.05-2.99 (m, 1H), 2.97 (q, J=8.0 Hz, 1H), 2.78 (dq, J=14.4, 7.1 Hz, 1H), 2.44-2.33 (m, 1H), 2.31 (m, 2H), 2.27-2.19 (m, 1H), 2.19-2.12 (m, 2H), 2.07-1.94 (m, 2H), 1.88 (s, 3H), 1.83 (d, J=12.9 Hz, 1H), 1.74 (m, 3H), 1.66 (m, 7H), 1.56-1.44 (m, 1H), 1.43 (m, 2H), 1.41-1.15 (m, 12H), 1.04 (m, 7H), 0.91 (m, 8H), 0.84 (d, J=6.7 Hz, 3H), 0.70 (q, J=12.0 Hz, 1H).

Example 19: C16-(1,1-dioxidoisothiazolidin-2-yl)-C32-deoxo-C40-((3-hydroxy-2-(hydroxymethyl)-2-methylpropanoyl)oxy)-rapamycin

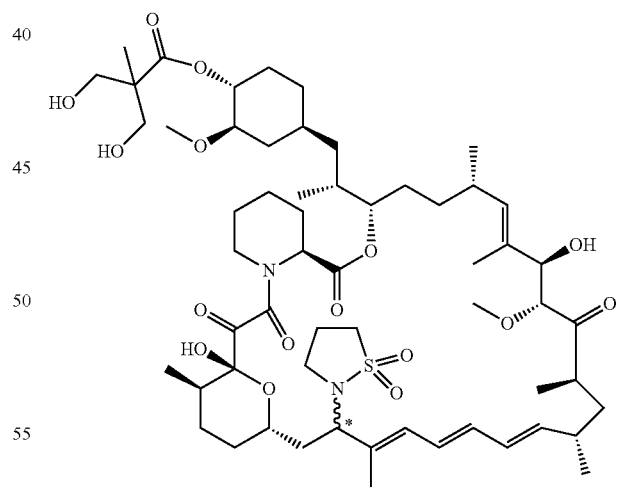

Example 19

*Absolute stereochemistry at C16 not assigned

Intermediate 7 (0.088 g, 0.087 mmol) was combined with isothiazolidine 1,1-dioxide (0.105 g, 0.866 mmol) in anhydrous dichloromethane (0.87 mL). para-Toluenesulfonic acid monohydrate (1.647 mg, 8.66 µmol) was added. The reaction was stirred at room temperature for 30 minutes.

The entire reaction mixture was purified by normal phase flash column chromatography (0-60% acetonitrile-dichloromethane, gradient elution, 12 g silica column, TLC in 30% acetonitrile-dichloromethane) to give Example 19 (0.020 g, 0.017 mmol, 19.9% yield) as a white solid.

Example 19: ESIMS [M+NH4] 1123.0, [M−H] 1104.0
HRMS: Calculated for ammonium adduct C58H92N2O16SNH4-1122.6511; found 1122.652.

$^1$H NMR (600 MHz, Chloroform-d) δ 6.45 (dd, J=14.7, 10.9 Hz, 1H), 6.22 (dd, J=14.7, 10.7 Hz, 1H), 6.13 (dd, J=14.9, 10.6 Hz, 1H), 5.99 (d, J=10.9 Hz, 1H), 5.35 (dd, J=14.9, 9.8 Hz, 1H), 5.21 (d, J=5.8 Hz, 1H), 5.10 (d, J=9.9 Hz, 1H), 4.73 (ddd, J=11.0, 9.2, 4.7 Hz, 1H), 4.69 (d, J=12.4 Hz, 1H), 4.64 (m, 1H), 4.49 (s, 1H), 4.13 (d, J=6.5 Hz, 1H), 3.97 (t, J=11.3 Hz, 1H), 3.84 (dd, J=18.5, 11.4 Hz, 2H), 3.78-3.69 (m, 2H), 3.64 (m, 2H), 3.56 (td, J=13.5, 3.0 Hz, 1H), 3.43-3.31 (m, 4H), 3.28 (m, 3H), 3.26-3.17 (m, 2H), 3.12-2.92 (m, 3H), 2.76-2.68 (m, 1H), 2.45-2.34 (m, 1H), 2.31-2.21 (m, 3H), 2.20-2.10 (m, 3H), 2.06 (m, 1H), 1.87 (m, 4H), 1.75 (m, 3H), 1.71-1.59 (m, 3H), 1.60 (s, 3H), 1.60-1.50 (m, 1H), 1.48-1.39 (m, 1H), 1.42-1.31 (m, 2H), 1.33-1.20 (m, 8H), 1.11 (s, 3H), 1.11-1.05 (m, 2H), 1.03 (dd, J=18.2, 6.6 Hz, 6H), 0.99-0.82 (m, 10H), 0.79 (q, J=12.0 Hz, 1H).

Example 20: Biological Assays and Data

The activity of a compound according to the disclosure was assessed by the following in vitro & in vivo methods.
Pharmacological Characterization
Materials and Methods
Cell-based assay for rapalog potency determination. Rapalog potency was determined using MEF TSC1−/− cell based assay. MEF TSC1−/− cells are Mouse Embryonic Fibroblasts deficient in Tuberous sclerosis protein—TSC1, which negatively regulates mTORC1 signaling and thus display constitutive mTORC1 activation, resulting in phosphorylation (activation) of downstream molecules. This cell-based assay is used to measure inhibition (de-phosphorylation) of S6 and 4EBP1 by rapalogs or other mTOR inhibitors.

MEF TSC1−/− cells were plated on Poly-D-lysine coated 384 well Griener clear bottom plates and incubated overnight at 37° C., 5% $CO_2$. On the following day, cells were washed 8 times with "Hard starve" solution (1 L DPBS+1 g D-(+) glucose+10 ml of 7.5% Sodium Bicarbonate+20 ml of 1M HEPES) and incubated for further 2 hours in the same solution. Cells were next treated with compounds with decreasing concentrations (8 points at 3.16 fold dilutions) and incubated for 2 hours at 37° C., 5% $CO_2$. Cells were fixed with 4% paraformaldehyde for 30 min and washed 5 times with TBS-EDTA followed by immuno-staining with fluorescent tag labeled antibodies for pS6 (Ser240/244) (Cell Signaling #9468) and p4EBP1 (Thr 37/46) (Cell Signaling #5123). Nuclei were visualized with Hoechst (ThermoFisher Scientific #H3570) staining. Cells were imaged (InCell 600) using respective fluorescence channels and the potency of mTOR inhibitors was defined by pS6 $IC_{50}$ (nM).

Animal maintenance, treatment with compounds and tissue collection. All procedures involving animals were approved by the Institutional Animal Care and Use Committee of the Novartis Institutes for Biomedical Research, Cambridge, MA, USA. Adult Sprague Dawley (SD) male rats were purchased from Envigo (Indianapolis, USA) or Charles River (USA). Once imported, rats were maintained at the specific pathogen free facilities with controlled temperature and light (22° C., 12-h light/12-h dark cycle: lights on at 0600 h/lights off at 1800 h) and with ad libitum access to food and water. Rats were acclimated for at least 3 days before experiments commenced.

Example 2 and RAD001 were formulated for oral (per os, p.o.) dosing. Blank formulations (without Example 2 or RAD001) served as vehicle controls. Rats received a single dosed of Example 2, RAD001 or a respective vehicle p.o. At pre-determined times following treatment, rats were anesthetized with 3.5% isoflurane and euthanized. Various organs were collected and frozen in liquid nitrogen. Blood was collected via a tail vein or a cardiac puncture (terminal) and frozen for further pharmacokinetics analyses. All tissues were stored at −80° C. until analyzed.

Determination of Example 2 and RAD001 concentrations in blood and tissues. Concentrations were determined using HPLC/Mass spectrometry.

Protein extraction and immunoblotting. For protein extraction, snap frozen tissues were lysed in MSD Lysis Buffer (MSD, Rockville, Maryland), supplemented with complete EDTA free protease inhibitor and PhosSTOP phosphatase inhibitor tablets (Roche, Manheim, Germany), and centrifuged at 13,000 g for 20 min at 4° C. The resultant supernatant was used for immunoblotting. Protein was quantified with BCA protein assay (Thermo Scientific, MA). Samples were resolved on 4-20% Criterion™ TGX™ Precast Midi Protein gels (Bio-Rad, CA) and transferred onto nitrocellulose membranes (Bio-Rad, CA) using a Trans Turbo Blot system (Bio-Rad, CA). Immunoblotting was performed with antibodies to p-S6 and t-S6 from Cell Signaling Technologies (all 1:1000 in TBS-T with 5% BSA). The 'p' and 't' prefixes signify 'phosphorylated' and 'total' forms respectively. HRP-conjugated secondary antibodies against rabbit (#7074) were from Cell Signaling Technologies, MA. The chemiluminescence signal was generated using SuperSignal™ West Femto Enhanced Chemiluminescent Substrate (#34095, Thermo Scientific, MA) or Western Lightning® Plus-ECL Enhanced Chemiluminescence Substrate (NEL103001EA, Perkin Elmer, MA) and was captured using the ChemiDoc MP Imaging System (Bio-Rad). Resultant digital images were converted into a TIFF format and quantified using ImageJ software.

Generating FKPB12 knock-down cells. A CRISPR/CAS9 vector containing gRNA sequence that targets the FKBP12 C-terminus (GCTTCTAAAACTGGAA TGAC (SEQ ID NO: 1)) was transfected into 293T cells. Selection was performed with puromycin for 48 hours and cells were plated for colony formation. FKBP12 knock-down clones were screened by immunoblotting with an anti-FKBP12 antibody (Thermo Scientific, Pierce #PA1-026A). Clones with significantly reduced FKBP12 (approximately 80% reduction relative to levels in unperturbed 293T cells) were selected.

Generation of FKPB12 knock-out cells. A CRISPR/Cas9 system was used to deliver ribonucleoprotein complexes containing guide RNA (gRNA) sequence that targets FKBP12 (GCCACTACTCACCGTCTCCT (SEQ ID NO: 2)) into 293T cells, using the Amaxa® 4D-Nucleofector™ X Kit (Lonza, V4XC-2032). Cell clones were screened by immunoblotting with an anti-FKBP12 antibody (Novus, NB300-508) and single clones demonstrating a complete FKBP12 knock-out (no measureable FKBP12) were selected.

Treatment of wild-type (WT), FKBP12 knock-down and FKBP12 knock-out 293T cells with RAD001 and Example 2. WT, FKBP12 knock-down and FKBP12 knock-out 293T cells were plated at a density of 30,000 cells per well in poly-D-Lysine coated 96-well plates (Corning, #354461) in Dulbecco's modified Eagle's medium (ThermoFisher, #11995-065) supplemented with 10% fetal bovine serum (ThermoFisher, #16140-071). Cells were incubated at 37° C., 5% $CO_2$ for 48 hours until they reached 80% confluence.

Cells were treated with RAD001 and Example 2 using a 12-point dose range from 1000 nM to 0.0033 nM for 2 hours at 37° C. in duplicates. Media supplemented with blank Dimethyl sulfoxide (DMSO) was used as a control for both compounds. Phosphorylated amounts of S6K1 (Thr389) were detected by a sandwich ELISA kit (Cell signaling, #7063C) following the manufacture's protocol.

SPR Assay to Determine Binding Affinity to FK506-Binding Proteins (FKBP).

N-terminal avi-his6 tagged FKBP fusions to FKBP12, FKBP51 and FKBP52 were expressed in E. coli and purified using standard chromatography. Each protein was subsequently immobilized on a streptavidin chip in a Biacore 8K SPR instrument (GE Healthcare). Using single-cycle kinetics, compound titrations were flowed at 45 uL/min over each surface using 2-minute association and 30-minute dissociation phases in a buffer containing 50 mM Tris pH 7.5/150 mM NaCl/0.01% Tween 20/1 mM DTT/2% DMSO. The data was fit using low molecular weight (LMW) single-cycle kinetics. The equilibrium dissociation constants ($K_D$) are reported.

Differential pharmacology of rapalogs may be achieved in different cell or tissue types depending on 1) the relative abundance of FKBP homologs in these cells/tissues and 2) the specificity of binding to these different FKBP homologs (Mol. Cell Biol. (2013) 33:1357-1367).

Results

In vitro potency of mTOR inhibitors was defined by pS6 $IC_{50}$ (nM) in MEF TSC1−/− cells.

| Compound | IC50 (nM) |
|---|---|
| Rapamycin | 0.050 |
| RAD001 | 0.050 |
| Intermediate 1 | 0.092 |
| Intermediate 3 | 0.0591 |
| Intermediate 4 | 0.066 |
| Intermediate 5 | 0.106 |
| Example 1 | 2.4 |
| Example 2 | 0.274 |
| Example 3 | 1.45 |
| Example 4 | >500 |
| Example 5 | 153 |
| Example 6 | 0.170 |
| Example 7 | 0.300 |
| Example 8 | 0.328 |
| Example 9 | 1.45 |
| Example 10 | 0.557 |
| Example 11 | 3.33 |
| Example 12 | 0.374 |
| Example 13 | 0.656 |
| Example 14 | 7.77 |
| Example 15 | 3.2 |
| Example 16 | 0.645 |
| Example 17 | 1.1 |
| Example 18 | 1.55 |

IC50 values are calculated as the average from multiple assays.

The equilibrium dissociation constants ($K_D$) to FKBP12, FKBP51, and FKBP52.

| Compound | FKBP binding protein | Average $K_D$ (nM) |
|---|---|---|
| RAD001 | FKBP12: | 500 |
| | FKBP51: | 811 |
| | FKBP52: | 1765 |
| Example 1 | FKBP12: | 0.35 |
| | FKBP51: | 153 |
| | FKBP52: | 174 |
| Example 2 | FKBP12: | 16 |
| | FKBP51: | >10000 |
| | FKBP52: | >10000 |
| Example 6 | FKBP12: | 0.32 |
| | FKBP51: | 39 |
| | FKBP52: | 53 |
| Example 7 | FKBP12: | 1.2 |
| | FKBP51: | 287 |
| | FKBP52: | 236 |
| Example 10 | FKBP12: | 1.6 |
| | FKBP51: | 95 |
| | FKBP52: | 176 |
| Example 14 | FKBP12: | 16 |
| | FKBP51: | — |
| | FKBP52: | 542 |
| Example 16 | FKBP12: | 35 |
| | FKBP51: | 4064 |
| | FKBP52: | 4073 |

Figure 3:
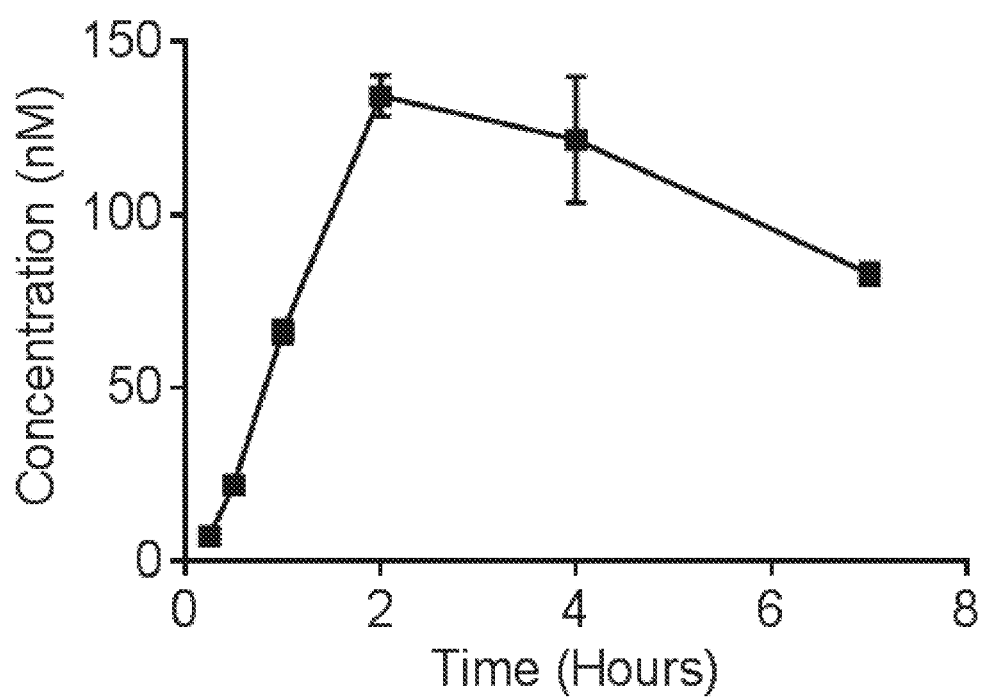
FIG. 3 is a line graph showing the pharmacokinetic profile of Example 2 in rats following a single p.o. dose of 3 mg/kg. Y axis—blood concentrations of Example 2 (nM). X axis—time (hours) for blood collection following Example 2 administration. Data are mean±standard deviation from 3 rats.

Pharmacokinetic profile of Example 2 in rats. Rats aged 4 months were treated with a single p.o. dose of Example 2 at 3 mg/kg and blood was collected at 0.25, 0.5, 1, 2, 4 and 7 h following dosing. In this experiment, Example 2 was formulated in 15% Polyethylene Glycol (PEG) 300, 7.5% Solutol HS15, 7.5% Cremophore EL in MilliQ water. Concentrations of Example 2 were measured by HPLC-MS (FIG. 3).

Comparative Blood and Brain Concentrations of Example 2 and RAD001 in Rats.

Figure 4A:
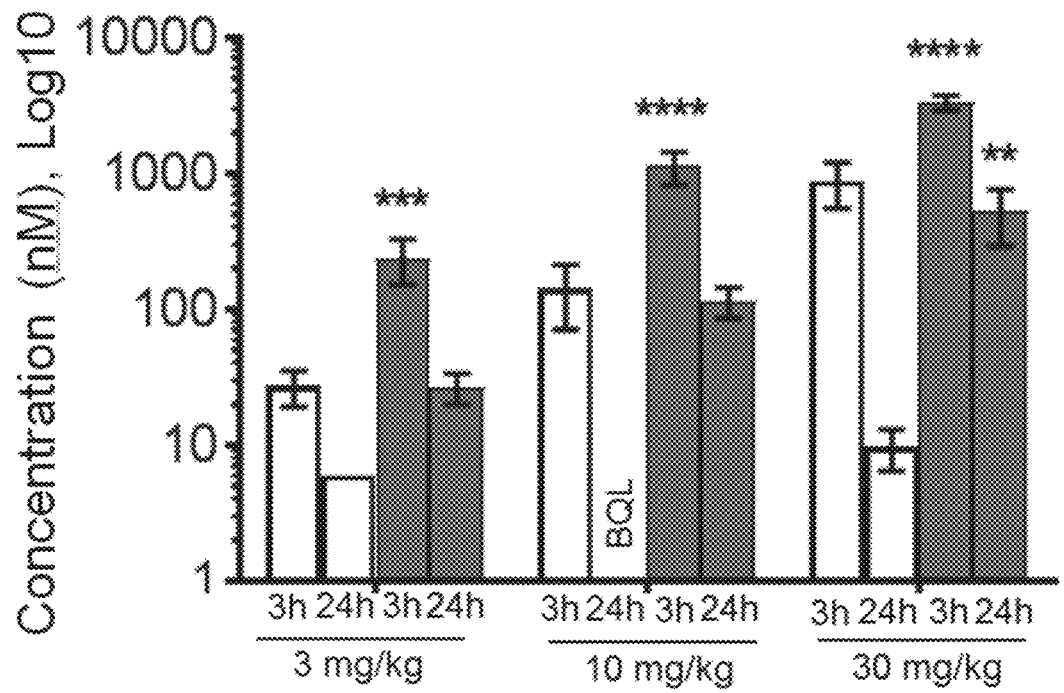
FIG. 4A is a bar graph showing comparative blood concentrations of RAD001 (open bars) and Example 2 (solid bars) in rats orally given a single dose of either compound at 3, 10 and 30 mg/kg. Compound concentrations were measured 3 and 24 hours (h) following dosing. Data are mean±standard deviation from 5-6 rats in each group. Rats where a compound was below quantification limit were excluded from data analysis: this applies to RAD001 treated groups. Asterisk (*) indicates significant difference between respective RAD001 and Example 2 treated groups. P<0.01; *P<0.001; ****P<0.0001, t-tests. BQL—below quantification limit. Y axis compound concentrations in blood (nM). X axis—time (3 and 24 hours) following oral dosing and orally given doses (3, 10 and 30 mg/kg).
Figure 4B:
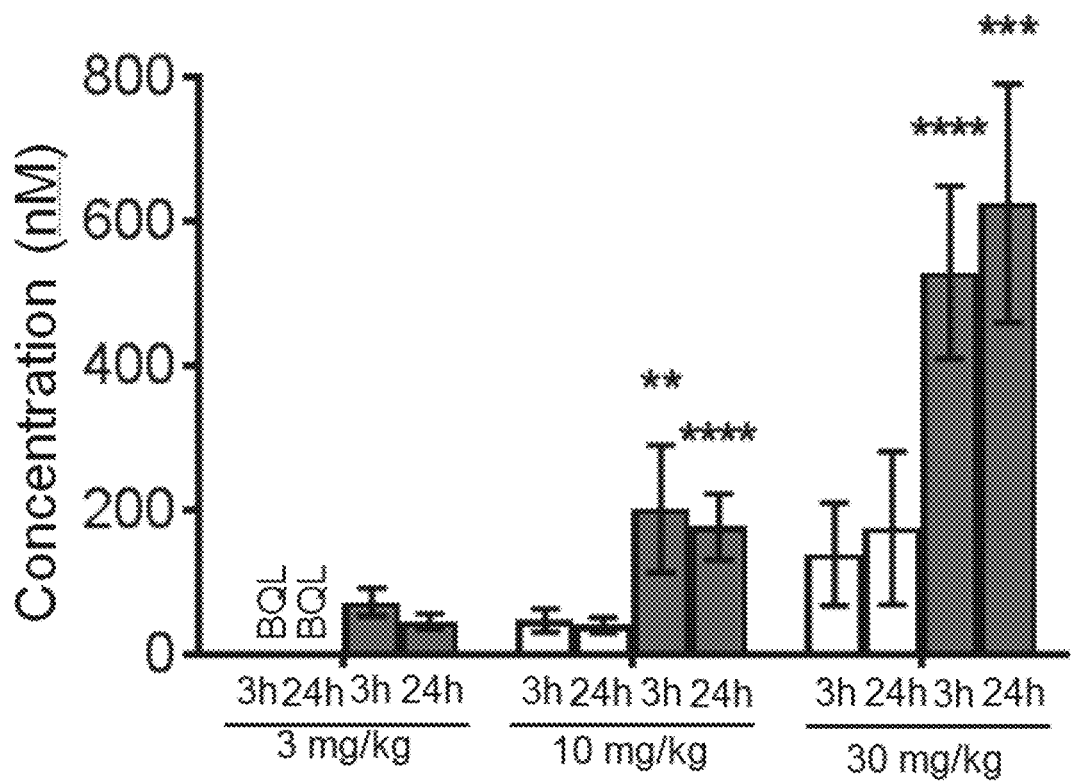
FIG. 4B is a bar graph showing comparative brain concentrations of RAD001 (open bars) and Example 2 (solid bars) in rats orally given as a single dose of either compound at 3, 10 and 30 mg/kg. Compound concentrations were measured 3 and 24 hours (h) following dosing. Data are mean±standard deviation. 5-6 rats were used in each group. Rats where a compound was below quantification limit were excluded from data analysis: this applies to RAD001 treated groups. Asterisk (*) indicates significant difference between respective RAD001 and Example 2 treated groups. P<0.01; *P<0.001; ****P<0.0001, t-tests. BQL—below quantification limit. Y axis compound concentrations in brain (nM). X axis—time (3 and 24 hours) following dosing and orally given doses (3, 10 and 30 mg/kg).

Rats aged 4 months were treated p.o. with Example 2 (formulated in 15% PEG300, 7.5% Solutol HS15, 7.5% Cremophore EL in MilliQ water) at 3, 10 and 30 mg/kg. In another experiment, rats aged 8 weeks were treated p.o. with RAD001 (formulated as a microemulsion at 2% (w/w) and diluted to a final concentration in MilliQ water) at 3, 10 and 30 mg/kg. Blood and brain tissues were collected at 3 hours (h) and 24 h following treatment to determine concentrations of the compounds. When administered at the same doses (3, 10 and 30 mg/kg), blood and brain concentrations for Example 2 were higher compared with those for RAD001 (FIGS. 4A and 4B).

Figure 4C:
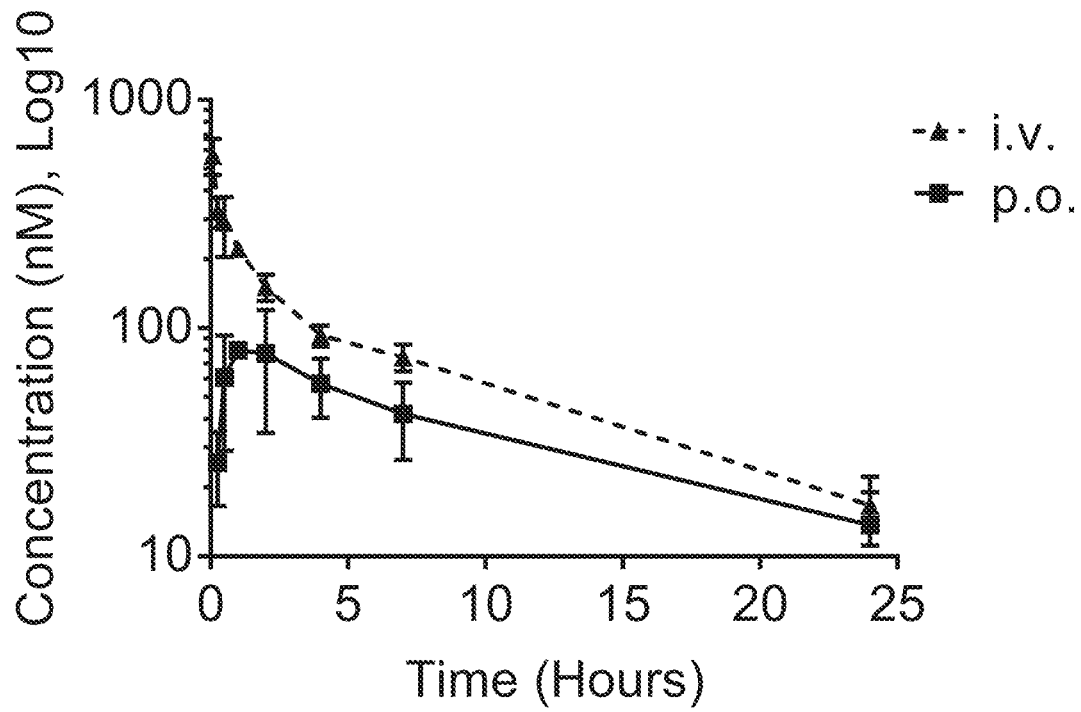
FIG. 4C shows blood concentration of Example 2 in rats following intra venous (i.v.) and oral (p.o.) dosing. Y axis—blood concentrations of Example 2 (nM). X axis—time (hours) for blood collection following Example 2 administration. Data are mean±standard deviation from 3 rats.
Figure 4D:
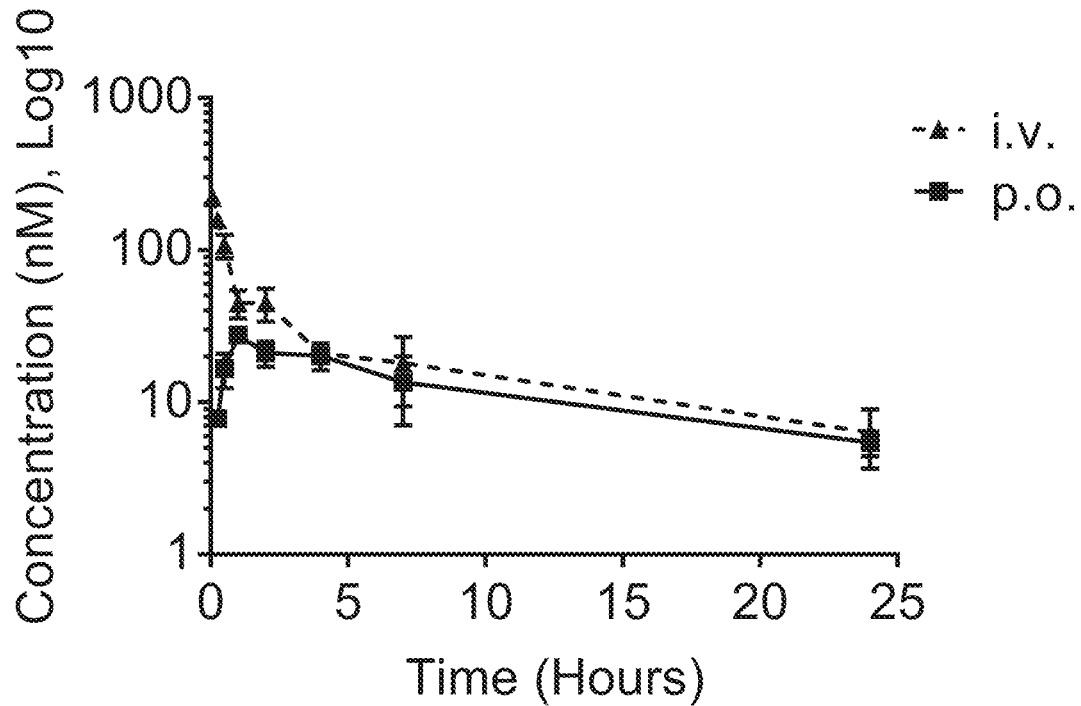
FIG. 4D shows blood concentration of RAD001 in rats following intra venous (i.v.) and oral (p.o) dosing. Y axis—blood concentrations of RAD001 (nM). X axis—time (hours) for blood collection following RAD001 administration. Data are mean±standard deviation from 3 rats.

To compare bioavailability of Example 2 versus RAD001 in the rat, compounds were formulated as solution formulations: Example 1 was formulated in 15% PEG300, 7.5% Solutol HS15, 7.5% Cremophore EL in PBS and RAD001 was formulated in 10% PEG300, 10% Solutol HS15, 10% Cremophore EL in PBS. Compounds were administered to rats aged 7-9 weeks (N=3 per group) p.o. at 3 mg/kg and intravenously (i.v). at 1 mg/kg (FIGS. 4C and 4D). For Example 2 and RAD001 respectively, bioavailability was 18% and 19%, i.v. terminal half-life 9.9 h and 9.5 h, clearance 9 mL/min/kg and 32 mL/min/kg and Vdss (volume of distribution at the steady state) 4.4 L/kg and 18.8 L/kg.

Figure 5A:
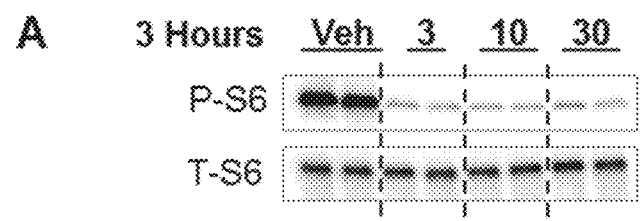
FIGS. 5A-5D show that Example 2 inhibits the mTORC1 pathway in the rat liver. Rats were given a single oral dose of Example 2 at 3 or 10 or 30 mg/kg, and liver samples were collected at 3 hours (h) and 24 h following dosing. Rats treated with a vehicle (Veh) were used as a control. (5A) and (5C) show immunoblot images of phosphorylated (p-) and total (t-) S6 proteins in rat livers treated with a vehicle or 3 or 10 or 30 mg/kg of Example 2 and analyzed at 3 h (5A) and 24 h (5C) following treatment. Histograms in (5B) and (5D) show densitometric quantification of p-S6 to t-S6 at 3 h (5B) and 24 h (5D) following treatment. In histograms (5B and 5D), average arbitrary values that indicate p-S6/t-S6 ratios are shown above each bar. X axes represent orally given doses (3, 10, 30 mg/kg). Y-axes represent arbitrary units. Six rats were used in each experimental group. Data are mean±standard deviation. Data were analyzed with a one way ANOVA followed by Dunnett's multiple comparison tests, where means from all groups were compared to the vehicle treated group. P<0.01, **P<0.001, ns not significant.
Figure 5B:
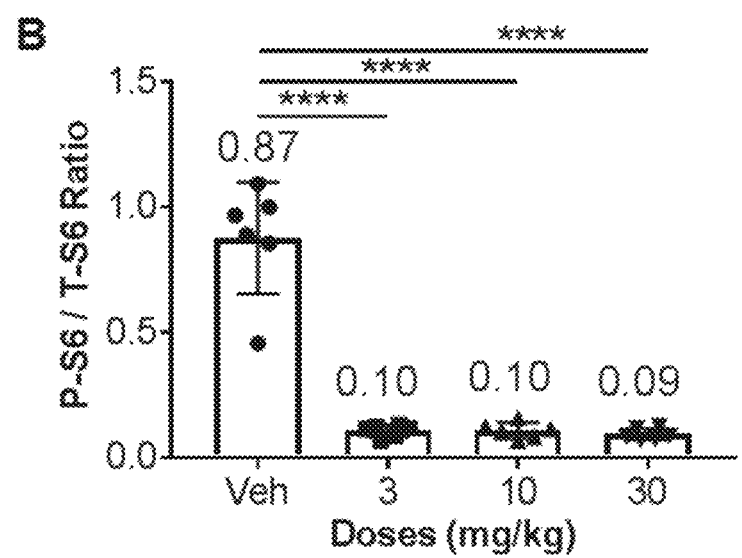
Figure 5C:
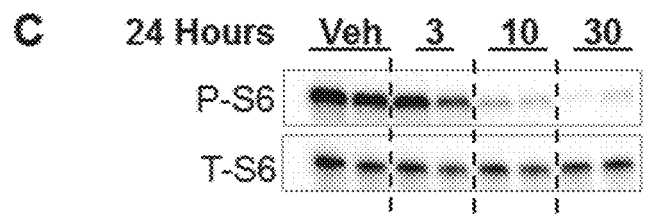
Figure 5D:
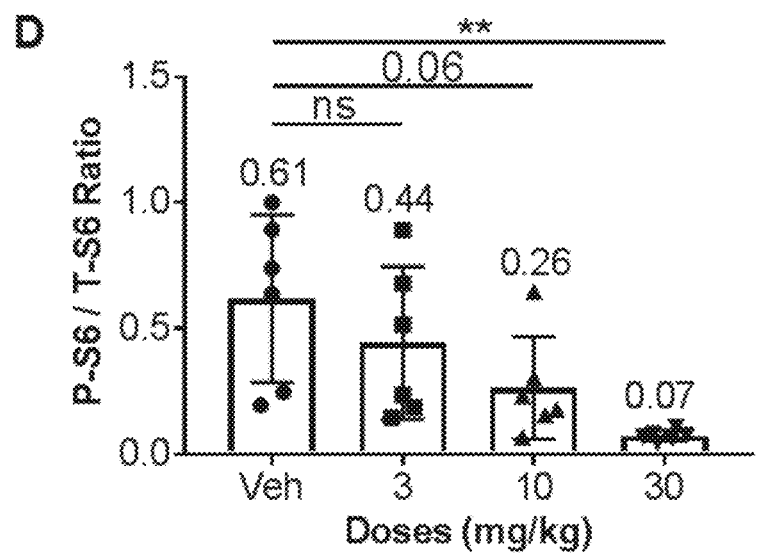

Example 2 inhibits mTORC1 pathway in the rat liver. The ability of Example 2 to inhibit mTORC1 pathway in vivo was determined in rats aged 4 months (FIG. 5A-5D). A single dose of Example 2 at 3, 10 and 30 mg/kg resulted in a significant de-phosphorylation (inactivation) of S6 in rat livers (compared with the vehicle control), three hours following dosing (FIGS. 5A and 5B). S6 remained inactivated 24 h following dosing with 10 (trend p=0.06) and 30 mg/kg (FIGS. 5C and 5D).

Figure 6A:
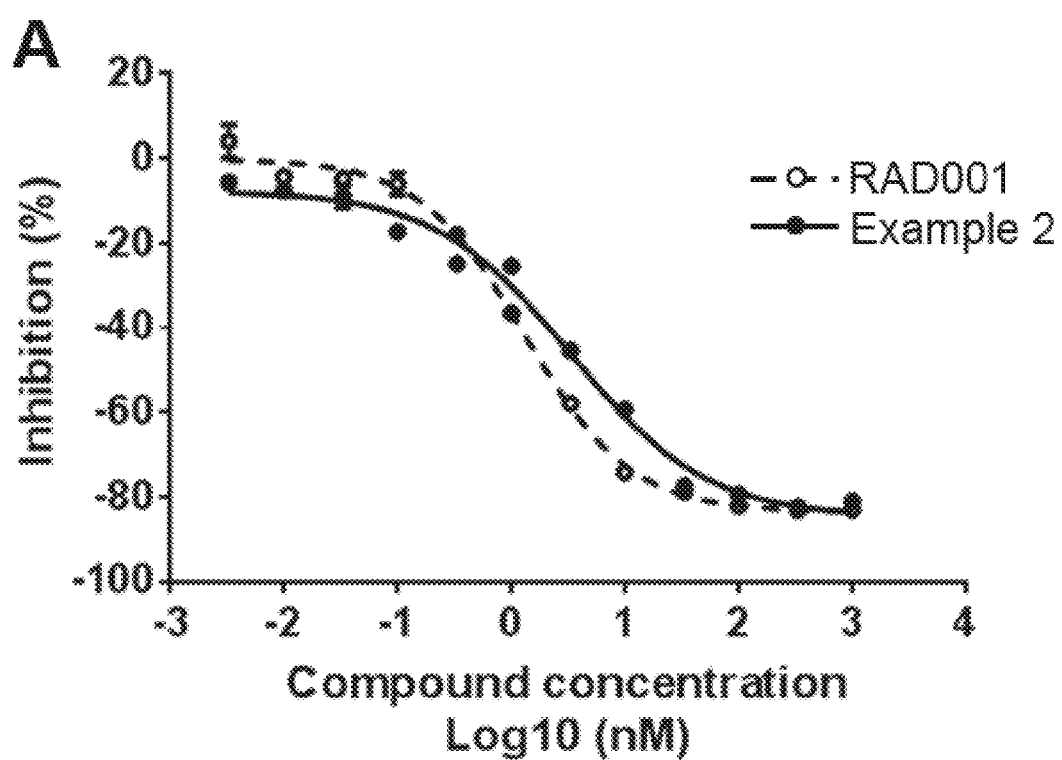
FIG. 6A-6C shows inhibition of S6K1 (Thr389) in wild-type (6A), FKBP12 knock-down (6B) and FKBP12 knock-out (6C) 293T cells, following treatment with RAD001 (dotted line) and Example 2 (solid line). Cells were treated in triplicate. The Y axis represents percent inhibition relative to the S6K1 (Thr389) level in cells treated with media plus DMSO. The X axis represents concentrations for RAD001 and Example 2.
Figure 6B:
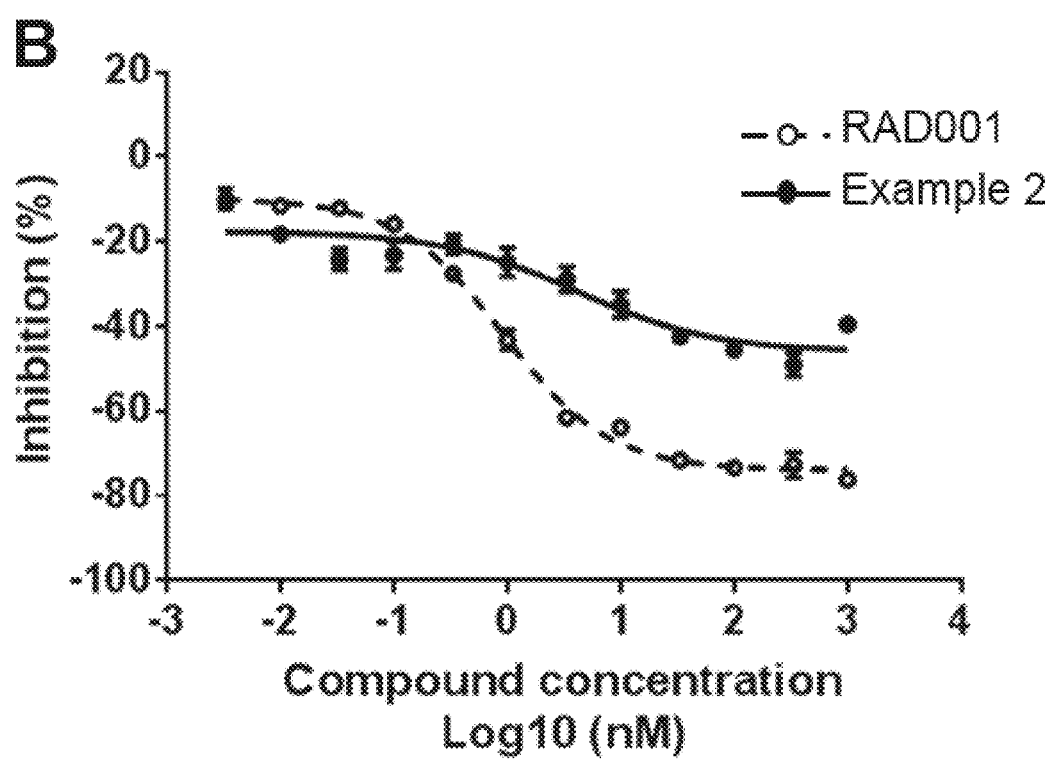
Figure 6C:
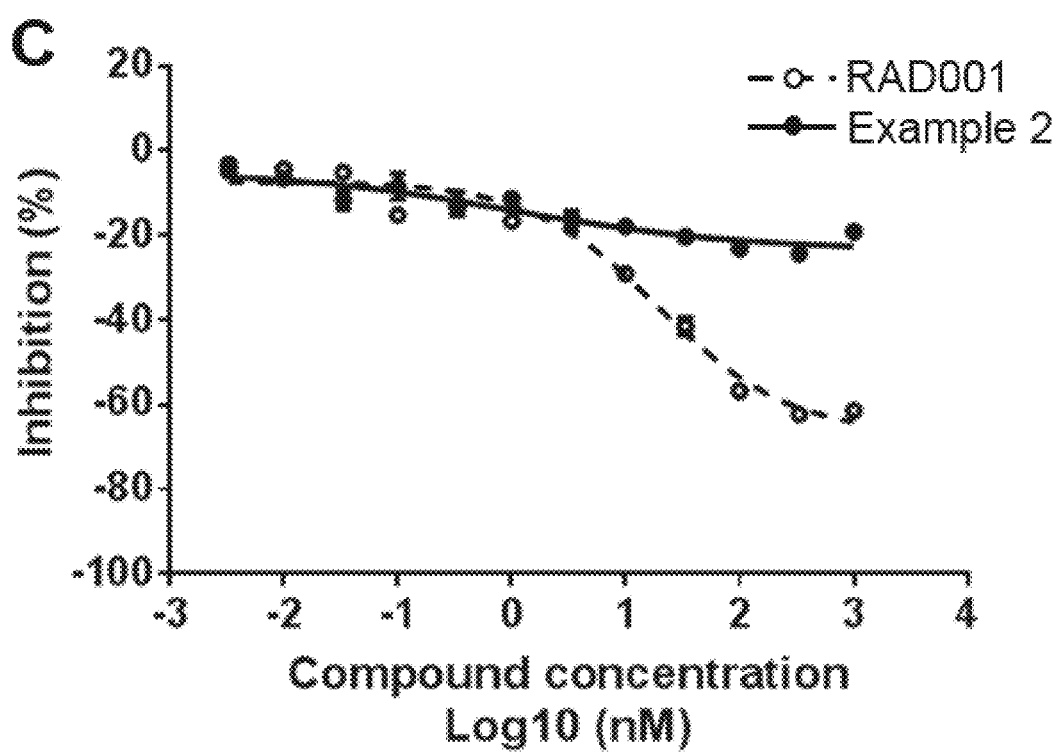

FKBP12 is required for the inhibitory effect of Example 2, but not RAD001. Phosphorylated amounts of S6K1 (Thr389) were measured in WT, FKBP12 knock-down and FKBP12 knock-out 293T cells, treated with RAD001 or Example 2. S6K1 is a downstream target of mTORC1 and phosphorylation of its rapalog-sensitive Thr389 site is used as a functional readout of mTORC1 activity. Lee, C. H., Inoki, K. and Guan, K. L. (2007). mTOR pathway as a target in tissue hypertrophy. Annu. Rev. Pharmacol. Toxicol. 47, 443-467. In WT 293T cells, both RAD001 and Example 2 were efficacious at inhibiting S6K1(Thr389) by ~80% (FIG. 6A). In FKBP12 knock-down cells, Example 2 failed to inhibit S6K1(Thr389) phosphorylation to the same level as RAD001: the maximum inhibition of S6K1(Thr389) by RAD001 was 70%, while inhibition achieved by Example 2 was 40% (FIG. 6B). In FKBP12 knock-out cells, Example 2 failed to inhibit S6K1(Thr389) phosphorylation, while >60% inhibition was still achieved by RAD001 (FIG. 6C). These results indicate that pharmacological effects of Example 2 are restricted to FKBP12. Such specificity of Example 2 to FKBP12 may facilitate targeting cells and tissues with relatively high levels of FKBP12 expression, while avoiding (or minimizing) side effects in the tissues where FKBP12 is weakly expressed.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects of the disclosure, is/are referred to as comprising particular elements and/or features, certain embodiments of the disclosure or aspects of the disclosure consist, or consist essentially of, such elements and/or features. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the disclosure, as defined in the following claims.

We claim:

1. A method of treating a disease or a disorder mediated by a mTOR pathway in a subject in need thereof, the method comprising administering to the subject a therapeutically effective amount of a compound of formula (I) or a pharmaceutically acceptable salt thereof, wherein:

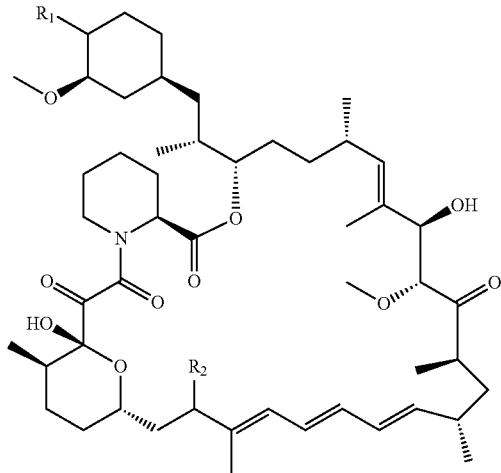
(I)

$R_1$ is selected from the group consisting of hydroxy,

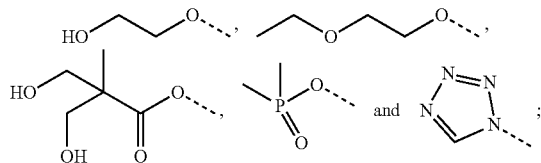

and $R_2$ is selected from the group consisting of

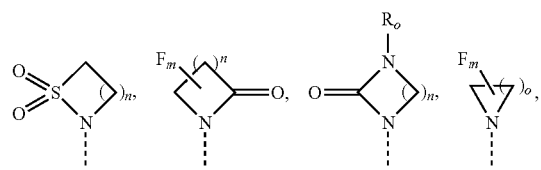

-continued

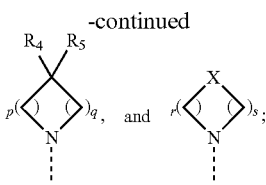

wherein
  m is 0, 1, 2 or 3;
  n is 1, 2, or 3;
  o is 1, 2, 3, 4, 5 or 6;
  p is 1, 2, 3, 4 or 5
  q is 1, 2, 3, 4 or 5 wherein the sum of p and q is 2, 3, 4, 5 or 6;
  r is 2, 3 or 4;
  s is 2, 3 or 4 wherein the sum of r and s is 4, 5 or 6;
  X is O, S, $NR_6$ or $SO_2$;
  $R_3$ is hydrogen, $C_{1-6}$alkyl, hydroxy$C_{1-6}$alkyl, $C_{3-8}$cycloalkyl$C_{0-6}$alkyl or phenyl$C_{0-6}$alkyl;
  $R_4$ is hydrogen;
  $R_5$ is hydrogen, hydroxy or cyano; or $R_4$ and $R_5$ together form =O; and
  $R_6$ is hydrogen, $C_{1-6}$alkyl, $C_{3-8}$cycloalkyl$C_{0-6}$alkyl, phenyl$C_{0-6}$alkyl, $C_{1-6}$alkyl-CO—, $C_{3-8}$cycloalkyl-$C_{0-6}$alkyl-CO—, $C_{1-6}$alkyl-$SO_2$— or $C_{3-8}$cycloalkyl$C_{0-6}$alkyl-$SO_2$—.

2. The method of claim 1, wherein the disease or disorder is selected from sarcopenia, skin atrophy, cherry angiomas, seborrheic keratoses, brain atrophy, atherosclerosis, arteriosclerosis, pulmonary emphysema, osteoporosis, osteoarthritis, high blood pressure, erectile dysfunction, cataracts, macular degeneration, glaucoma, stroke, cerebrovascular disease, chronic kidney disease, diabetes-associated kidney disease, impaired hepatic function, liver fibrosis, autoimmune hepatitis, endometrial hyperplasia, metabolic dysfunction, renovascular disease, hearing loss, mobility disability, cognitive decline, tendon stiffness, heart dysfunction immune senescence, Parkinson's disease, Alzheimer's disease, cancer, a decrease in immune-surveillance, infections due to an decline in immune-function, chronic obstructive pulmonary disease (COPD), obesity, loss of taste, loss of olfaction, arthritis, type II diabetes diabetic blindness and diabetic neuropathy.

3. The method of claim 1, wherein the disorder is liver fibrosis.

4. A method of treating a disease or a disorder in a subject in need thereof, the method comprising administering to the subject a therapeutically effective amount of a compound of formula (I) or a pharmaceutically acceptable salt thereof, wherein:

(I)

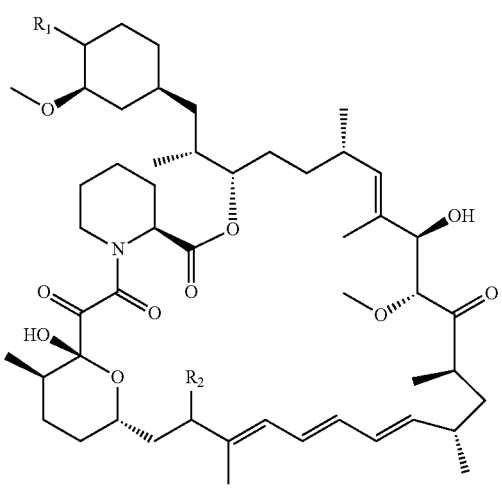

$R_1$ is selected from the group consisting of hydroxy,

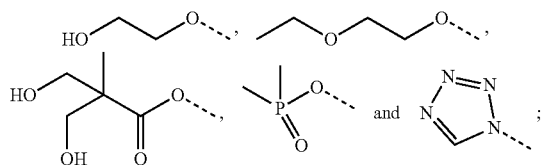

and $R_2$ is selected from the group consisting of

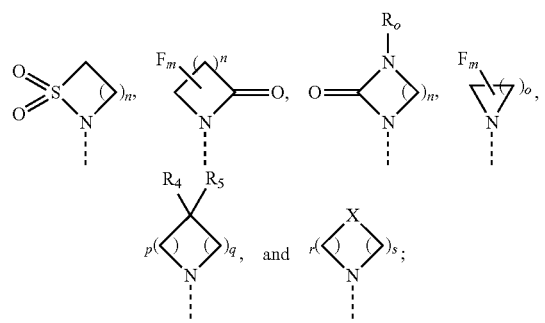

wherein
m is 0, 1, 2 or 3;
n is 1, 2, or 3;
o is 1, 2, 3, 4, 5 or 6;
p is 1, 2, 3, 4 or 5
q is 1, 2, 3, 4 or 5 wherein the sum of p and q is 2, 3, 4, 5 or 6;
r is 2, 3 or 4;
s is 2, 3 or 4 wherein the sum of r and s is 4, 5 or 6;
X is O, S, $NR_6$ or $SO_2$;
$R_3$ is hydrogen, $C_{1-6}$alkyl, hydroxy$C_{1-6}$alkyl, $C_{3-8}$cycloalkyl$C_{0-6}$alkyl or phenyl$C_{0-6}$alkyl;
$R_4$ is hydrogen;
$R_5$ is hydrogen, hydroxy or cyano; or $R_4$ and $R_5$ together form =O; and $R_6$ is hydrogen, $C_{1-6}$alkyl, $C_{3-8}$cycloalkyl$C_{0-6}$alkyl, phenyl$C_{0-6}$alkyl, $C_{1-6}$alkyl-CO—, $C_{3-8}$cycloalkyl$C_{0-6}$alkyl-CO—, $C_{1-6}$alkyl-$SO_2$— or $C_{3-8}$cycloalkyl$C_{0-6}$alkyl-$SO_2$—,
wherein the disease or the disorder is selected from:
Acute or chronic organ or tissue transplant rejection;
Transplant vasculopathies;
vessel intimal thickening, blood vessel obstruction, obstructive coronary atherosclerosis, restenosis;
Autoimmune diseases; inflammatory conditions;
asthma;
Multi-drug resistance (MDR);
Fungal infections;
Infection;
Age-related diseases;
Neurodegenerative diseases;
Proliferative disorders;
Seizures and seizure related disorders;
Mitochondrial myopathy and mitochondrial stress;
liver disorders; and
kidney disorders.

5. The method of claim 4, wherein the disease or the disorder is a liver disorder that includes a process of fibrosis and/or inflammation.

6. The method of claim 4, wherein the disease or the disorder is a kidney disorder that includes a process of fibrosis and/or inflammation.

7. The method of claim 6, wherein the liver disorder is selected from liver fibrosis; liver cirrhosis; liver failure; non-alcohol-associated hepatic steatosis (NASH); and alcohol-associated steatosis.

8. The method of claim 6, wherein the kidney disorder is kidney fibrosis.

9. The method of claim 8, wherein the kidney fibrosis occurs as a result of acute kidney injury.

10. The method of claim 6, wherein the kidney disorder is chronic kidney disorder.

11. The method of claim 6, wherein the kidney disorder is diabetic nephropathy.

12. A method of treating an age-related disease or disorder in a subject in need thereof, the method comprising administering to the subject a therapeutically effective amount of a compound of formula (I), or a pharmaceutically acceptable salt thereof, wherein:

(I)

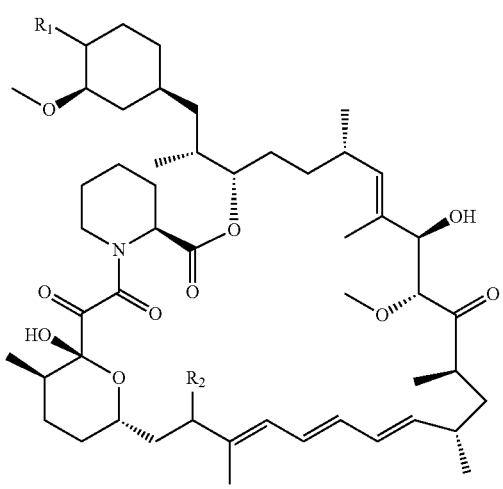

$R_1$ is selected from the group consisting of hydroxy,

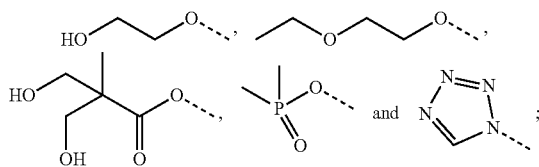

and $R_2$ is selected from the group consisting of

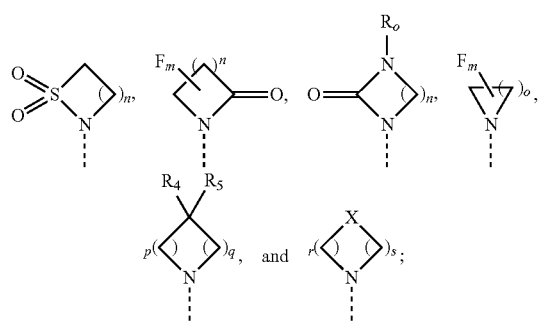

wherein
  m is 0, 1, 2 or 3;
  n is 1, 2, or 3;
  is 1, 2, 3, 4, 5 or 6;
  p is 1, 2, 3, 4 or 5
  q is 1, 2, 3, 4 or 5 wherein the sum of p and q is 2, 3, 4, 5 or 6;
  r is 2, 3 or 4;
  s is 2, 3 or 4 wherein the sum of r and s is 4, 5 or 6;
  X is O, S, $NR_6$ or $SO_2$;
  $R_3$ is hydrogen, $C_{1-6}$alkyl, hydroxy$C_{1-6}$alkyl, $C_{3-8}$cycloalkyl$C_{0-6}$alkyl or phenyl$C_{0-6}$alkyl;
  $R_4$ is hydrogen;
  $R_5$ is hydrogen, hydroxy or cyano; or $R_4$ and $R_5$ together form =O; and
  $R_6$ is hydrogen, $C_{1-6}$alkyl, $C_{3-8}$cycloalkyl$C_{0-6}$alkyl, phenyl$C_{0-6}$alkyl, $C_{1-6}$alkyl-CO—, $C_{3-8}$cycloalkyl$C_{0-6}$alkyl-CO—, $C_{1-6}$alkyl-$SO_2$— or $C_{3-8}$cycloalkyl$C_{0-6}$alkyl-$SO_2$—,
wherein the disease or the disorder is selected from sarcopenia, skin atrophy, cherry angiomas, seborrheic keratoses, brain atrophy, atherosclerosis, arteriosclerosis, pulmonary emphysema, osteoporosis, osteoarthritis, high blood pressure, erectile dysfunction, cataracts, macular degeneration, glaucoma, stroke, cerebrovascular disease, chronic kidney disease, diabetes-associated kidney disease, impaired hepatic function, liver fibrosis, autoimmune hepatitis, endometrial hyperplasia, metabolic dysfunction, renovascular disease, hearing loss, mobility disability, cognitive decline, tendon stiffness, heart dysfunction, immune senescence, Parkinson's disease, Alzheimer's disease, cancer, a decrease in immune-surveillance, a decline in immune-function, chronic obstructive pulmonary disease (COPD), obesity, loss of taste, loss of olfaction, arthritis, type II diabetes, diabetic blindness and diabetic neuropathy.

13. The method of claim 12, wherein the age-related disease or disorder is cancer.

14. The method of claim 13, further comprising a PD-1/PDL-1 inhibitor.

15. The method of claim 13, wherein the cancer is selected from renal cancer, renal cell carcinoma, colorectal cancer, uterine sarcoma, endometrial uterine cancer, endometrial cancer, breast cancer, ovarian cancer, cervical cancer, gastric cancer, fibro-sarcoma, pancreatic cancer, liver cancer, melanoma, leukemia, multiple myeloma, nasopharyngeal cancer, prostate cancer, lung cancer, glioblastoma, bladder cancer, mesothelioma, head cancer, rhabdomyosarcoma, sarcoma, lymphoma, and neck cancer.

16. The method of claim 4, wherein $R_1$ is selected from the group consisting of hydroxy,

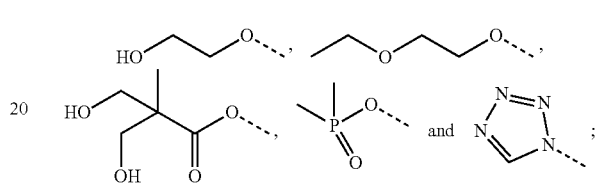

and $R_2$ is selected from the group consisting of

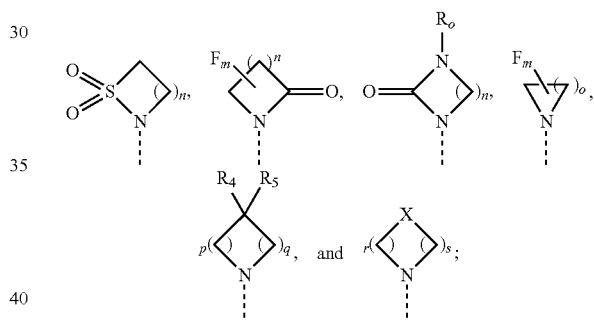

wherein
  m is 0, 1, 2 or 3;
  n is 1, 2 or 3;
  is 1, 2, 3, 4, 5 or 6;
  p is 1, 2, 3, 4 or 5
  q is 1, 2, 3, 4 or 5 wherein the sum of p and q is 2, 3, 4, 5 or 6;
  r is 2, 3 or 4;
  s is 2, 3 or 4 wherein the sum of r and s is 4, 5 or 6;
  X is O, S, $NR_6$ or $SO_2$;
  $R_3$ is hydrogen, $C_{1-6}$alkyl, $C_{3-8}$cycloalkyl$C_{0-6}$alkyl or phenyl$C_{0-6}$alkyl;
  $R_4$ is hydrogen;
  $R_5$ is hydrogen, hydroxy or cyano; or $R_4$ and $R_5$ together form =O; and
  $R_6$ is hydrogen, $C_{1-6}$alkyl, $C_{3-8}$cycloalkyl$C_{0-6}$alkyl, phenyl$C_{0-6}$alkyl, $C_{1-6}$alkyl-CO—, $C_{3-8}$cycloalkyl$C_{0-6}$alkyl-CO—, $C_{1-6}$alkyl-$SO_2$— or $C_{3-8}$cycloalkyl$C_{0-6}$alkyl-$SO_2$—.

17. The method of claim 4, wherein $R_1$ is hydroxy.

18. The method of claim 4, wherein $R_2$ is

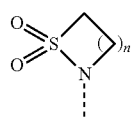

and n is 1, 2 or 3.

19. The method of claim 4, wherein $R_2$ is

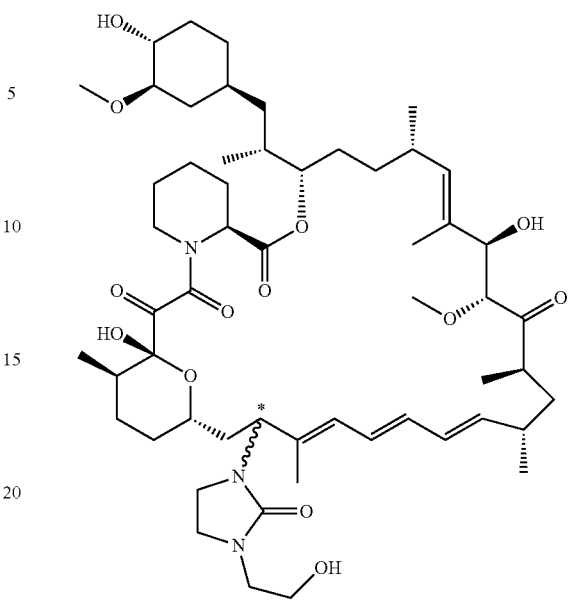

20. The method of claim 4, wherein said compound is selected from:

Structure

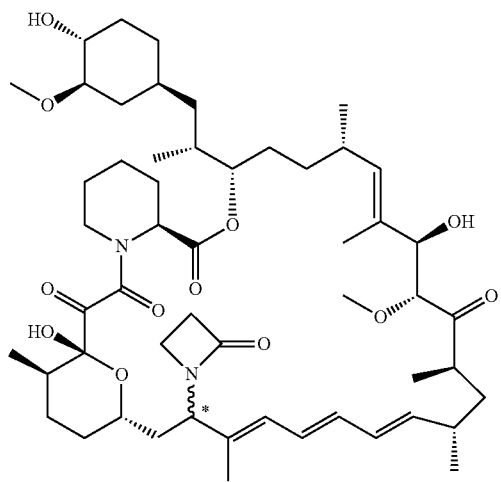

*Absolute sterochemistry at C16 not assigned

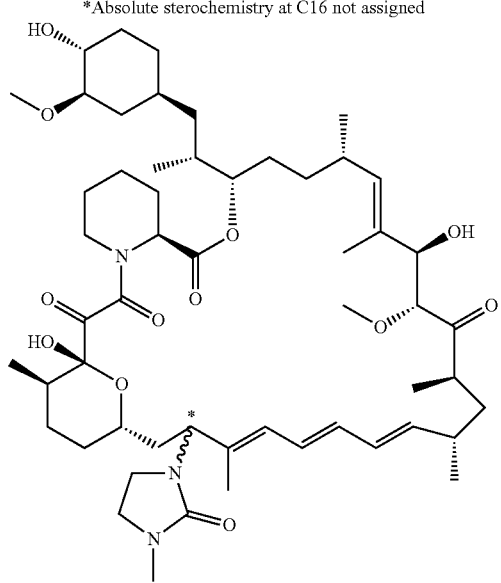

*Absolute sterochemistry at C16 not assigned

-continued

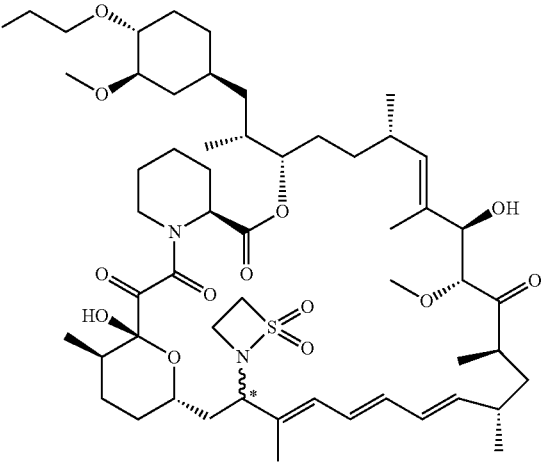

*Absolute sterochemistry at C16 not assigned

*Absolute sterochemistry at C16 not assigned

*Absolute sterochemistry at C16 not assigned

107
-continued
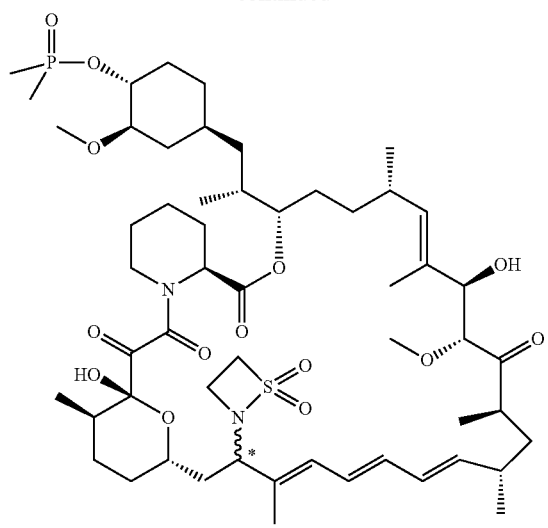
*Absolute sterochemistry at C16 not assigned
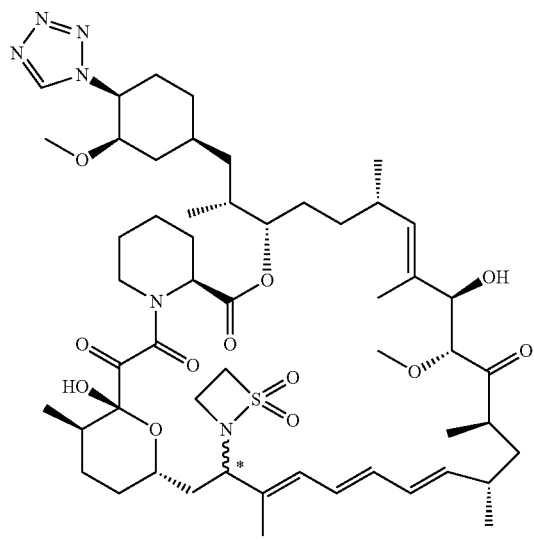
*Absolute sterochemistry at C16 not assigned
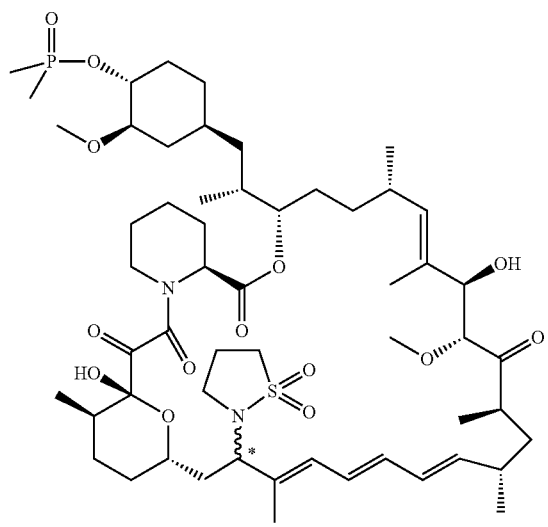
*Absolute sterochemistry at C16 not assigned
108
-continued
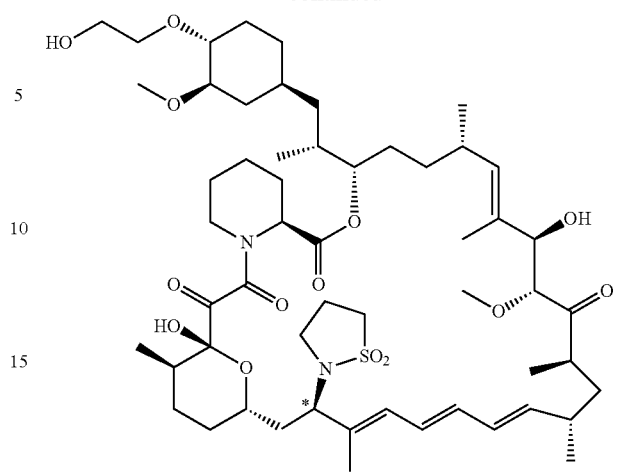
*Absolute sterochemistry at C16 not assigned
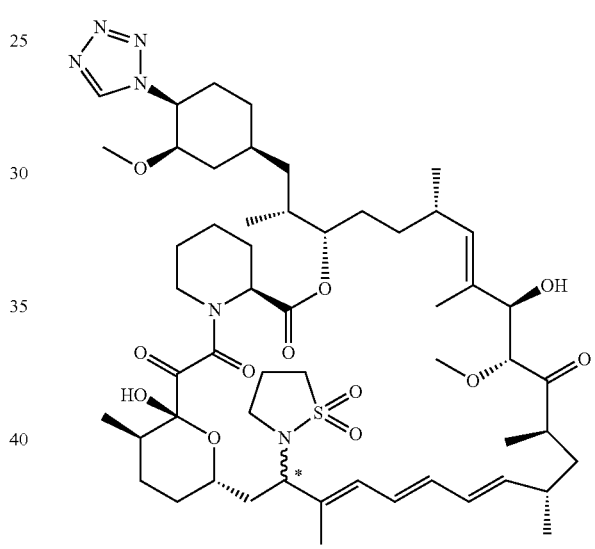
*Absolute sterochemistry at C16 not assigned
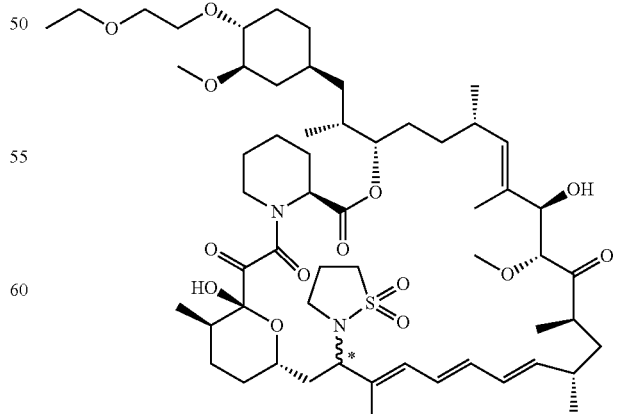
*Absolute sterochemistry at C16 not assigned

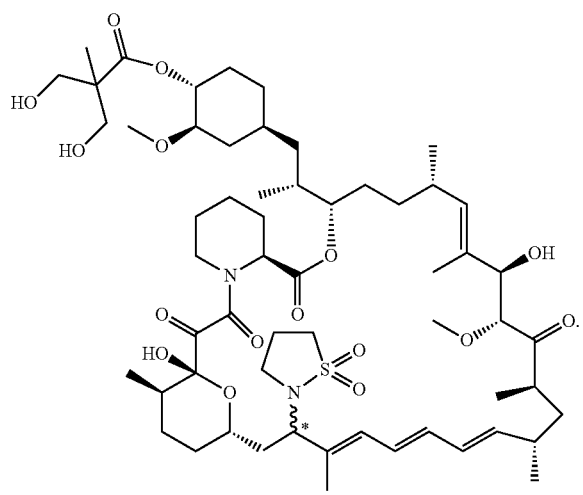
*Absolute sterochemistry at C16 not assigned
21. The method of claim 4, wherein said compound is
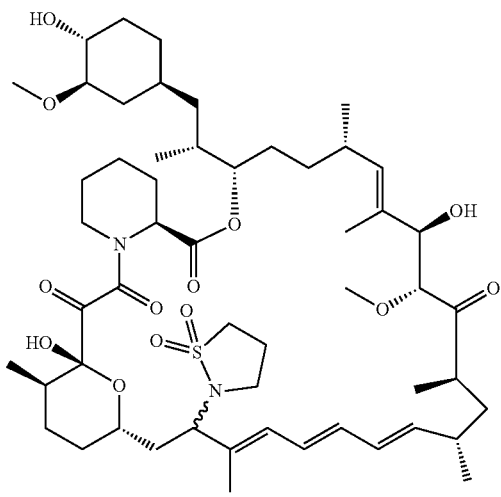 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)C(N3CCCS3(=O)=O)C[C@@H]3CC[C@@H](C)[C@@](O)(O3)C(=O)C(=O)N3CCCC[C@H]3C(=O)O2)CC[C@H]1O]
C16-(1, 1-dioxidoisothiazolidin-2-yl)-C32-deoxo-rapamycin.
22. The method of claim 4, wherein said compound is
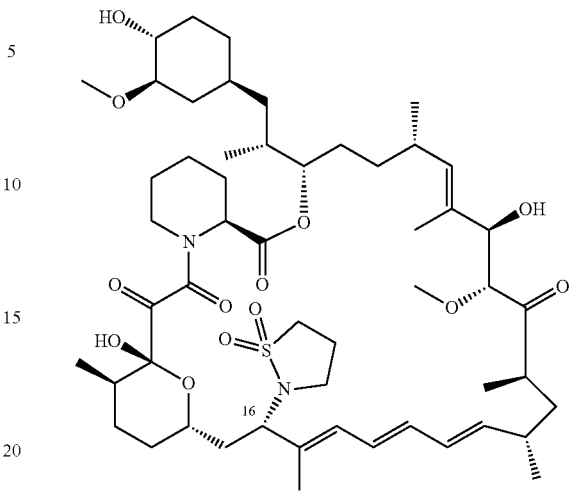
(S)-C16-(1, 1-dioxidoisothiazolidin-2-yl)-C32-deoxo-rapamycin.
23. The method of claim 4, wherein said compound is
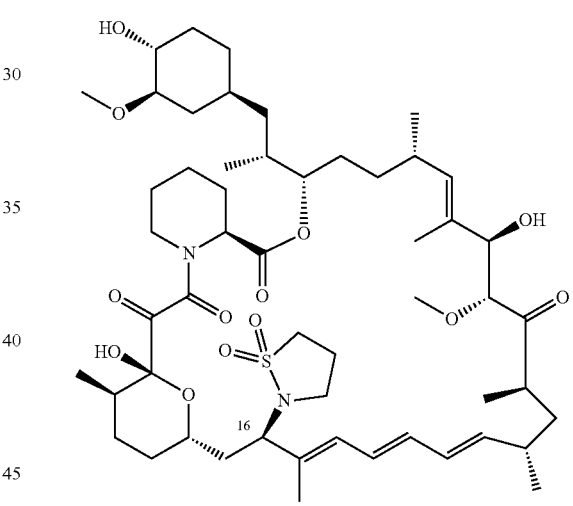
(R)-C16-(1, 1-dioxidoisothiazolidin-2-yl)-C32-deoxo-rapamycin.
* * * * *